(12) United States Patent
Osaka et al.

(10) Patent No.: US 8,790,794 B2
(45) Date of Patent: Jul. 29, 2014

(54) HETEROCYCLIC COMPOUND, LIGHT-EMITTING ELEMENT, LIGHT-EMITTING DEVICE, ELECTRONIC DEVICE, AND LIGHTING DEVICE

(75) Inventors: Harue Osaka, Kanagawa (JP); Takako Takasu, Kanagawa (JP); Nobuharu Ohsawa, Kanagawa (JP); Hiromi Nowatari, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 39 days.

(21) Appl. No.: 13/227,697

(22) Filed: Sep. 8, 2011

(65) Prior Publication Data

US 2012/0061651 A1    Mar. 15, 2012

(30) Foreign Application Priority Data

Sep. 9, 2010 (JP) .................................. 2010-201672
May 31, 2011 (JP) .................................. 2011-122799

(51) Int. Cl.
*H01L 51/54* (2006.01)
*C07D 409/10* (2006.01)

(52) U.S. Cl.
USPC .......................... 428/690; 549/43; 548/305.1

(58) Field of Classification Search
None
See application file for complete search history.

(56) References Cited

U.S. PATENT DOCUMENTS

2008/0308794 A1* 12/2008 Ibe et al. ........................ 257/40
2009/0017331 A1*  1/2009 Iwakuma et al. ............. 428/690
2009/0200927 A1   8/2009 D'Andrade et al.
2010/0301744 A1  12/2010 Osaka et al.

FOREIGN PATENT DOCUMENTS

WO    WO 2009/030981 A2    3/2009

OTHER PUBLICATIONS

Koene, B.E. et al, "Asymmetric Triaryldiamines as Thermally Stable Hole Transporting Layers for Organic Light-Emitting Devices," Chemistry of Materials, vol. 10, No. 8, published on Web: Jul. 21, 1998, pp. 2235-2250.

(Continued)

*Primary Examiner* — J. L. Yang
(74) *Attorney, Agent, or Firm* — Husch Blackwell LLP

(57) ABSTRACT

A substance having a hole-transport, property and a wide band gap is provided. A heterocyclic compound represented by a general formula (G1) is provided. In the formula, $\alpha^1$ and $\alpha^2$ separately represent a substituted or unsubstituted arylene group having 6 to 13 carbon atoms; n and k separately represent 0 or 1; $Q^1$ and $Q^2$ separately represent sulfur or oxygen; and $R^1$ to $R^{22}$ separately represent hydrogen, an alkyl group having 1 to 12 carbon atoms, or a substituted or unsubstituted aryl group having 6 to 14 carbon atoms.

28 Claims, 18 Drawing Sheets

(56) References Cited

OTHER PUBLICATIONS

Goldsmith, C.R. et al., "C-H Bond Activation by a Ferric Methoxide Complex: Modeling the Rate-Determining Step in the Mechanism of Lipoxygenase," J. Am. Soc., vol. 124, No. 1, 2002, pp. 83-96.

Onishi, T. et al., "A Method of Measuring an Energy Level," *High Molecular EL Materials Development of Light-Emitting High Molecular Compounds,* Kyoritsu Shuppan, Dec. 25, 2004, p. 64-67 (with English translation, pp. 1-3).

\* cited by examiner

HETEROCYCLIC COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to a heterocyclic compound, a light-emitting element, a light-emitting device, an electronic device, and a lighting device.

2. Description of the Related Art

In recent years, research and development have been extensively conducted on light-emitting elements using electroluminescence (EL). In a basic structure of such a light-emitting element, a layer containing a light-emitting substance is interposed between a pair of electrodes. By applying voltage to this element, light emission from the light-emitting substance can be obtained.

Since such a light-emitting element is of self-light-emitting type, it is considered that the light-emitting element has advantages over a liquid crystal display in that visibility of pixels is high, backlight is not required, and so on and is therefore suitable as flat panel display elements. In addition, it is also a great advantage that the light-emitting element can be manufactured as a thin and lightweight element. Furthermore, very high speed response is also one of the features of such elements.

Furthermore, since such light-emitting elements can be formed in a film form, they make it possible to provide planar light emission. Therefore, large-area elements can be easily formed. This feature is difficult to obtain with point light sources typified by incandescent lamps and LEDs or linear light sources typified by fluorescent lamps. Thus, light-emitting elements also have great potential as planar light sources applicable to lighting devices and the like.

Such light-emitting elements utilizing EL can be broadly classified according to whether the light-emitting substance is an organic compound or an inorganic compound. In the case of an organic EL element in which a layer containing an organic compound used as the light-emitting substance is provided between a pair of electrodes, application of a voltage to the light-emitting element causes injection of electrons from the cathode and holes from the anode into the layer containing the organic compound having a light-emitting property, and thus a current flows. Light is emitted when the carriers (electrons and holes) are recombined and the organic compound returns to the ground state from the excited state where both the electrons and the holes are generated in organic molecules with a light-emitting property.

In improving element characteristics of such a light-emitting element, there are a lot of problems which depend on a substance, and in order to solve the problems, improvement of an element structure, development of a substance, and the like have been carried out.

A light-emitting element using organic EL has a plurality of layers, and a carrier-transport layer is generally provided between a light-emitting layer and an electrode. One of the reasons is that a carrier-transport layer can prevent energy transfer of excitation energy from the light-emitting layer to the electrode and occurrence of quenching. Further, a material (an exciton-blocking material) having higher excitation energy than a light-emitting layer is preferably used for a carrier-transport layer which is adjacent to the light-emitting layer so that excitation energy is not transferred from the light-emitting layer. In other words, a material having a wide band gap (Bg) between the highest occupied molecular orbital level (HOMO level) and the lowest unoccupied molecular orbital level (LUMO level) is considered preferable.

In a light-emitting element using organic EL, a carrier-transport layer provided between a light-emitting layer and an electrode may include a plurality of layers. One possible reason is to adjust a carrier-injection barrier between adjacent layers. It can be considered that with a higher injection barrier, carrier passage can be suppressed and this leads to more efficient recombination in the light-emitting layer.

In the case of an element which emits phosphorescence, excitation energy of a light-emitting substance would be lost unless the level of triplet excitation energy (T1 level) of a material in contact with the light-emitting substance is sufficiently higher than the T1 level of the light-emitting substance. Therefore, as a host material of a light-emitting layer of a phosphorescent light-emitting element or a material of a carrier-transport layer adjacent to the light-emitting layer, a material having a T1 level higher than that of a phosphorescent light-emitting material is used.

However, many of common materials having a wide band gap or a high T1 level have low molecular weights so as not to extend conjugation. Due to their low molecular weights, these materials have many problems such as significantly poor thermophysical properties (a low glass transition temperature (Tg), a strong tendency toward crystallization) and poor film quality. Therefore, a material which can overcome these problems as well as having a wide band gap and a high T1 level is desired.

For example, Reference 1 discloses 4,4'-bis[N-(1-naphthyl)-N-phenylamino]biphenyl (abbreviation: NPB) as a material which can be used for a hole-transport layer of a light-emitting element.

[Reference 1] Chem. Mater., 1998, 10, pp. 2235-2250

SUMMARY OF THE INVENTION

However, NPB has absorption in the visible region. Therefore, when NPB is used for a light-emitting element, there is a problem in that NPB absorbs part of visible light emitted from a light-emitting layer and decreases light extraction efficiency. In addition, because NPB does not have a sufficiently wide band gap and has a low LUMO level, electrons may pass through a light-emitting layer into an adjacent NPB layer. Furthermore, in some cases, carrier balance cannot be optimized, and a decrease in efficiency and a change in color may be caused. Moreover, excitation energy may be transferred from the light-emitting layer to the adjacent NPB layer, which may result in quenching.

Thus, it is an object of one embodiment of the present invention to provide a substance having a hole-transport property and a wide band gap.

It is another object of one embodiment of the present invention to provide a light-emitting element having high emission efficiency by application of the above substance to the light-emitting element. It is an object of one embodiment of the present invention to provide a light-emitting device including the light-emitting element, an electronic device including the light-emitting device, and a lighting device including the light-emitting device.

One embodiment of the present invention is a heterocyclic compound represented by a general formula (G1).

(G1)

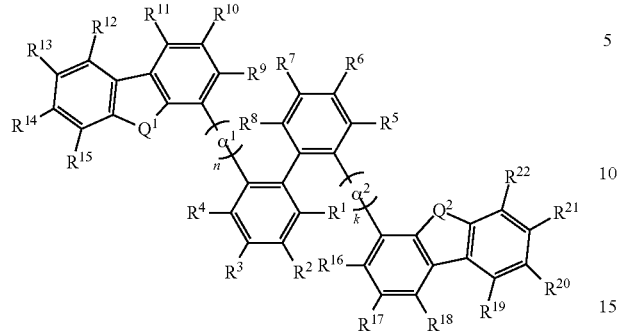

In the formula, $\alpha^1$ and $\alpha^2$ separately represent a substituted or unsubstituted arylene group having 6 to 13 carbon atoms; n and k separately represent 0 or 1; $Q^1$ and $Q^2$ separately represent sulfur or oxygen; and $R^1$ to $R^{22}$ separately represent hydrogen, an alkyl group having 1 to 12 carbon atoms, or a substituted or unsubstituted aryl group having 6 to 14 carbon atoms.

In the above-described heterocyclic compound, it is preferable that $R^1$ to $R^{22}$ be separately represented by any one of structural formulae (R-1) to (R-14).

 (R-1)

 (R-2)

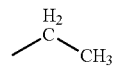 (R-3)

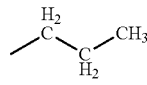 (R-4)

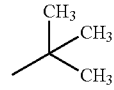 (R-5)

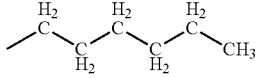 (R-6)

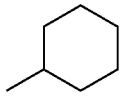 (R-7)

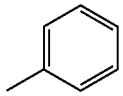 (R-8)

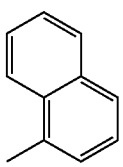 (R-9)

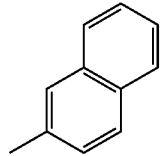 (R-10)

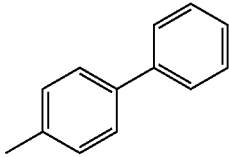 (R-11)

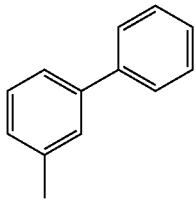 (R-12)

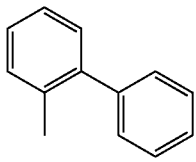 (R-13)

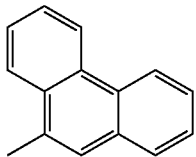 (R-14)

In the above-described heterocyclic compound, it is preferable that substituents of $\alpha^1$ and $\alpha^2$ be separately an alkyl group having 1 to 12 carbon atoms or an aryl group having 6 to 14 carbon atoms. It is particularly preferable that the substituents be represented by any one of the structural formulae (R-2) to (R-14).

 (R-1)

 (R-2)

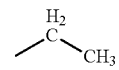 (R-3)

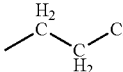 (R-4)

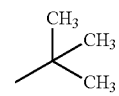 (R-5)

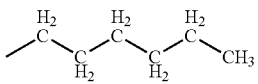 (R-6)

-continued
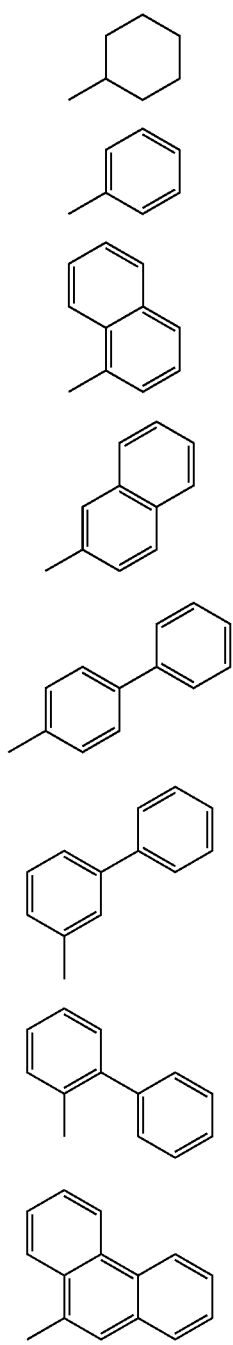
In the above-described heterocyclic compound, it is preferable that α¹ and α² be separately represented by any one of structural formulae (α-1) to (α-11).
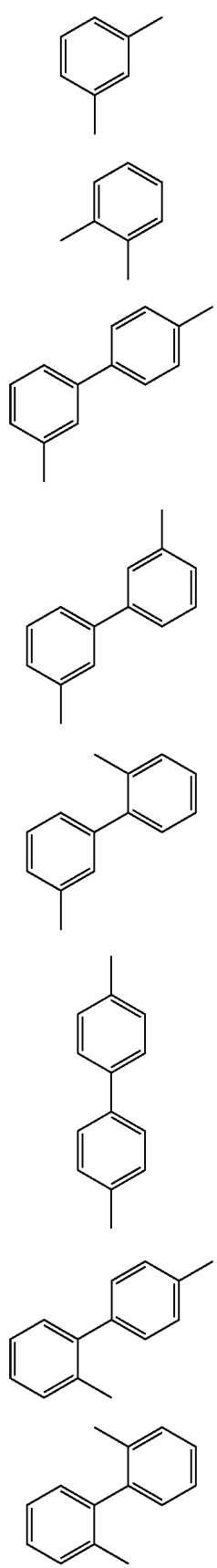

(α-10)

(α-11)

Another embodiment of the present invention is a light-emitting element including the above-described heterocyclic compound. High emission efficiency can be achieved by use of the above-described heterocyclic compound for a light-emitting element.

Another embodiment of the present invention is a light-emitting element having an anode, a cathode, a light-emitting layer between the anode and the cathode, and a layer including the above-described heterocyclic compound between the anode and the light-emitting layer.

In the above-described light-emitting element, the layer including the above-described heterocyclic compound may be in contact with the anode, or the layer including the above-described heterocyclic compound may be in contact with the light-emitting layer.

In particular, in the case where the layer including the above-described heterocyclic compound is in contact with the anode, it is preferable that the layer including the above-described heterocyclic compound further include a metal oxide, in particular, molybdenum oxide.

Another embodiment of the present invention is a light-emitting element having an anode, a cathode, and a light-emitting layer between the anode and the cathode, in which the light-emitting layer includes the above-described heterocyclic compound.

Another embodiment of the present invention is a light-emitting device including the above-described light-emitting element. Another embodiment of the present invention is an electronic device including the above-described light-emitting device. Another embodiment of the present invention is a lighting device including the above-described light-emitting device.

Note that the light-emitting device in this specification includes an image display device and a light source. In addition, the light-emitting device includes all the following modules: a module in which a connector, such as a flexible printed circuit (FPC), a tape automated bonding (TAB) tape, or a tape carrier package (TCP), is attached to a panel, a module in which a printed wiring board is provided at the end of a TAB tape or a TCP, and a module in which an integrated circuit (IC) is directly mounted on a light-emitting device by a chip-on-glass (COG) method.

According to one embodiment of the present invention, a substance having a hole-transport property and a wide band gap can be provided.

According to one embodiment of the present invention, a light-emitting element having high emission efficiency can be provided. Alternatively, a light-emitting element having a long lifetime can be provided. According to one embodiment of the present invention, a light-emitting device including the light-emitting element, an electronic device including the light-emitting device, and a lighting device including the light-emitting device can be provided.

DETAILED DESCRIPTION OF THE INVENTION

Figure 1A:
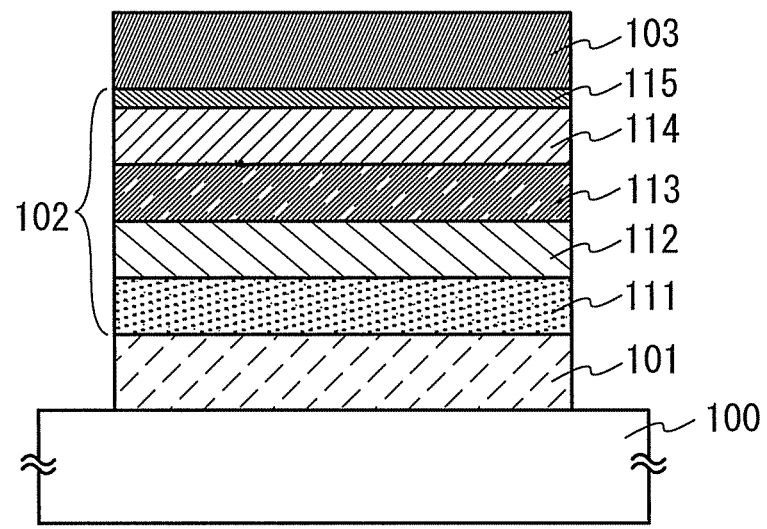
FIGS. 1A and 1B each illustrate a light-emitting element of one embodiment of the present invention.

Embodiments and examples will be described in detail with reference to the drawings. Note that the present invention is not limited to the following description and it will be readily appreciated by those skilled in the art that the modes and details of the present invention can be modified in various ways without departing from the spirit and scope thereof. Therefore, the present invention should not be interpreted as being limited to the description in the following embodiments and examples. Note that the same portions or portions having similar functions are commonly denoted by the same reference numerals in different drawings, and repetitive description thereof is omitted.

Embodiment 1

In this embodiment, a heterocyclic compound of one embodiment of the present invention will be described.

One embodiment of the present invention is a heterocyclic compound represented by the general formula (G1).

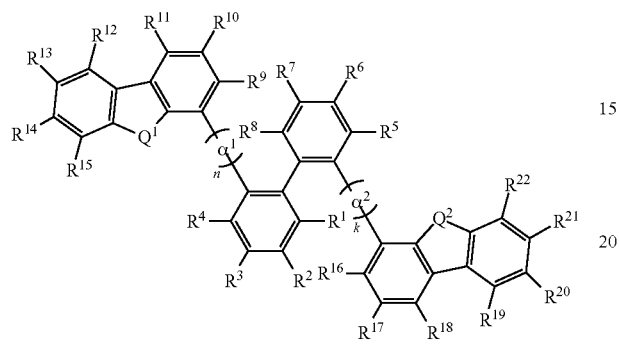
(G1)

In the general formula (G1), $\alpha^1$ and $\alpha^2$ separately represent a substituted or unsubstituted arylene group having 6 to 13 carbon atoms; n and k separately represent 0 or 1; $Q^1$ and $Q^2$ separately represent sulfur or oxygen; and $R^1$ to $R^{22}$ separately represent hydrogen, an alkyl group having 1 to 12 carbon atoms, or a substituted or unsubstituted aryl group having 6 to 14 carbon atoms.

In the general formula (G1), heterocyclic groups (groups including $Q^1$ or $Q^2$) are bonded to the 2-position and the 2'-position of a biphenyl skeleton. Therefore, a steric structure in which the heterocyclic groups are twisted with respect to the biphenyl skeleton is obtained. Therefore, conjugation of the heterocyclic group bonded to the 2-position of the biphenyl skeleton is unlikely to be extended to the heterocyclic group bonded to the 2'-position. Thus, the heterocyclic compound represented by the general formula (G1) can have a wide band gap as well as a high molecular weight, which is preferable (in the case where heterocyclic groups are bonded to the 4-position and the 4'-position, or the 3-position and the 3'-position, of the biphenyl skeleton, conjugation extends farther than in the case where they are bonded to the 2-position and the 2'-position).

In the above-described heterocyclic compound, it is preferable that $R^1$ to $R^{22}$ be separately represented by any one of structural formulae (R-1) to (R-14).

(R-1)
—H (R-2)
—CH₃

(R-3)
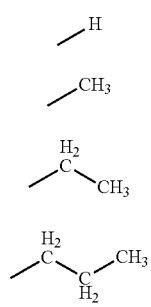

(R-4)

(R-5)
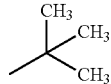

(R-6)
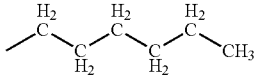

(R-7)
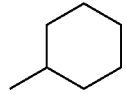

(R-8)
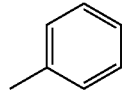

(R-9)
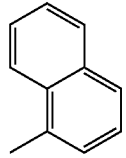

(R-10)
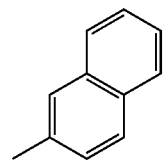

(R-11)
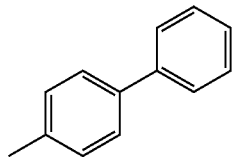

(R-12)
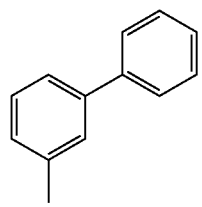

(R-13)
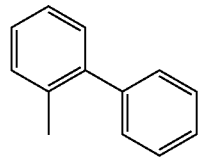

(R-14)
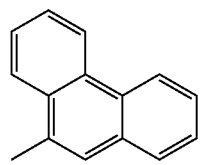

Examples of $R^1$ to $R^{22}$ are separately a methyl group, an ethyl group, a propyl group, a pentyl group, a hexyl group, a heptyl group, an octyl group, a nonyl group, a decyl group, a dodecyl group, a tridecyl group, a phenyl group, a biphenyl group, a naphthyl group, a phenanthryl group, and the like.

Among them, an alkyl group, a phenyl group, or a biphenyl group is preferable because a wide band gap can be obtained and a high T1 level or a high S1 level can be obtained. In addition, a naphthyl group or a phenanthryl group is preferable because it has a condensed ring and is capable of transporting more carries.

It is preferable that a substituent be provided at any position of $R^1$ to $R^{22}$ in the general formula (G1) because a material which is unlikely to be crystallized due to steric hindrance can be obtained. It is preferable that the substituent be an alkyl group as represented in the above structural formulae (R-2) to (R-6) because high solubility in an organic solvent can be obtained and easier purification and solution preparation can be achieved. It is preferable that the substituent be an alkyl group, or a phenyl group or a biphenyl group as represented in the above-described structural formulae (R-8) and (R-11) to (R-13) because a wide band gap can be obtained. It is preferable that the substituent be an aryl group as represented in the above-described structural formulae (R-8) to (R-14) because the carrier-transport property can be improved.

In particular, a heterocyclic compound having a substituent at the 2-position or the 8-position of a dibenzothiophene skeleton or a dibenzofuran skeleton (at the position of $R^{10}$, $R^{13}$, $R^{17}$, or $R^{20}$ in the general formula (G1)) is preferable because it can be easily synthesized. Note that in the case where the heterocyclic compound has a substituent, the number of synthetic steps may be increased and by-products or synthetic cost may be increased. In this respect, it is preferable that the heterocyclic compound do not have a substituent.

In the above-described heterocyclic compound, it is preferable that $\alpha^1$ and $\alpha^2$ separately represent a substituted or unsubstituted phenylene group, a substituted or unsubstituted biphenylenediyl group, or a substituted or unsubstituted naphthalenediyl group. A phenylene group or a biphenyldiyl group is particularly preferable because conjunction does not easily extend, a wide band gap can be obtained, absorption in the visible region is unlikely to be observed, and a high T1 level or a high S1 level can be obtained. A phenylene group or a biphenyldiyl group is particularly preferable for use in a light-emitting element which emits shorter wavelength light such as blue or green fluorescence. A phenylene group is preferable because the level of triplet excitation energy (T1 level) is higher. A phenylene group is particularly preferable for use in a light-emitting element which emits shorter wavelength light such as blue or green phosphorescence. Note that the triplet excitation energy refers to an energy difference between a ground state and a triplet excited state.

In the above-described heterocyclic compound, it is preferable that $\alpha^1$ and $\alpha^2$ be separately represented by any one of the structural formulae (α-1) to (α-11).

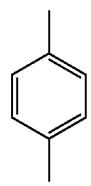
(α-1)

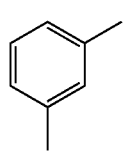
(α-2)

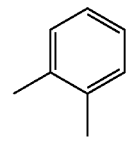
(α-3)

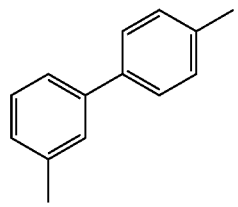
(α-4)

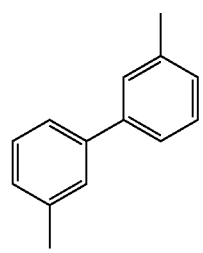
(α-5)

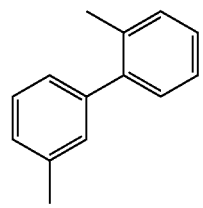
(α-6)

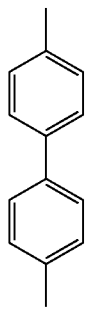
(α-7)

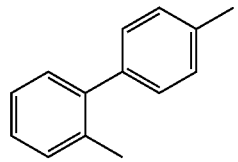
(α-8)

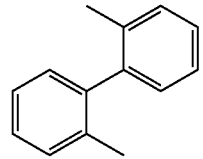
(α-9)

(α-10)

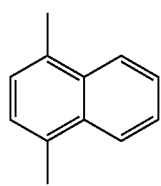

(α-11)

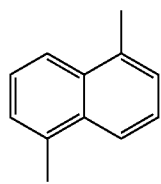

In the case where α¹ in the above-described heterocyclic compound has one or more substituents, it is preferable that the one or more substituents be separately an alkyl group having 1 to 12 carbon atoms or an aryl group having 6 to 14 carbon atoms. It is particularly preferable that the one or more substituents be represented by any one of the structural formulae (R-2) to (R-14).

In the case where α² in the above-described heterocyclic compound has one or more substituents, it is preferable that the one or more substituents be separately an alkyl group having 1 to 12 carbon atoms or an aryl group having 6 to 14 carbon atoms. It is particularly preferable that the one or more substituents be represented by any one of the structural formulae (R-2) to (R-14).

Examples of substituents of α¹ and α² are separately a methyl group, an ethyl group, a propyl group, a pentyl group, a hexyl group, a heptyl group, an octyl group, a nonyl group, a decyl group, a dodecyl group, a tridecyl group, a phenyl group, a biphenyl group, a naphthyl group, a phenanthryl group, and the like. Among these, an alkyl group, a phenyl group, or a biphenyl group is preferable because a wide band gap can be obtained.

Specific structural formulae of a heterocyclic compound of one embodiment of the present invention are given in the following structural formulae (100) to (115), (120) to (135), and (140) to (145). Note that the present invention is not limited to these structures.

(100)

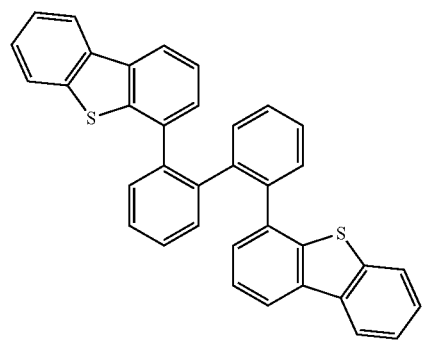

(101)

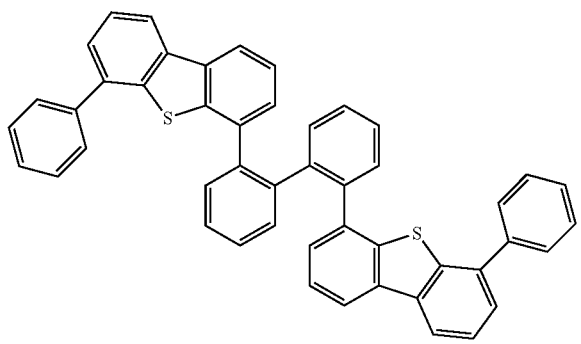

(102)

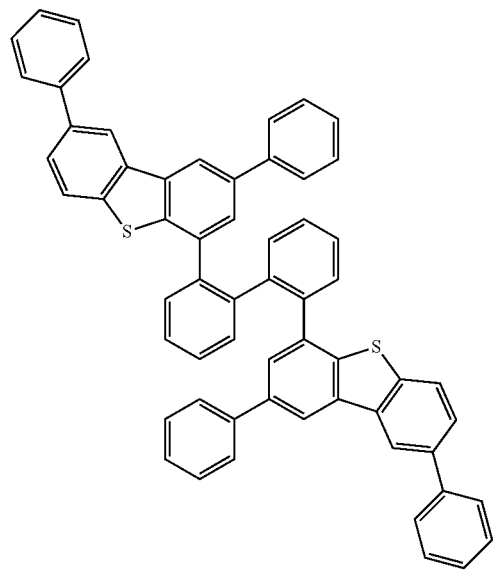

(103)

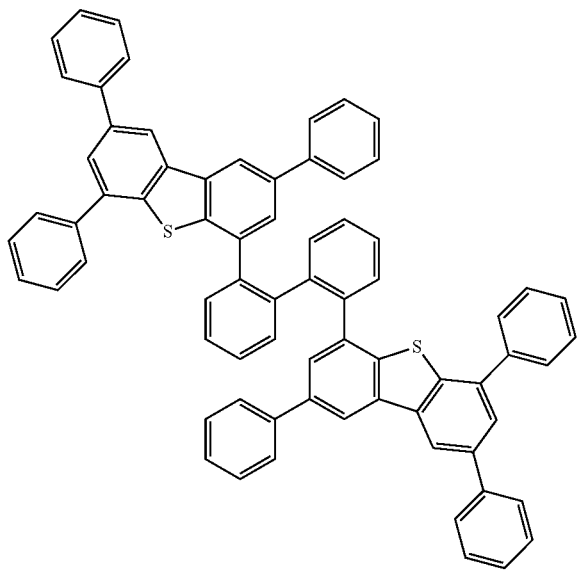

(104)
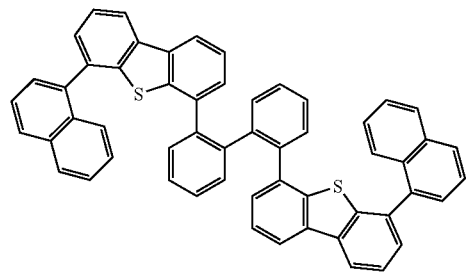
(105)
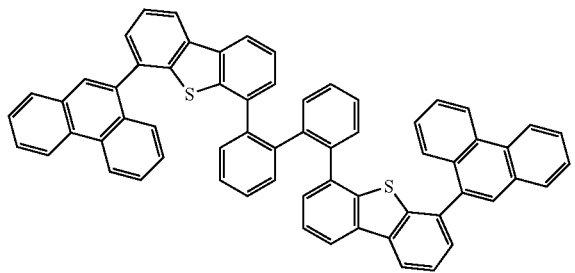
(106)
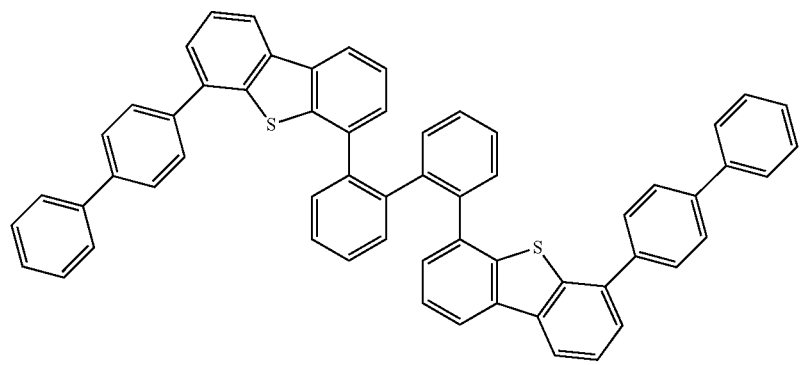
(107)
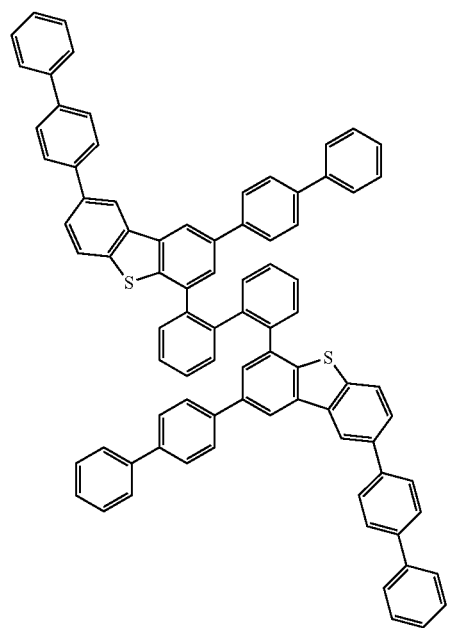
(108)

-continued
(109)
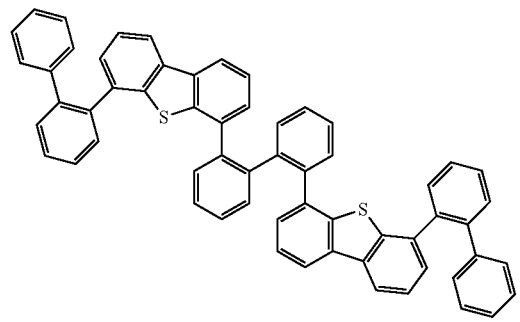
(110)
(111)
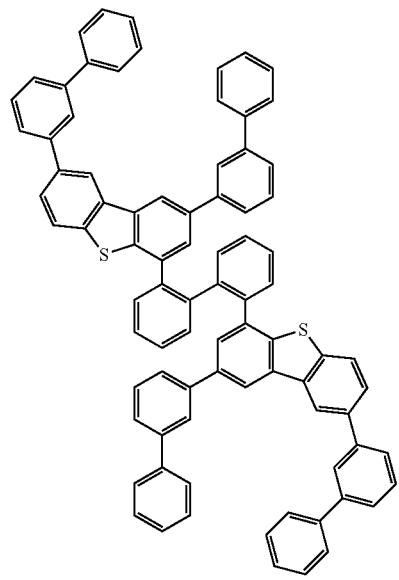
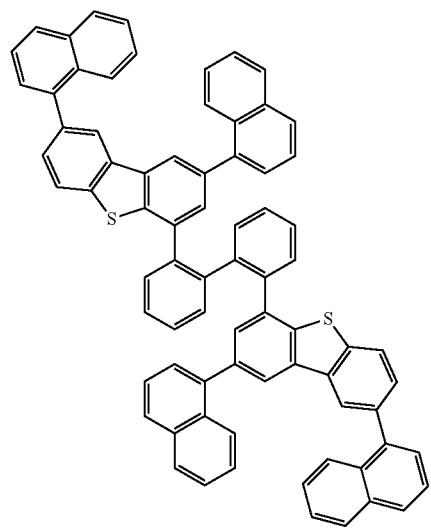
(112)
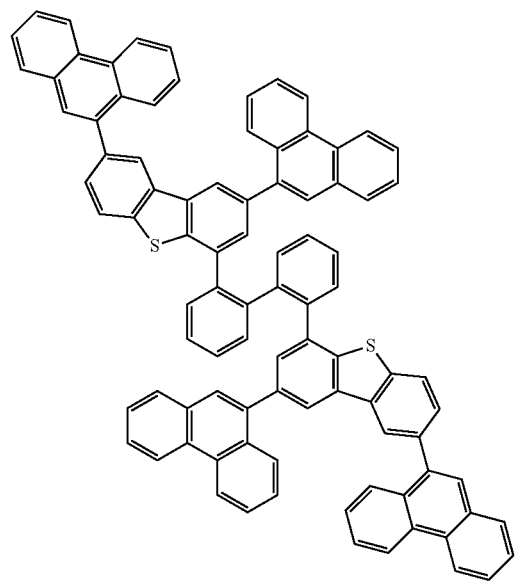

-continued
(113)
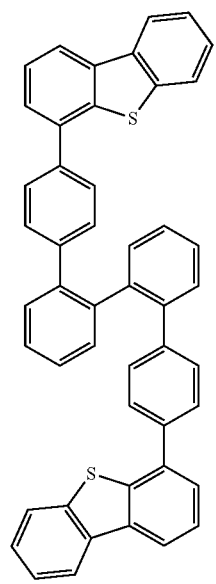
(114)
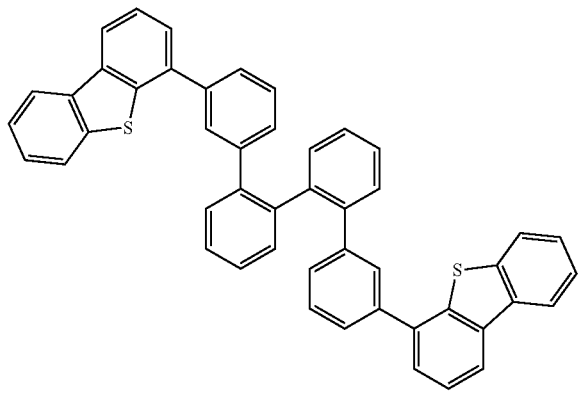
(115)
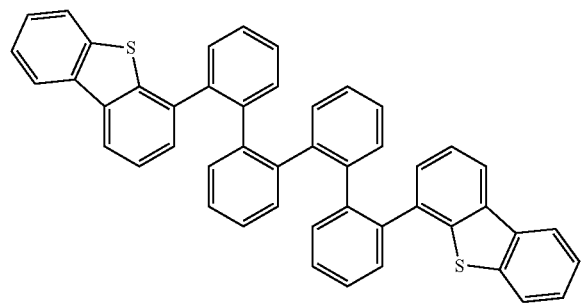
(120)
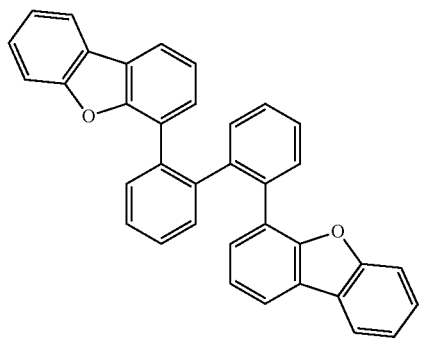
(121)
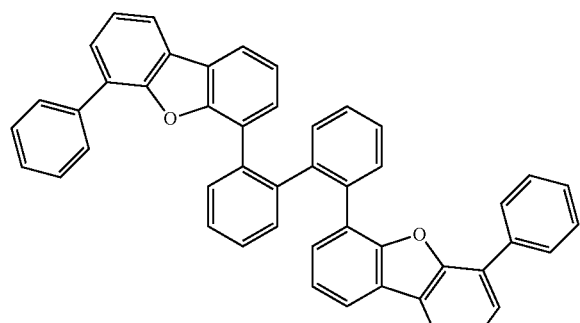
(122)
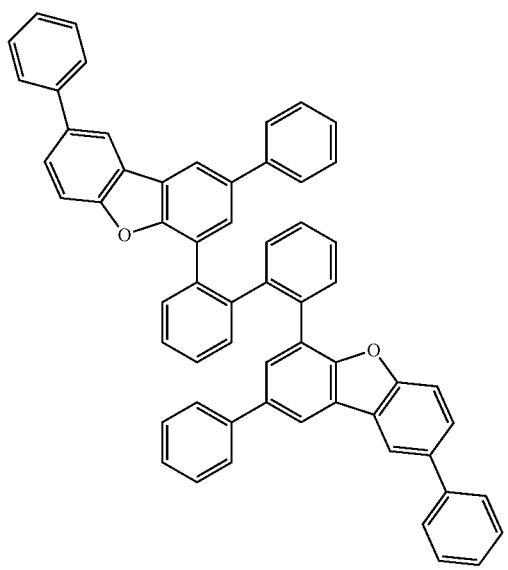

-continued
(123)
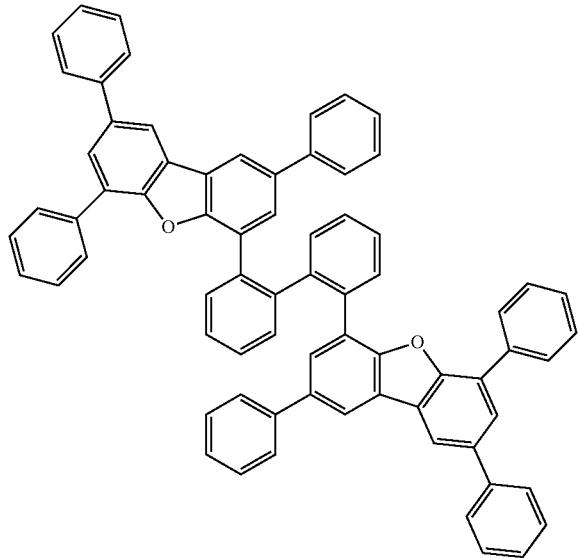
(124)
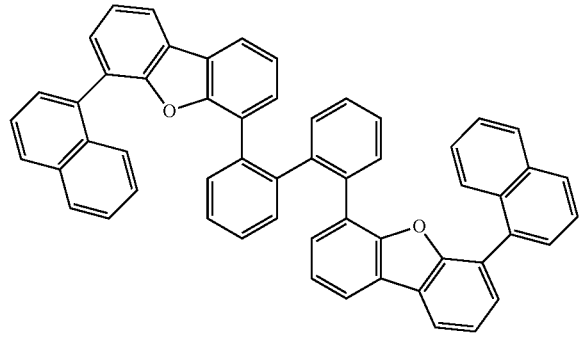
(125)
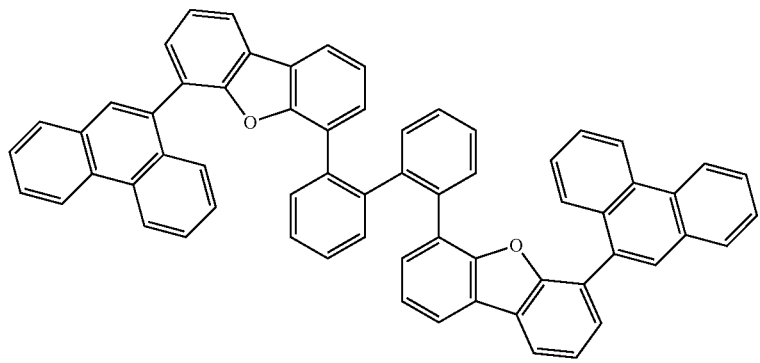
(126)
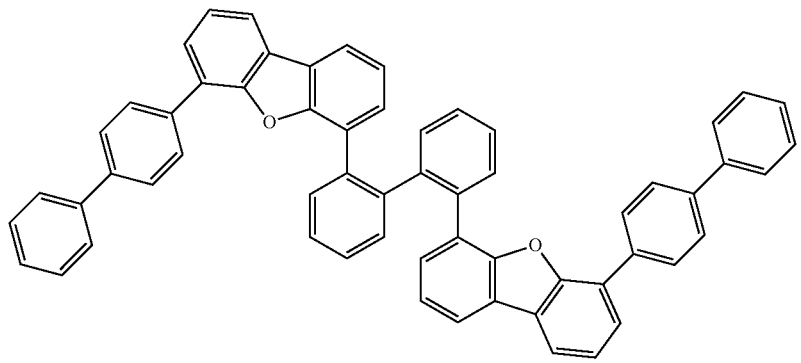

-continued
(127)
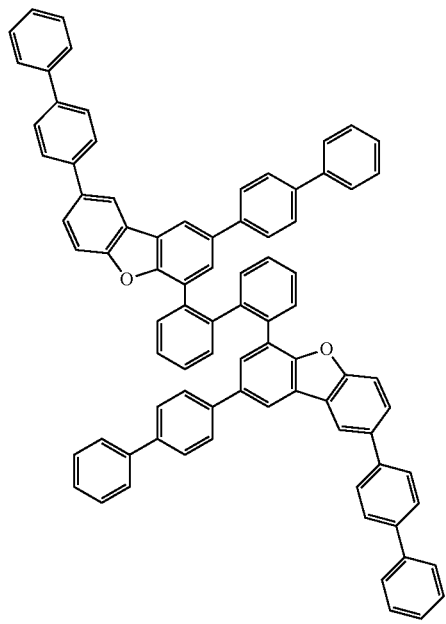
(128)
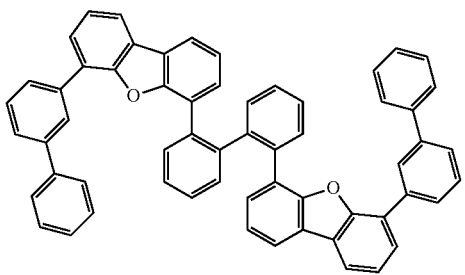
(129)
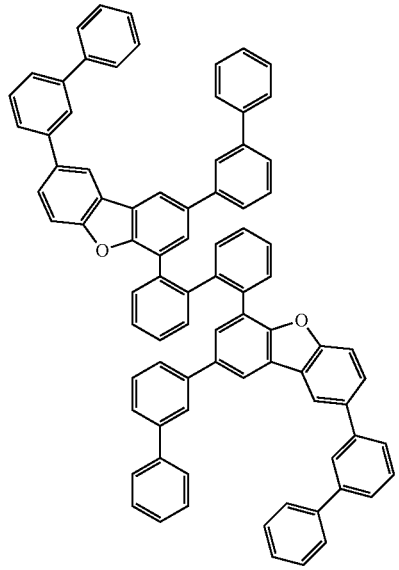
(130)
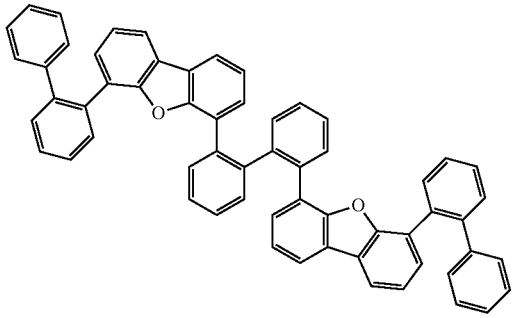

(131)
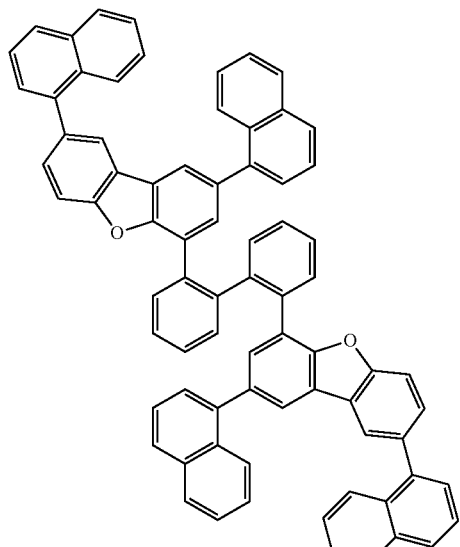
(132)
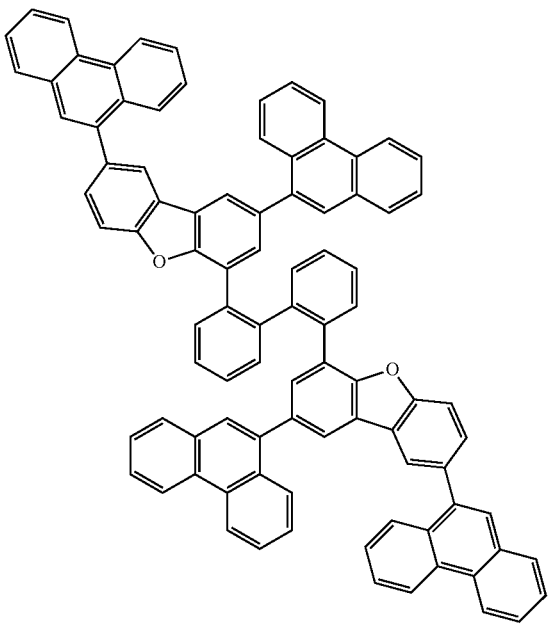
(133)
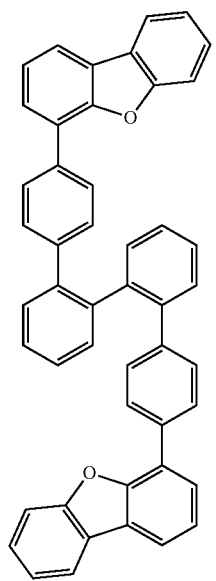
(134)
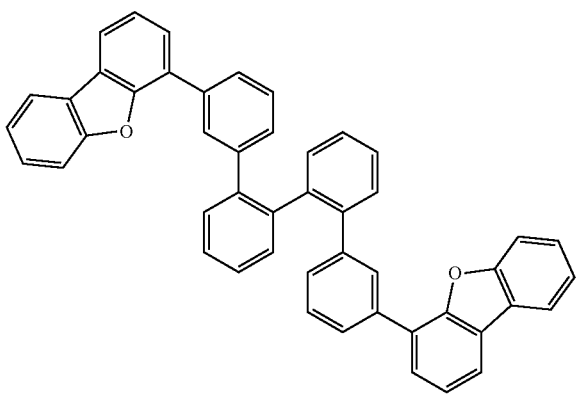

-continued
(135)
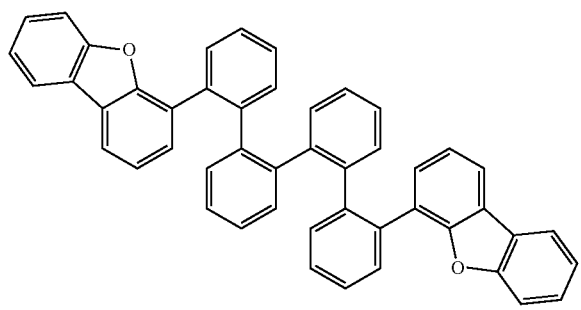
(140)
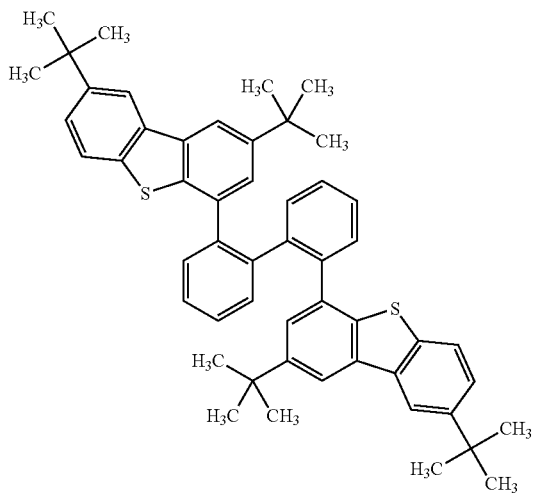
(141)
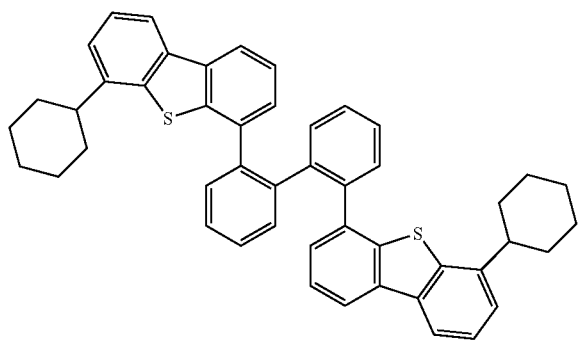
(142)
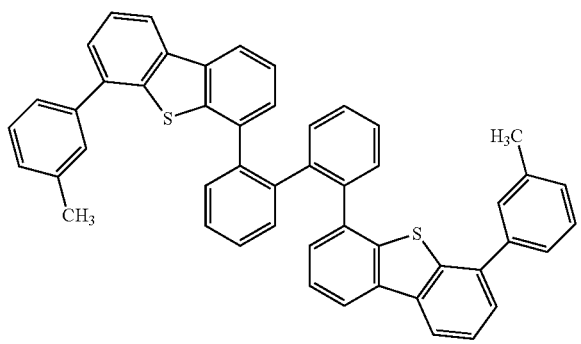
(143)
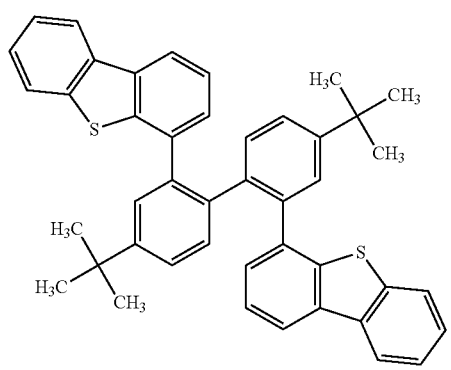
(144)
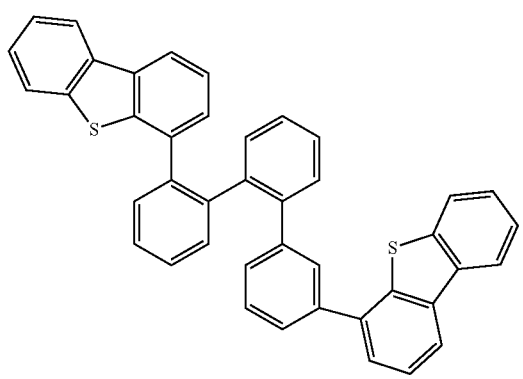
(145)
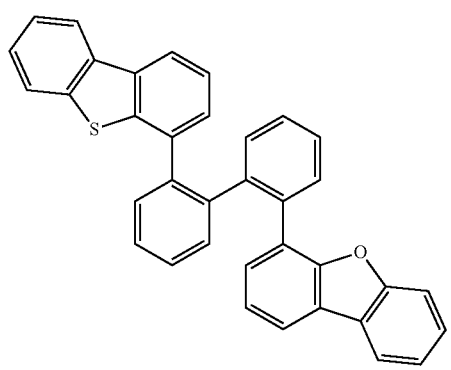

A variety of reactions can be applied to a method of synthesizing a heterocyclic compound of one embodiment of the present invention. For example, the heterocyclic compound of one embodiment of the present invention, represented by the general formula (G1), can be synthesized by synthesis methods described below. Note that a method of synthesizing a heterocyclic compound of one embodiment of the present invention is not limited to the synthesis methods described below.

《Method of Synthesizing Heterocyclic Compound Represented by General Formula (G1)》

An example of a method of synthesizing the heterocyclic compound represented by the following general formula (G1) will be described.

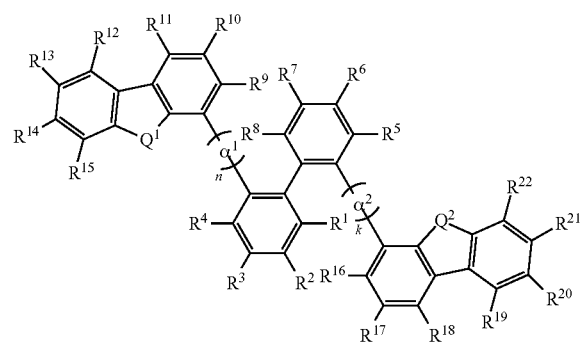

(G1)

In the general formula (G1), $\alpha^1$ and $\alpha^2$ separately represent a substituted or unsubstituted arylene group having 6 to 13 carbon atoms; n and k separately represent 0 or 1; $Q^1$ and $Q^2$ separately represent sulfur or oxygen; and $R^1$ to $R^{22}$ separately represent hydrogen, an alkyl group having 1 to 12 carbon atoms, or a substituted or unsubstituted aryl group having 6 to 14 carbon atoms.

⟨Step 1⟩

As illustrated in the following synthesis scheme (A-1), a heterocyclic boron compound (a1) and a dihalide compound (a2) are coupled, whereby a heterocyclic halide compound (a3) can be obtained.

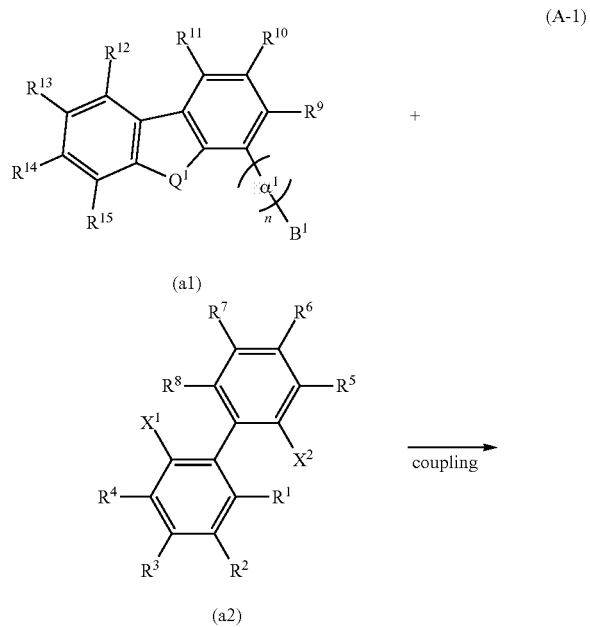

(A-1)

(a1)

(a2)

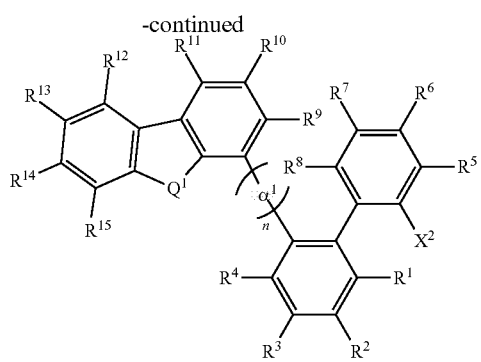

(a3)

In the synthesis scheme (A-1), $\alpha^1$ represents a substituted or unsubstituted arylene group having 6 to 13 carbon atoms; n represents 0 or 1; $Q^1$ represents sulfur or oxygen; $R^1$ to $R^{15}$ separately represent hydrogen, an alkyl group having 1 to 12 carbon atoms, or a substituted or unsubstituted aryl group having 6 to 14 carbon atoms; and $X^1$ and $X^2$ represent a halogen. $X^1$ and $X^2$ preferably represent bromine or iodine, which has high reactivity, more preferably iodine. In the case of selectively reacting $B^1$ and $X^1$, it is preferable to use as $X^1$ a halogen which has higher reactivity than $X^2$ (reactivity: iodine>bromine>chlorine). $B^1$ represents a boronic acid or dialkoxyboron.

Note that there are a variety of reaction conditions for the coupling reaction in the synthesis scheme (A-1). As an example, a synthesis method using a metal catalyst in the presence of a base can be employed.

The case where a Suzuki-Miyaura reaction is performed in the synthesis scheme (A-1) is described. A palladium catalyst can be used as the metal catalyst, and a mixture of a palladium complex and a ligand thereof can be used as the palladium catalyst. As the palladium complex, palladium(II)acetate, tetrakis(triphenylphosphine)palladium(0), bis(triphenylphosphine)palladium(II)dichloride, and the like can be given. As the ligand, tri(ortho-tolyl)phosphine, triphenylphosphine, tricyclohexylphosphine, and the like can be given. As a substance which can be used as the base, an organic base such as sodium tert-butoxide, an inorganic base such as potassium carbonate, and the like can be given.

The reaction is preferably performed in a solution. Examples of a solvent that can be used are, but not limited to, the following solvents: a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and the like. However, the catalyst, base, and solvent which can be used are not limited thereto. Alternatively, in the scheme, an organoboron compound of an aryl derivative, aryl aluminum, aryl zirconium, aryl zinc, aryl tin compound, or the like may be used instead of an arylboronic acid. In addition, the reaction is preferably performed under an inert atmosphere of nitrogen, argon, or the like.

⟨Step 2⟩

Next, as illustrated in the following synthesis scheme (A-2), the heterocyclic halide compound (a3) and a heterocyclic boron compound (a4) are coupled, whereby the heterocyclic compound represented by the general formula (G1) can be obtained.

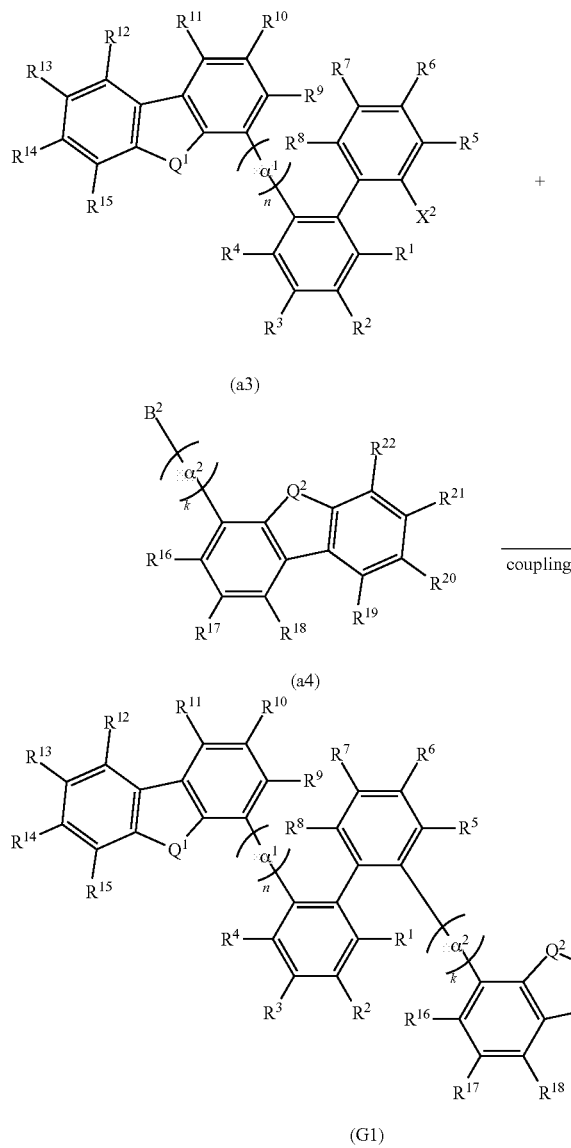

In the synthesis scheme (A-2), $\alpha^1$ and $\alpha^2$ separately represent a substituted or unsubstituted arylene group having 6 to 13 carbon atoms; n and k separately represent 0 or 1; $Q^1$ and $Q^2$ separately represent sulfur or oxygen; $R^1$ to $R^{22}$ separately represent hydrogen, an alkyl group having 1 to 12 carbon atoms, or a substituted or unsubstituted aryl group having 6 to 14 carbon atoms; and $B^2$ represents a boronic acid or dialkoxyboron.

There are a variety of reaction conditions for the coupling reaction in the synthesis scheme (A-2). As an example, a synthesis method using a metal catalyst in the presence of a base can be employed. The synthesis can be performed in a manner similar to the synthesis scheme (A-1); thus, the synthesis scheme (A-1) can be referred to for details.

In the case where the compound (a1) and the compound (a4) in the synthesis schemes (A-1) and (A-2) are identical except $B^1$ and $B^2$, the heterocyclic compound represented by the above general formula (G1) can be obtained by combining the compound (a1) and the compound (a4) with the compound (a2) at the same time. This is more preferable because it is simpler.

Thus, the heterocyclic compound of this embodiment can be synthesized.

The above-described heterocyclic compound of one embodiment of the present invention has a high hole-transport property. The heterocyclic compound of one embodiment of the present invention has a low HOMO level. The heterocyclic compound of one embodiment of the present invention has a high LUMO level. The heterocyclic compound of one embodiment of the present invention has a wide band gap. The heterocyclic compound of one embodiment of the present invention has a high T1 level.

Therefore, the heterocyclic compound of one embodiment of the present invention can be favorably used for a light-emitting element, and is particularly preferable for use for a hole-transport layer of a light-emitting element. A composite material formed by combining the heterocyclic compound of one embodiment of the present invention and an electron acceptor (an acceptor) can be used for a hole-injection layer of a light-emitting element.

This embodiment can be implemented in appropriate combination with any of the other embodiments.

Embodiment 2

In this embodiment, a light-emitting element of one embodiment of the present invention, which includes the heterocyclic compound described in Embodiment 1 for a hole-transport layer, will be described with reference to FIGS. 1A and 1B.

In a light-emitting element of this embodiment, an EL layer having at least a hole-transport layer and a light-emitting layer is interposed between a pair of electrodes. The EL layer may have a plurality of layers in addition to the hole-transport layer and the light-emitting layer. The plurality of layers has a structure in which a layer containing a substance having a high carrier-injection property and a layer containing a substance having a high carrier-transport property are combined and stacked so that a light-emitting region is formed in a region away from the electrodes, that is, so that carriers recombine in a region away from the electrodes. The plurality of layers may include, for example, a hole-injection layer, an electron-injection layer, an electron-transport layer, and the like.

In the light-emitting element of this embodiment illustrated in FIG. 1A, an EL layer 102 having a hole-transport layer 112 and a light-emitting layer 113 is provided between a pair of electrodes, a first electrode 101 and a second electrode 103. The EL layer 102 includes a hole-injection layer 111, the hole-transport layer 112, the light-emitting layer 113, an electron-transport layer 114, and an electron-injection layer 115. The light-emitting element in FIG. 1A includes the first electrode 101 formed over a substrate 100, the hole-injection layer 111, the hole-transport layer 112, the light-emitting layer 113, the electron-transport layer 114, and the electron-injection layer 115 which are stacked over the first electrode 101 in this order, and the second electrode 103 provided thereover. Note that, in a light-emitting element described in this embodiment, the first electrode 101 functions as an anode and the second electrode 103 functions as a cathode.

The substrate 100 is used as a support of the light-emitting element. For the substrate 100, for example, glass, quartz, plastic, or the like can be used. A flexible substrate can also be used. The flexible substrate is a substrate that can be bent, such as a plastic substrate made of polycarbonate, polyarylate, or polyether sulfone, for example. A film (made of polypropylene, polyester, vinyl, polyvinyl fluoride, vinyl chloride, or the like), an inorganic film formed by evaporation, or the like can also be used. Note that materials other than these can be used as long as they can function as a support of the light-emitting element.

For the first electrode 101, any of metals, alloys, conductive compounds, mixtures thereof, and the like which has a high work function (specifically, a work function of 4.0 eV or more) is preferably used. Specific examples include indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like. Films of these conductive metal oxides are usually found by sputtering, but may be formed by application of a sol-gel method or the like. For example, an IZO film can be formed by a sputtering method using a target obtained by adding 1 wt % to 20 wt % of zinc oxide to indium oxide. Further, an IWZO film can be formed by a sputtering method using a target obtained by adding 0.5 wt % to 5 wt % of tungsten oxide and 0.1 wt % to 1 wt % of zinc oxide to indium oxide. Other examples are gold, platinum, nickel, tungsten, chromium, molybdenum, iron, cobalt, copper, palladium, nitrides of metal materials (e.g., titanium nitride), and the like.

Note that when a layer included in the EL layer 102 and formed in contact with the first electrode 101 is formed using a later-described composite material formed by combining an organic compound and an electron acceptor (an acceptor), as a substance used for the first electrode 101, any of a variety of metals, alloys, and electrically conductive compounds, a mixture thereof, and the like can be used regardless of the work function; for example, aluminum, silver, an alloy containing aluminum (e.g., Al—Si), or the like can also be used.

The EL layer 102 formed over the first electrode 101 has at least the hole-transport layer 112 and the light-emitting layer 113, and the hole-transport layer 112 includes a heterocyclic compound which is one embodiment of the present invention. For part of the EL layer 102, a known substance can be used, and either a low molecular compound or a high molecular compound can be used. Note that substances forming the EL layer 102 may consist of organic compounds or may include an inorganic compound as a part.

Figure 1B:
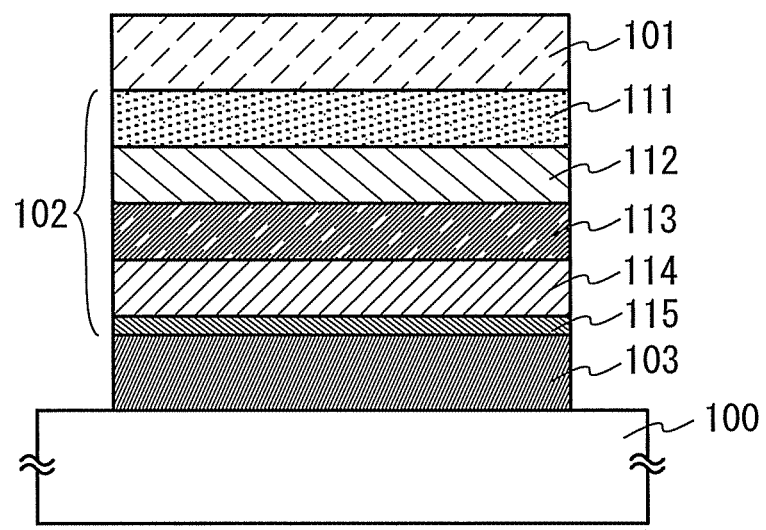

Further, as illustrated in FIGS. 1A and 1B, the EL layer 102 is formed by stacking an appropriate combination of the hole-injection layer 111, the electron-transport layer 114, the electron-injection layer 115, and the like in addition to the hole-transport layer 112 and the light-emitting layer 113.

The hole-injection layer 111 is a layer containing a substance having a high hole-injection property. Examples of a substance having a high hole-injection property which can be used are metal oxides, such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide. Other examples of a substance that can be used are phthalocyanine-based compounds, such as phthalocyanine (abbreviation: $H_2Pc$) and copper(II) phthalocyanine (abbreviation: CuPc).

Other examples of a substance that can be used are aromatic amine compounds which are low molecular organic compounds, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Still other examples of a substance that can be used are high molecular compounds (e.g., oligomers, dendrimers, and polymers), such as poly(N-vinylcarbazole) (abbreviation: PVK), poly(-vinyltriphenylamine) (abbreviation: PVTPA), poly[N-(4-{N'-[4-(4-diphenylamino)phenyl]phenyl-N-phenylamino}phenyl)methacrylamide] (abbreviation: PTPDMA), and poly[N,N'-bis(4-butylphenyl)-N,N'-bis(phenyl)benzidine] (abbreviation: Poly-TPD), and high molecular compounds to which acid is added, such as poly(3,4-ethylenedioxythiophene)/poly(styrenesulfonic acid) (PEDOT/PSS), or polyaniline/poly(styrenesulfonic acid) (PAni/PSS).

For the hole-injection layer 111, the composite material formed by combining an organic compound and an electron acceptor (an acceptor) may be used. Such a composite material, in which holes are generated in the organic compound by the electron acceptor, has high hole-injection and hole-transport properties. In this case, the organic compound is preferably a material excellent in transporting the generated holes (a substance having a high hole-transport property).

Examples of the organic compound used for the composite material are a variety of compounds, such as aromatic amine compounds, carbazole derivatives, aromatic hydrocarbons, and high molecular compounds (e.g., oligomers, dendrimers, and polymers). The organic compound used for the composite material is preferably an organic compound having a high hole-transport property, and specifically preferably a substance having a hole mobility of $10^{-6}$ cm$^2$/Vs or more. Note that other than these substances, any substance that has a property of transporting more holes than electrons may be used. Organic compounds that can be used for the composite material will be specifically described below.

A heterocyclic compound of one embodiment of the present invention is an organic compound having a high hole-transport property, and thus can be favorably used for the composite material. Other examples of an organic compound that can be used for the composite material are aromatic amine compounds, such as TDATA, MTDATA, DPAB, DNTPD, DPA3B, PCzPCA1, PCzPCA2, PCzPCN1,4,4'-bis [N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4-phenyl-4'-(9-phenylfluoren-9-yl)triphenylamine (abbreviation: BPAFLP), and carbazole derivatives, such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl]-2,3,5,6-tetraphenylbenzene.

Other examples of an organic compound that can be used are aromatic hydrocarbon compounds, such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, and 2,3,6,7-tetramethyl-9,10-di(1-naphthyl)anthracene.

Other examples of an organic compound that can be used are aromatic hydrocarbon compounds, such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9, 9'-bianthryl, anthracene, tetracene, rubrene, perylene, 2,5,8, 11-tetra(tert-butyl)perylene, pentacene, coronene, 4,4'-bis(2, 2-diphenylvinyl)biphenyl (abbreviation: DPVBi), and 9,10-bis[4-(2,2-diphenylvinyl)phenyl]anthracene (abbreviation: DPVPA).

Further, examples of the electron acceptor are organic compounds, such as 7,7,8,8-tetracyano-2,3,5,6-tetrafluoroquinodimethane (abbreviation: F$_4$-TCNQ) and chloranil, oxides of transition metals, and oxides of metals that belong to Groups 4 to 8 in the periodic table, and the like. Specific preferred examples include vanadium oxide, niobium oxide, tantalum oxide, chromium oxide, molybdenum oxide, tungsten oxide, manganese oxide, and rhenium oxide because their electron-acceptor properties are high. Among these, molybdenum oxide is especially preferable since it is stable in the air, has low hygroscopic property, and is easily treated.

The composite material may be formed using the above-described electron acceptor and the above-described high molecular compound such as PVK, PVTPA, PTPDMA, or Poly-TPD, and may be used for the hole-injection layer 111.

The hole-transport layer 112 is a layer that contains a substance having a high hole-transport property. The hole-transport layer 112 of this embodiment includes a heterocyclic compound of one embodiment of the present invention.

The light-emitting layer 113 is a layer including a light-emitting substance. As the light-emitting substance, for example, a fluorescent compound, which emits fluorescence, or a phosphorescent compound, which emits phosphorescence, can be used.

A heterocyclic compound of one embodiment of the present invention is a material which emits fluorescence, and thus can be used as the light-emitting substance.

As a fluorescent compound that can be used for the light-emitting layer 113, the following light-emitting materials can be given, for example: materials that emit blue light, such as N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and 4-(10-phenyl-9-anthryl)-4'-(9-phenyl-9H-carbazol-3-yl)triphenylamine (abbreviation: PCBAPA); materials that emit green light, such as N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), and N,N,9-triphenylanthracen-9-amine (abbreviation: DPhAPhA); materials that emit yellow light, such as rubrene and 5,12-bis(1,1'-biphenyl-4-yl)-6,11-diphenyltetracene (abbreviation: BPT); and materials that emit red light, such as N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-a]fluoranthene-3,10-d iamine (abbreviation: p-mPhAFD).

As a phosphorescent compound that can be used for the light-emitting layer 113, the following light-emitting materials can be given, for example: materials that emit blue light, such as bis[2-(4',6'-difluorophenyl)pyridinato-N,C$^{2'}$]iridium (III)tetrakis(1-pyrazolyl)borate (abbreviation: FIr6), bis[2-(4',6'-difluorophenyl)pyridinato-N,C$^{2'}$]iridium(III)picolinate (abbreviation: FIrpic), bis{2-[3',5'-bis(trifluoromethyl)phenyl]pyridinato-N,C$^{2'}$}iridium(III)picolinate (abbreviation: Ir(CF$_3$ppy)$_2$(pic)), and bis[2-(4',6'-difluorophenyl)pyridinato-N,C$^{2'}$]iridium(III)acetylacetonate (abbreviation: FIr(acac)); materials that emit green light, such as tris(2-phenylpyridinato-N,C$^{2'}$)iridium(III) (abbreviation: Ir(ppy)$_3$), bis(2-phenylpyridinato-N,C$^{2'}$)iridium(III)acetylacetonate (abbreviation: Ir(ppy)$_2$(acac)), bis(1,2-diphenyl-1H-benzimidazolato)iridium(III)acetylacetonate (abbreviation: Ir(pbi)$_2$(acac)), bis(benzo[h]quinolinato)iridium(III)acetylacetonate (abbreviation: Ir(bzq)$_2$(acac)), and tris(benzo[h]quinolinato)iridium(III) (abbreviation: Ir(bzq)$_3$); materials that emit yellow light, such as bis(2,4-diphenyl-1,3-oxazolato-N,C$^{2'}$)iridium(III)acetylacetonate (abbreviation: Ir(dpo)$_2$(acac)), bis[2-(4'-(perfluorophenylphenyl)pyridinato]iridium(III)acetylacetonate (abbreviation: Ir(p-PF-ph)$_2$ (acac)), bis(2-phenylbenzothiazolato-N,C$^{2'}$)iridium(III) acetylacetonate (abbreviation: Ir(bt)$_2$(acac)), (acetylacetonato)bis[2,3-bis(4-fluorophenyl)-5-methylpyrazinato]iridium(III) (abbreviation: Ir(Fdppr-Me)$_2$ (acac)), and (acetylacetonato)bis{2-(4-methoxyphenyl)-3,5-dimethylpyrazinato}iridium(III) (abbreviation: Ir(dmmoppr)$_2$(acac)); materials that emit orange light, such as tris(2-phenylquinolinato-N,C$^{2'}$)iridium(III) (abbreviation: Ir(pq)$_3$), bis(2-phenylquinolinato-N,C$^{2'}$)iridium(III)acetylacetonate (abbreviation: Ir(pq)$_2$(acac)), (acetylacetonato)bis(3,5-dimethyl-2-phenylpyrazinato)iridium(III) (abbreviation: Ir(mppr-Me)$_2$(acac)), and (acetylacetonato)bis(5-isopropyl-3-methyl-2-phenylpyrazinato)iridium(III) (abbreviation: Ir(mppr-iPr)$_2$(acac)); and materials that emit red light, for example, organometallic complexes, such as bis[2-(2'-benzo[4,5-α]thienyl)pyridinato-N,C$^{3'}$)iridium(III)acetylacetonate (abbreviation: Ir(btp)$_2$(acac)), bis(1-phenylisoquinolinato-N,C$^{2'}$)iridium(III)acetylacetonate (abbreviation: Ir(piq)$_2$(acac), (acetylacetonato)bis[2,3-bis(4-fluorophenyl)quinoxalinato]iridium(III) (abbreviation: Ir(Fdpq)$_2$(acac)), (acetylacetonato)bis(2,3,5-triphenylpyrazinato)iridium(III) (abbreviation: Ir(tppr)$_2$(acac)), (dipivaloylmethanato)bis(2,3,5-triphenylpyrazinato)iridium(III) (abbreviation: Ir(tppr)$_2$(dpm)), and (2,3,7,8,12,13,17,18-octaethyl-21H,23H-porphyrin)platinum(II) (abbreviation: PtOEP). Any of the following rare-earth metal complexes can be used as a phosphorescent compound: tris(acetylacetonato)(monophenanthroline)terbium(III) (abbreviation: Tb(acac)$_3$(Phen)); tris(1,3-diphenyl-1,3-propanedionato)(monophenanthroline) europium(III) (abbreviation: Eu(DBM)$_3$(Phen)); and tris[1-(2-thenoyl)-3,3,3-trifluoroacetonato](monophenanthroline) europium(III) (abbreviation: Eu(TTA)$_3$(Phen)), because their light emission is from a rare-earth metal ion (electronic transition between different multiplicities) in such a rare-earth metal complex.

As the light-emitting substance, a high molecular compound can be used. Specifically, the following light-emitting materials can be given, for example: materials that emit blue light, such as poly(9,9-dioctylfluorene-2,7-diyl) (abbreviation: PFO), poly[(9,9-dioctylfluorene-2,7-diyl)-co-(2,5-dimethoxybenzene-1,4-diyl)] (abbreviation: PF-DMOP), and poly{(9,9-dioctylfluorene-2,7-diyl)-co-[N,N'-di-(p-butylphenyl)-1,4-diaminobenzene]} (abbreviation: TAB-PFH); materials that emit green light, such as poly(p-phenylenevinylene) (abbreviation: PPV), poly[(9,9-dihexylfluorene-2,7-diyl)-alt-co-(benzo[2,1,3]thiadiazole-4,7-diyl)] (abbreviation: PFBT), and poly[(9,9-dioctyl-2,7-divinylenefluorenylene)-alt-co-(2-methoxy-5-(2-ethylhexyloxy)-1,4-phenylene)]; and materials that emit orange to red light, such as poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-dihexyl-2,7-bis(1-cyanovinylene)fluorenylene]-alt-co-[2,5-bis(N,N'-diphenyl amino)-1,4-phenylene]}, and poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD).

Note that the light-emitting layer 113 may have a structure in which any of the above-described light-emitting substances (guest material) is dispersed into another substance (host material). A variety of substances can be used as the host material, and it is preferable to use a substance having a LUMO level higher than that of a light-emitting substance and having a HOMO level lower than that of the light-emitting substance.

A heterocyclic compound of one embodiment of the present invention is a substance having a high LUMO level and a low HOMO level, and thus can be favorably used as the host material.

In the case where the light-emitting substance is a phosphorescent compound, a host material thereof is preferably a substance having a T1 level higher than that of the light-emitting substance. A heterocyclic compound of one embodiment of the present invention is a substance having a high T1 level, and thus can be favorably used as a host material of a phosphorescent light-emitting substance.

In the case where the light-emitting substance is a fluorescent compound, a host material thereof is preferably a substance having a level of singlet excitation energy (S1 level) higher than that of the light-emitting substance. A heterocyclic compound of one embodiment of the present invention is a substance having a high S1 level, and thus can be favorably used as a host material of a fluorescent light-emitting substance.

Other specific examples of the host material that can be used are the following materials: metal complexes, such as tris(8-quinolinolato)aluminum(III) (abbreviation: Alq), tris(4-methyl-8-quinolinolato)aluminum(III) (abbreviation: Almq$_3$), bis(10-hydroxybenzo quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds, such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2'-(1,3,5-benzenetriyl)tris(1-phenyl-1H-benzimidazole) (abbreviation: TPBI), bathophenanthroline (abbreviation: BPhen), and bathocuproine (BCP); condensed aromatic compounds, such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl) diphenanthrene (abbreviation: DPNS2), 3,3',3"-(benzene-1,3,5-triyl)tripyrene (abbreviation: TPB3), 9,10-diphenylanthracene (abbreviation: DPAnth), and 6,12-dimethoxy-5,11-diphenylchrysene; aromatic amine compounds, such as N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), NPB (or α-NPD), TPD, DFLDPBi, and BSPB; and the like.

Plural kinds of host materials can also be used. For example, in order to suppress crystallization, a substance such as rubrene which suppresses crystallization, may be further added. In addition, NPB, Alq, or the like may be further added in order to efficiently transfer energy to the guest material.

With a structure in which a guest material is dispersed in a host material, crystallization of the light-emitting layer 113 can be suppressed. In addition, concentration quenching due to high concentration of the guest material can also be suppressed.

The electron-transport layer 114 is a layer including a substance having a high electron-transport property. Examples of the substance having a high electron-transport property are metal complexes having a quinoline skeleton or a benzoquinoline skeleton, such as tris(8-quinolinolato)aluminum (abbreviation: Alq), tris(4-methyl-8-quinolinolato) aluminum (abbreviation: Almq$_3$), bis(10-hydroxybenzo[h] quinolinato)beryllium (abbreviation: BeBq$_2$), and bis(2-methyl-8-quinolinolato)(4-phenylphenolato)aluminum (abbreviation: BAlq). Other examples are metal complexes having an oxazole-based or thiazole-based ligand, such as bis[2-(2-hydroxyphenyl)benzoxazolato]zinc (abbreviation: Zn(BOX)$_2$) and bis[2-(2-hydroxyphenyl)benzothiazolato] zinc (abbreviation: Zn(BTZ)$_2$). Other than metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can be used. The substances described here are mainly substances having an electron mobility of $10^{-6}$ cm$^2$/Vs or more. Further, the electron-transport layer is not limited to a single layer, and may be a stack of two or more layers containing any of the above substances.

The electron-injection layer 115 is a layer that contains a substance having a high electron-injection property. Examples of the substance that can be used for the electron-injection layer 115 are alkali metals, alkaline earth metals, and compounds thereof, such as lithium, cesium, calcium, lithium fluoride, cesium fluoride, calcium fluoride, and lithium oxide, rare earth-metal compounds, such as erbium fluoride, and the above-mentioned substances for forming the electron-transport layer 114.

Alternatively, a composite material formed by combining an organic compound and an electron donor (a donor) may be used for the electron-injection layer 115. Such a composite material, in which electrons are generated in the organic compound by the electron donor, has high electron-injection and electron-transport properties. The organic compound here is preferably a material excellent in transporting the generated electrons, and specifically any of the above substances (such as metal complexes and heteroaromatic compounds) for the electron-transport layer 114 can be used. The electron donor can be a substance exhibiting an electron-donating property for the organic compound. Specific examples of the electron donor are alkali metals, alkaline earth metals, and rare earth-metals, such as lithium, cesium, magnesium, calcium, erbium, and ytterbium. Any of alkali metal oxides and alkaline earth metal oxides is preferable, examples of which are lithium oxide, calcium oxide, barium oxide, and the like, and a Lewis base such as magnesium oxide or an organic compound such as tetrathiafulvalene (abbreviation: TTF) can be used.

Note that the hole-injection layer 111, the hole-transport layer 112, the light-emitting layer 113, the electron-transport layer 114, and the electron-injection layer 115 which are described above can each be formed by a method, such as an evaporation method (e.g., a vacuum evaporation method), an inkjet method, or a coating method.

When the second electrode 103 functions as a cathode, any of metals, alloys, conductive compounds, mixtures thereof, and the like which has a low work function (specifically, a work function of 3.8 eV or less) is preferably used for the second electrode 103. Specific examples of the substance that can be used are elements that belong to Groups 1 and 2 in the periodic table, that is, alkali metals such as lithium and cesium, alkaline earth metals such as magnesium, calcium, and strontium, alloys thereof (e.g., Mg—Ag and Al—Li), rare earth-metals such as europium and ytterbium, alloys thereof, aluminum, silver, and the like.

When a layer included in the EL layer 102 and formed in contact with the second electrode 103 is formed using the composite material formed by combining the organic compound and the electron donor (the donor), which are described above, a variety of conductive materials, such as aluminum, silver, ITO, and indium oxide-tin oxide containing silicon or silicon oxide, can be used regardless of the work function.

Note that when the second electrode 103 is formed, a vacuum evaporation method or a sputtering method can be used. In the case of using a silver paste or the like, a coating method, an inkjet method, or the like can be used.

In the above-described light-emitting element, a current flows due to a potential difference generated between the first electrode 101 and the second electrode 103 and holes and electrons recombine in the EL layer 102, so that light is emitted. Then, this light emission is extracted outside through one or both of the first electrode 101 and the second electrode 103. Therefore, one or both of the first electrode 101 and the second electrode 103 are electrodes having a property of transmitting visible light.

Further, the structure of the layers provided between the first electrode 101 and the second electrode 103 is not limited to the above-described structure. A structure other than the above may alternatively be employed as long as a light-emitting region in which holes and electrons recombine is provided in a portion away from the first electrode 101 and the second electrode 103 so as to prevent quenching due to proximity of the light-emitting region to metal.

In other words, there is no particular limitation on a stack structure of the layers. A layer including a substance having a high electron-transport property, a substance having a high hole-transport property, a substance having a high electron-injection property, a substance having a high hole-injection property, a bipolar substance (a substance having a high electron-transport property and a high hole-transport property), a hole-blocking material, or the like may freely be combined with a light-emitting layer and a hole-transport layer including a heterocyclic compound of one embodiment of the present invention.

A heterocyclic compound of one embodiment of the present invention is a substance having a low HOMO level, and thus can be favorably used as a hole-blocking material.

In the light-emitting element illustrated in FIG. 1B, the EL layer 102 is provided between a pair of electrodes, the first electrode 101 and the second electrode 103, over the substrate 100. The EL layer 102 includes the hole-injection layer 111, the hole-transport layer 112, the light-emitting layer 113, the electron-transport layer 114, and the electron-injection layer 115. The light-emitting element in FIG. 1B includes the second electrode 103 serving as a cathode over the substrate 100, the electron-injection layer 115, the electron-transport layer 114, the light-emitting layer 113, the hole-transport layer 112, and the hole-injection layer 111 which are stacked over the second electrode 103 in this order, and the first electrode 101 provided thereover which serves as an anode.

Note that a light-emitting element of this embodiment includes a heterocyclic compound of one embodiment of the present invention in a hole-transport layer; however, a light-emitting element of the present invention is not limited to this structure.

For example, a heterocyclic compound of one embodiment of the present invention may be included in a hole-injection layer of a light-emitting element. In this case, a hole-transport layer may be formed using a heterocyclic compound of one embodiment of the present invention, or may be formed using another material having a high hole-transport property. In addition, as described above, a heterocyclic compound of one embodiment of the present invention may be used as a host material of a fluorescent light-emitting material or a phosphorescent light-emitting material which emits phosphorescence to green.

A heterocyclic compound of one embodiment of the present invention has a low HOMO level, a high LUMO level, and a wide band gap. Thus, it can be favorably used for a carrier-transport layer (such as a hole-transport layer, an electron-transport layer, or a hole-blocking layer) adjacent to a light-emitting layer. Accordingly, a highly efficient element can be obtained.

A method of forming the light-emitting element will now be specifically described.

In a light-emitting element of this embodiment, the EL layer is interposed between the pair of electrodes. The EL layer includes at least a hole-transport layer and a light-emitting layer, and the hole-transport layer includes a heterocyclic compound of one embodiment of the present invention. Further, the EL layer may include a hole-injection layer, an electron-transport layer, or an electron-injection layer in addition to the light-emitting layer and the hole-transport layer. The electrodes (the first electrode and the second electrode) and the EL layer may be formed by any of a wet process such as a droplet discharging method (an inkjet method), a spin coating method, or a printing method, or by a dry process such as a vacuum evaporation method, a CVD method, or a sputtering method. A wet process allows formation at atmospheric pressure with a simple apparatus and by a simple process, which gives the effects of simplifying the process and improving productivity. In contrast, a dry process does not need dissolution of a material and enables use of a material that has low solubility in a solution, which expands the range of material choices.

All the thin films included in the light-emitting element may be formed by a wet process. In this case, the light-emitting element can be manufactured with only facilities needed for a wet process. Alternatively, the following method may be employed: formation of the stacked layers up to formation of the light-emitting layer is performed by a wet process whereas a functional layer, the first electrode, and the like which are stacked over the light-emitting layer are formed by a dry process. Further alternatively, the following method may be employed: the second electrode and a functional layer are formed by a dry process before the formation of the light-emitting layer whereas the light-emitting layer, a functional layer stacked thereover, and the first electrode are formed by a wet process. Needless to say, this embodiment is not limited to these, and a light-emitting element can be formed by appropriate selection from a wet process and a dry process depending on a material to be used, necessary film thickness, and the interface state.

In this embodiment, a light-emitting element is fabricated over a substrate made of glass, plastic, or the like. By forming a plurality of such light-emitting elements over one substrate, a passive matrix light-emitting device can be manufactured. Further, a light-emitting element may be fabricated in such a way that a thin film transistor (TFT), for example, is formed over a substrate made of glass, plastic, or the like and the light-emitting element is formed over an electrode electrically connected to the TFT. Thus, an active matrix light-emitting device in which the TFT controls the driving of the light-emitting element can be manufactured. Note that there is no particular limitation on the structure of the TFT; a staggered TFT or an inverted staggered TFT may be employed. In addition, there is no particular limitation on the crystallinity of a semiconductor used for the TFT; an amorphous semiconductor or a crystalline semiconductor may be used. Furthermore, a driver circuit formed over a TFT substrate may be formed with both n-channel TFTs and p-channel TFTs or may be formed with either n-channel TFTs or p-channel TFTs.

In the above manner, a light-emitting element can be manufactured using a heterocyclic compound described in Embodiment 1. According to one embodiment of the present invention, a light-emitting element having high emission efficiency can be realized.

Furthermore, a light-emitting device (an image display device) including a light-emitting element of one embodiment of the present invention which is obtained as above can realize low power consumption.

Note that by use of a light-emitting element described in this embodiment, a passive matrix light-emitting device or an active matrix light-emitting device in which driving of the light-emitting element is controlled by a thin film transistor (TFT) can be manufactured.

This embodiment can be implemented in appropriate combination with any of the other embodiments.

Embodiment 3

In this embodiment, a mode of a light-emitting element having a structure in which a plurality of light-emitting units is stacked (hereinafter, referred to as a stacked-type element) will be described with reference to FIGS. 2A and 2B. This light-emitting element is a light-emitting element including a plurality of light-emitting units between a first electrode and a second electrode.

Figure 2A:
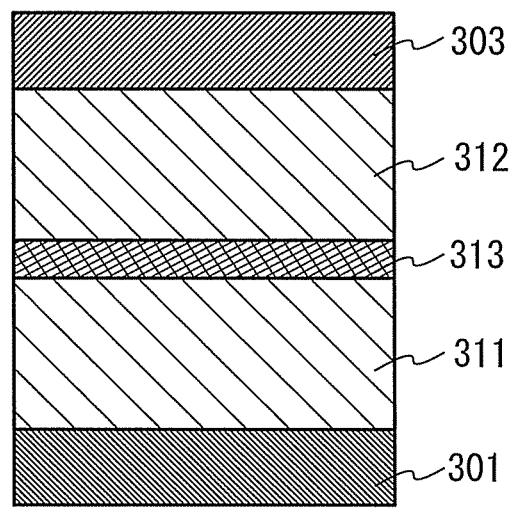
FIGS. 2A and 2B each illustrate a light-emitting element of one embodiment of the present invention.

In FIG. 2A, a first light-emitting unit 311 and a second light-emitting unit 312 are stacked between a first electrode 301 and a second electrode 303. In this embodiment, the first electrode 301 functions as an anode and the second electrode 303 functions as a cathode. Note that the first electrode 301 and the second electrode 303 can be similar to those in Embodiment 2. Further, the first light-emitting unit 311 and the second light-emitting unit 312 may have the same or different structures. The first light-emitting unit 311 and the second light-emitting unit 312 may have the same structure as in Embodiment 2, or either of the units may differ in structure from that in Embodiment 2.

Further, a charge-generation layer 313 is provided between the first light-emitting unit 311 and the second light-emitting unit 312. The charge-generation layer 313 has a function of injecting electrons into one of the light-emitting units and injecting holes into the other of the light-emitting units when a voltage is applied between the first electrode 301 and the second electrode 303. In the case of this embodiment, when a voltage is applied so that the potential of the first electrode 301 is higher than that of the second electrode 303, the charge-generation layer 313 injects electrons into the first light-emitting unit 311 and injects holes into the second light-emitting unit 312.

Note that the charge-generation layer 313 preferably has a property of transmitting visible light in terms of light extraction efficiency. Further, the charge-generation layer 313 functions even if it has lower conductivity than the first electrode 301 or the second electrode 303.

The charge-generation layer 313 may have a structure in which it includes the organic compound having a high hole-transport property and the electron acceptor (the acceptor) or a structure in which it includes an organic compound having a high electron-transport property and the electron donor (the donor), or may be a stack of both of these structures. Note that the electron acceptor or the electron donor is at least capable of providing and receiving electrons with the assistance of an electric field.

In the case of a structure in which the electron acceptor is added to an organic compound having a high hole-transport property, a heterocyclic compound of one embodiment of the present invention can be used as the organic compound having a high hole-transport property. Other examples are aromatic amine compounds, such as NPB, TPD, TDATA, MTDATA, and 4,4'-bis[N-(spiro-9,9'-bifluoren-2-yl)-N-phenylamino]biphenyl (abbreviation: BSPB), and the like. The substances mentioned here are mainly substances that have a hole mobility of $10^{-6}$ cm$^2$/Vs or more. Note that other than the above substances, any organic compound that has a property of transporting more holes than electrons may be used.

Examples of the electron acceptor are 7,7,8,8-tetracyano-2,3,5,6-tetrafluoroquinodimethane (abbreviation: F$_4$-TCNQ), chloranil, oxides of transition metals, and oxides of metals that belong to Groups 4 to 8 in the periodic table, and the like. Specific preferred examples include vanadium oxide, niobium oxide, tantalum oxide, chromium oxide, molybdenum oxide, tungsten oxide, manganese oxide, and rhenium oxide because their electron-acceptor properties are high. Among these, molybdenum oxide is especially preferable since it is stable in the air, has low hygroscopic property, and is easily treated.

In the case of the structure in which the electron donor is added to an organic compound having a high electron-transport property, any of the following substances can be used as the organic compound having a high electron-transport property, for example: metal complexes having a quinoline skeleton or a benzoquinoline skeleton such as Alq, Almq$_3$, BeBq$_2$, and BAlq; metal complexes having an oxazole-based ligand or a thiazole-based ligand, such as Zn(BOX)$_2$ and Zn(BTZ)$_2$; and the like. Examples other than the metal complexes are PBD, OXD-7, TAZ, BPhen, BCP, and the like. The substances described here are mainly substances having an electron mobility of $10^{-6}$ cm$^2$/Vs or more. Note that other than the above substances, any organic compound that has a property of transporting more electrons than holes may be used.

Examples of the electron donor that can be used are alkali metals, alkaline-earth metals, rare-earth metals, metals that belong to Group 13 in the periodic table and oxides or carbonates thereof, and preferably specifically lithium, cesium, magnesium, calcium, ytterbium, indium, lithium oxide, cesium carbonate, and the like. An organic compound, such as tetrathianaphthacene, may be used as the electron donor.

By forming the charge-generation layer 313 with any of the above materials, it is possible to suppress an increase in driving voltage caused when the EL layers are stacked.

Figure 2B:
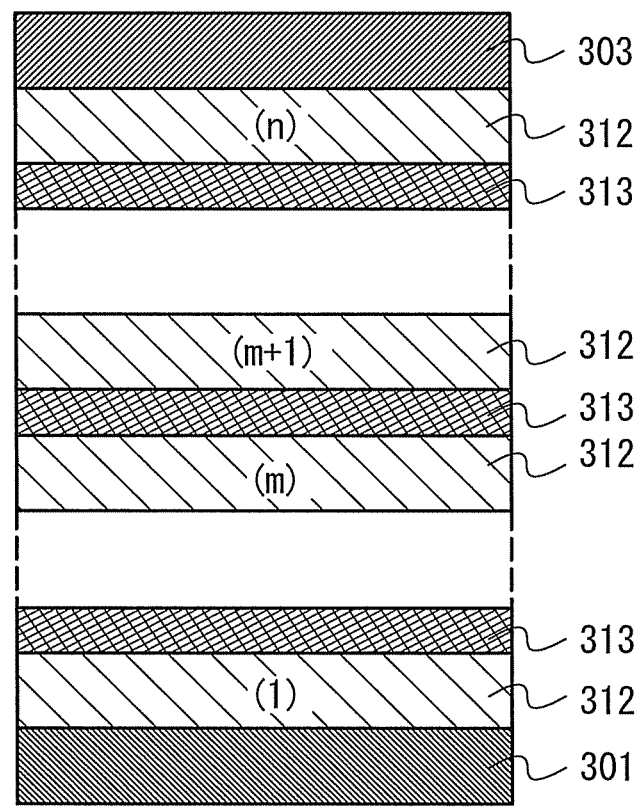

Although the light-emitting element having two light-emitting units is described in this embodiment, the embodiment can be applied to a light-emitting element in which three or more light-emitting units are stacked as illustrated in FIG. 2B. A plurality of light-emitting units which is partitioned by a charge-generation layer is arranged between a pair of electrodes, as in the light-emitting element according to this embodiment, whereby it is possible to realize an element having a long lifetime which can emit light with a high luminance while current density is kept low.

Furthermore, by making emission colors of the light-emitting units different, light having a desired color can be obtained from the light-emitting element as a whole. For example, the emission colors of first and second light-emitting units are complementary in a light-emitting element having the two light-emitting units, so that the light-emitting element can be made to emit white light as a whole. Note that the term "complementary" means color relationship in which an achromatic color is obtained when colors are mixed. That is, emission of white light can be obtained by mixture of light emitted from substances whose emission colors are complementary colors. Further, the same applies to a light-emitting element having three light-emitting units. For example, the light-emitting element as a whole can emit white light when the emission color of the first light-emitting unit is red, the emission color of the second light-emitting unit is green, and the emission color of the third light-emitting unit is blue.

Note that this embodiment can be implemented in appropriate combination with any of the other embodiments.

Embodiment 4

In this embodiment, a light-emitting device including a light-emitting element of one embodiment of the present invention will be described with reference to FIGS. 3A and 3B. Note that FIG. 3A is a top view illustrating the light-emitting device, and FIG. 3B is a cross-sectional view taken along lines A-B and C-D of FIG. 3A.

Figure 3A:
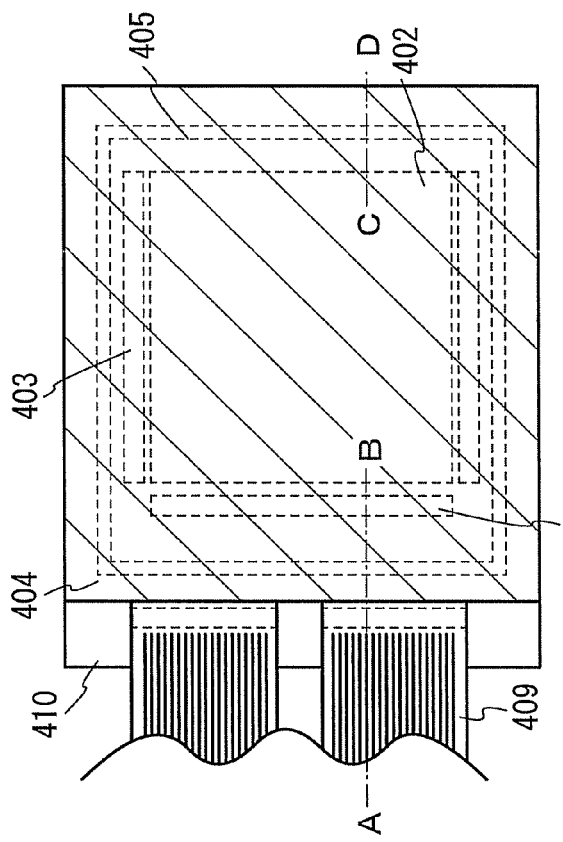
FIGS. 3A and 3B illustrate a light-emitting device of one embodiment of the present invention.
Figure 3B:
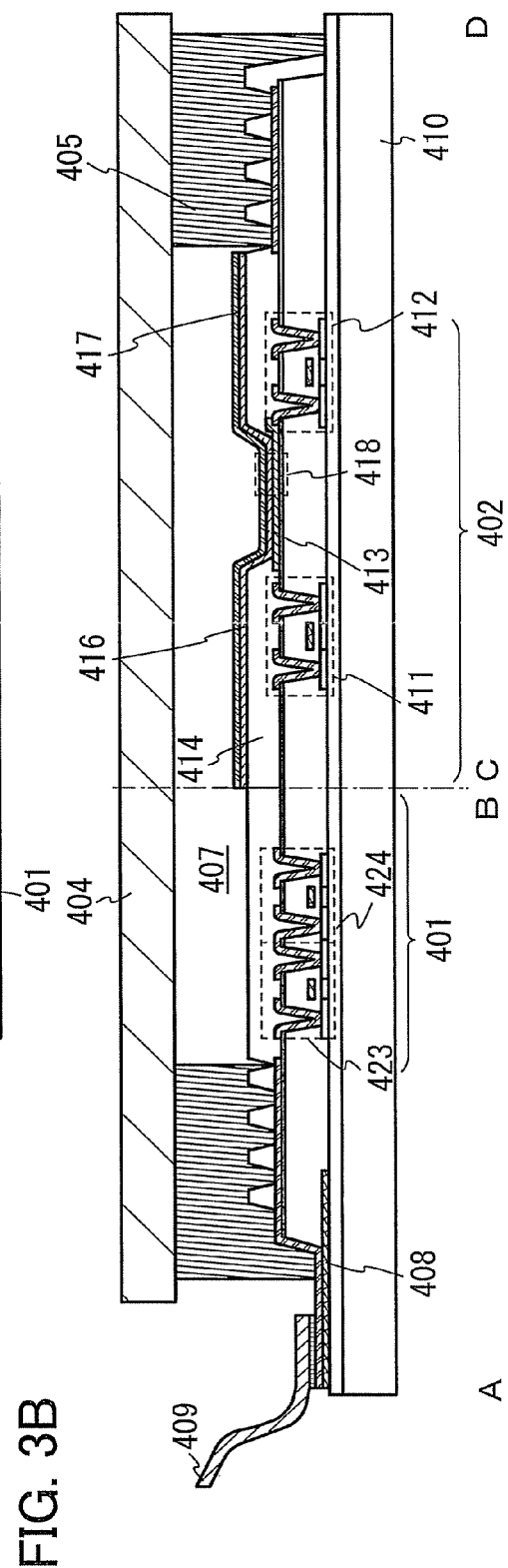

In FIG. 3A, reference numeral 401 denotes a driver circuit portion (a source side driver circuit), reference numeral 402 denotes a pixel portion, and reference numeral 403 denotes a driver circuit portion (a gate side driver circuit), which are each indicated by dotted lines. Reference numeral 404 denotes a sealing substrate, reference numeral 405 denotes a sealing material, and a portion enclosed by the sealing material 405 is a space 407.

Note that a lead wiring 408 is a wiring for transmitting signals that are to be input to the source side driver circuit 401 and the gate side driver circuit 403, and receives a video signal, a clock signal, a start signal, a reset signal, and the like from a flexible printed circuit (FPC) 409 which serves as an external input terminal. Although only the FPC is illustrated here, a printed wiring board (PWB) may be attached to the FPC. The light-emitting device in this specification includes not only a light-emitting device itself but also a light-emitting device to which an FPC or a PWB is attached.

Next, a cross-sectional structure will be described with reference to FIG. 3B. The driver circuit portion and the pixel portion are formed over an element substrate 410. Here, the source side driver circuit 401 which is the driver circuit portion and one pixel in the pixel portion 402 are illustrated.

Note that as the source side driver circuit 401, a CMOS circuit which includes an n-channel TFT 423 and a p-channel TFT 424 is formed. The driver circuit may be any of a variety of circuits formed with TFTs, such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 402 includes a plurality of pixels having a switching TFT 41 a current control TFT 412, and a first electrode 413 electrically connected to a drain of the current control TFT 412. Note that an insulator 414 is formed to cover an end portion of the first electrode 413. Here, the insulator 414 is formed by using a positive type photosensitive acrylic resin film.

In order to improve coverage, the insulator 414 is provided such that either an upper end portion or a lower end portion of the insulator 414 has a curved surface with a curvature. For example, when positive photosensitive acrylic is used as a material for the insulator 414, it is preferable that only an upper end portion of the insulator 414 have a curved surface with a radius of curvature (0.2 μm to 3 μm). For the insulator 414, it is also possible to use either a negative type that becomes insoluble in an etchant by light irradiation or a positive type that becomes soluble in an etchant by light irradiation.

An EL layer 416 and a second electrode 417 are formed over the first electrode 413. Here, as a material for forming the first electrode 413 functioning as the anode, a material having a high work function is preferably used. For example, it is possible to use a single layer of an ITO film, an indium tin oxide film that includes silicon, an indium oxide film that includes 2 wt % to 20 wt % of zinc oxide, a titanium nitride film, a chromium film, a tungsten film, a Zn film, a Pt film, or the like, a stacked layer of a titanium nitride film and a film that mainly includes aluminum, a three-layer structure of a titanium nitride film, a film that mainly includes aluminum, and a titanium nitride film, or the like. Note that, when a stacked layer structure is employed, resistance of a wiring is low and an excellent ohmic contact is obtained.

In addition, the EL layer 416 is formed by any of various methods such as an evaporation method using an evaporation mask, a droplet discharging method like an inkjet method, a printing method, and a spin coating method. The EL layer 416 includes a heterocyclic compound described in Embodiment 1. Further, another material included in the EL layer 416 may be a low molecular material, an oligomer, a dendrimer, a high molecular material, or the like.

As a material used for the second electrode 417 which is formed over the EL layer 416 and serves as a cathode, it is preferable to use a material having a low work function (e.g., Al, Mg, Li, Ca, or an alloy or a compound thereof such as Mg—Ag, Mg—In, or Al—Li). In order that light generated in the EL layer 416 be transmitted through the second electrode 417, a stack of a metal thin film having a reduced thickness and a transparent conductive film (e.g., ITO, indium oxide containing 2 wt % to 20 wt % of zinc oxide, indium oxide-tin oxide that includes silicon or silicon oxide, or zinc oxide) is preferably used for the second electrode 417.

Further, the sealing substrate 404 is attached to the element substrate 410 with the sealing material 405, so that a light-emitting element 418 is provided in the space 407 enclosed by the element substrate 410, the sealing substrate 404, and the sealing material 405. The space 407 is filled with a filler, and may be filled with an inert gas (such as nitrogen or argon) or the sealing material 405.

Note that an epoxy-based resin is preferably used as the sealing material 405. Such a material preferably allows as little moisture and oxygen as possible to penetrate. As a material used for the sealing substrate 404, a plastic substrate formed of fiberglass-reinforced plastics (FRP), polyvinyl fluoride (PVF), polyester, acrylic, or the like can be used other than a glass substrate or a quartz substrate.

As described above, the active matrix light-emitting device including the light-emitting element of one embodiment of the present invention can be obtained.

Figure 4A:
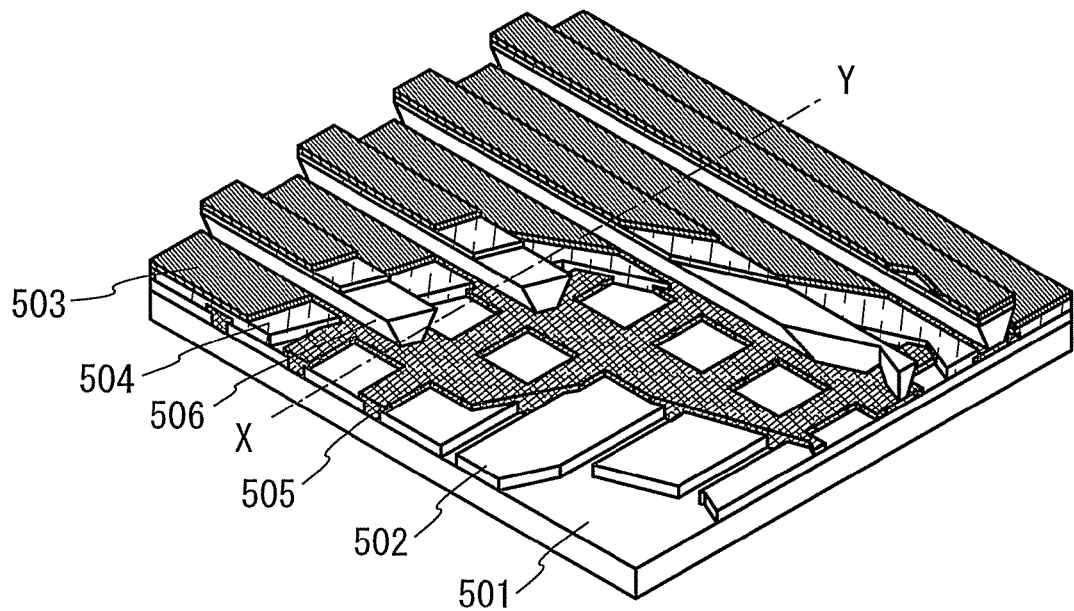
FIGS. 4A and 4B illustrate a light-emitting device of one embodiment of the present invention.
Figure 4B:
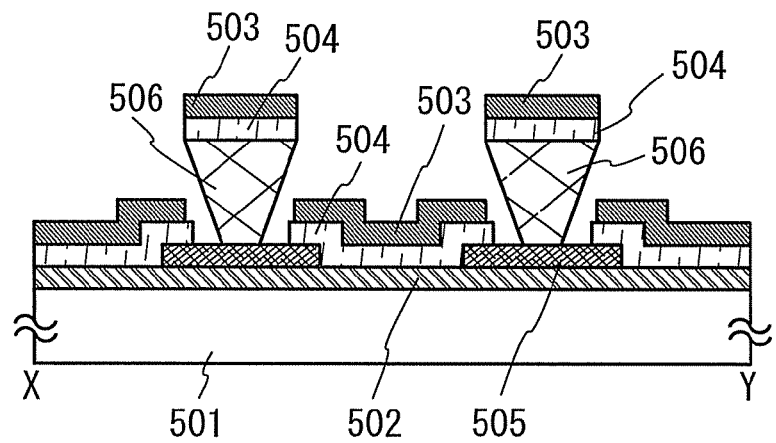

Further, a light-emitting element of the present invention can be used for a passive matrix light-emitting device as well as the above active matrix light-emitting device. FIGS. 4A and 4B illustrate a perspective view and a cross-sectional view of a passive matrix light-emitting device including a light-emitting element of the present invention. Note that FIG. 4A is a perspective view of the light-emitting device, and FIG. 4B is a cross-sectional view taken along line X-Y of FIG. 4A.

In FIGS. 4A and 4B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 slope so that a distance between both the sidewalls is gradually narrowed toward the surface of the substrate. In other words, a cross section taken along the direction of the short side of the partition layer 506 is trapezoidal, and the base (side in contact with the insulating layer 505) is shorter than the upper side (side not in contact with the insulating layer 505). With the partition layer 506 provided in such a way, a defect of a light-emitting element due to crosstalk or the like can be prevented.

Thus, the passive matrix light-emitting device including a light-emitting element of one embodiment of the present invention can be obtained.

The light-emitting devices described in this embodiment (the active matrix light-emitting device and the passive matrix light-emitting device) are both formed using a light-emitting element of one embodiment of the present invention, and accordingly, the light-emitting devices have low power consumption.

Note that this embodiment can be implemented in appropriate combination with any of the other embodiments.

Embodiment 5

In this embodiment, with reference to FIGS. 5A to 5E and FIG. 6, description is given of examples of a variety of electronic devices and lighting devices that are each completed by using a light-emitting device which is one embodiment of the present invention.

Examples of the electronic devices to which the light-emitting device is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices and a lighting device are illustrated in FIGS. 5A to 5E.

Figure 5A:
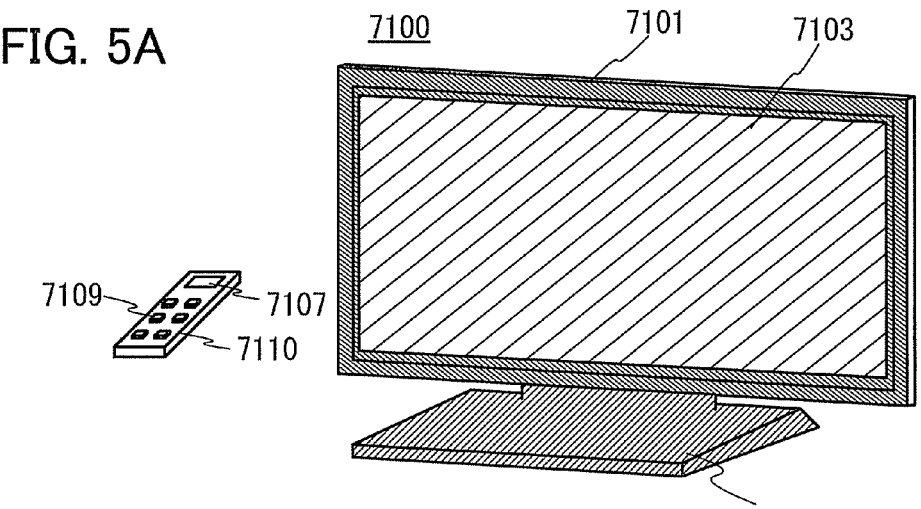
FIGS. 5A to 5E each illustrate an electronic device of one embodiment of the present invention.

FIG. 5A illustrates an example of a television device. In the television device 7100, a display portion 7103 is incorporated in a housing 7101. The display portion 7103 is capable of displaying images, and a light-emitting device can be used for the display portion 7103. In addition, here, the housing 7101 is supported by a stand 7105.

The television device 7100 can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, general television broadcasting can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 5B:
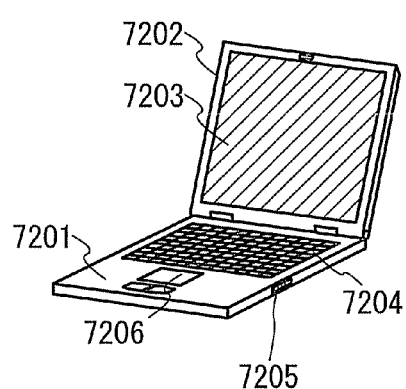

FIG. 5B illustrates a computer, which includes a main body 7201, a housing 7202, a display portion 7203, a keyboard 7204, an external connection port 7205, a pointing device 7206, and the like. This computer is manufactured by using a light-emitting device for the display portion 7203.

Figure 5C:
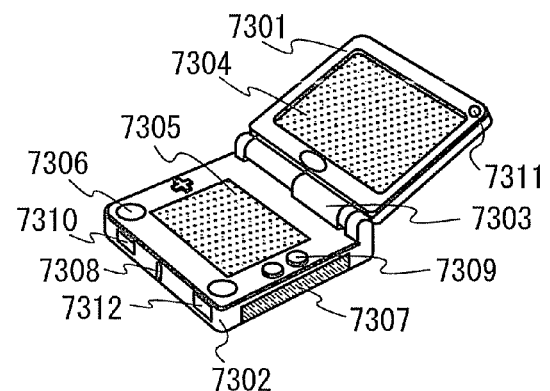

FIG. 5C illustrates a portable game machine, which includes two housings, a housing 7301 and a housing 7302, connected with a joint portion 7303 so that the portable game machine can be opened or closed. A display portion 7304 is incorporated in the housing 7301 and a display portion 7305 is incorporated in the housing 7302. In addition, the portable game machine illustrated in FIG. 5C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. It is needless to say that the structure of the portable game machine is not limited to the above as long as a light-emitting device is used for at least either the display portion 7304 or the display portion 7305, or both, and may include other accessories as appropriate. The portable game machine illustrated in FIG. 5C has a function of reading out a program or data stored in a storage medium to display it on the display portion, and a function of sharing information with another portable game machine by wireless communication. The portable game machine illustrated in FIG. 5C can have a variety of functions without limitation to the above.

Figure 5D:
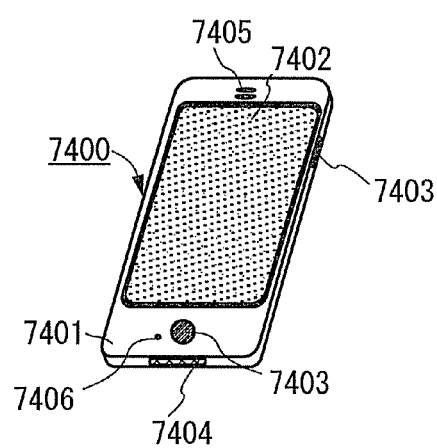

FIG. 5D illustrates an example of a cellular phone. The cellular phone 7400 is provided with operation buttons 7403, an external connection port 7404, a speaker 7405, a microphone 7406, and the like, in addition to a display portion 7402 incorporated in a housing 7401. Note that the cellular phone 7400 is manufactured using a light-emitting device for the display portion 7402.

When the display portion 7402 of the cellular phone 7400 illustrated in FIG. 5D is touched with a finger or the like, data can be input to the cellular phone 7400. Further, operations such as making a call and creating e-mail can be performed by touch on the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are mixed.

For example, in the case of making a call or creating e-mail, a character input mode mainly for inputting characters is selected for the display portion 7402 so that characters displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touch on the display portion 7402 or operation with the operation buttons 7403 of the housing 7401. Alternatively, the screen modes can be switched depending on kinds of images displayed on the display portion 7402. For example, when a signal for an image to be displayed on the display portion is data of moving images, the screen mode is switched to the display mode. When the signal is text data, the screen mode is switched to the input mode.

Moreover, in the input mode, if a signal detected by an optical sensor in the display portion 7402 is detected and the input by touch on the display portion 7402 is not performed during a certain period, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal identification can be performed. Furthermore, by provision of a backlight or a sensing light source emitting near-infrared light for the display portion, an image of a finger vein, a palm vein, or the like can also be taken.

Figure 5E:
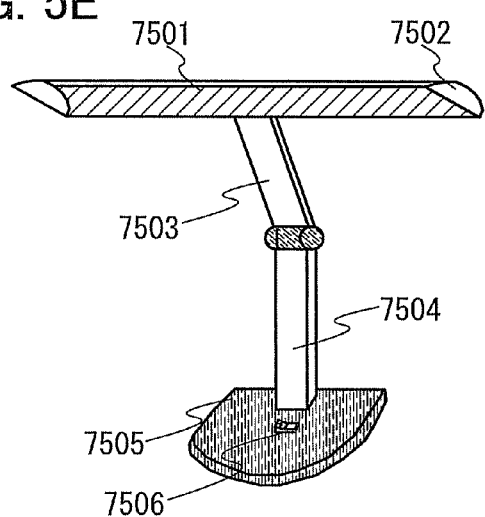

FIG. 5E illustrates a desk lamp, which includes a lighting portion 7501, a shade 7502, an adjustable arm 7503, a support 7504, a base 7505, and a power switch 7506. The desk lamp is manufactured using a light-emitting device for the lighting portion 7501. Note that the "lighting device" also includes ceiling lights, wall lights, and the like.

Figure 6:
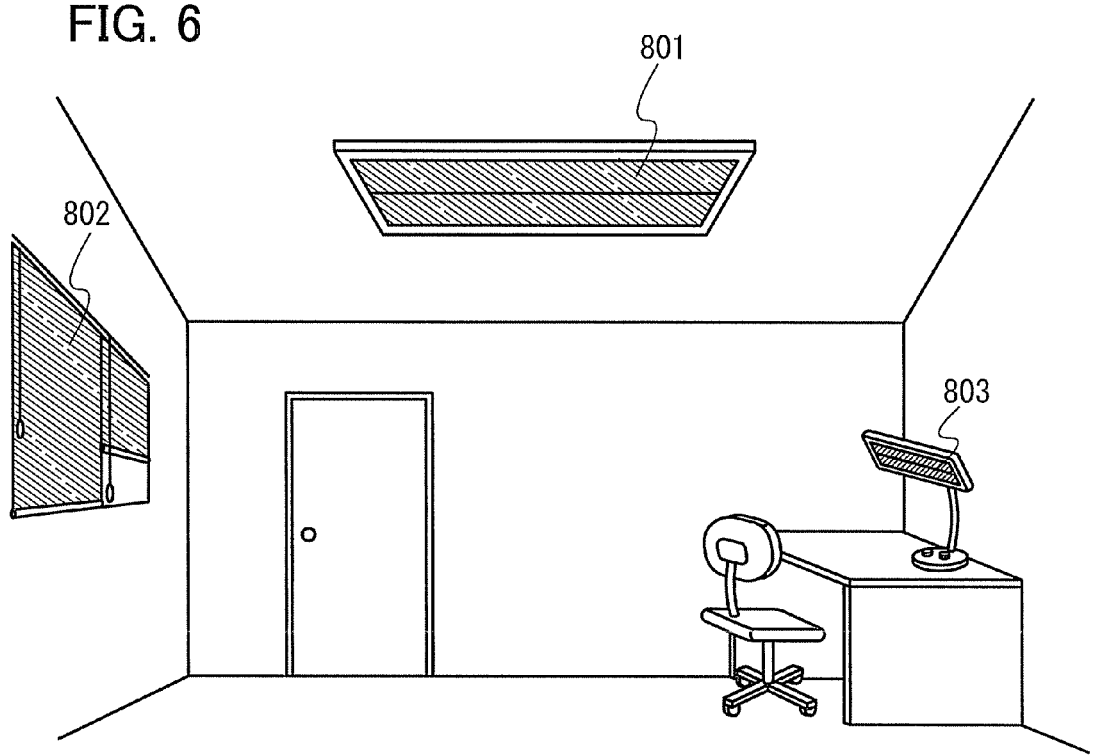
FIG. 6 illustrates a lighting device of one embodiment of the present invention.

FIG. 6 illustrates an example in which a light-emitting device is used for an interior lighting device 801. Since the light-emitting device can have a larger area, it can be used as a lighting device having a large area. Furthermore, the light-emitting device can be used as a roll-type lighting device 802. As illustrated in FIG. 6, a desk lamp 803 described with reference to FIG. 5E may also be used in a room provided with the interior lighting device 801.

In the above-described manner, electronic devices or lighting devices can be obtained by application of a light-emitting device. Application range of the light-emitting device is so wide that the light-emitting device can be applied to electronic devices in a variety of fields.

Note that the structure described in this embodiment can be combined with any of the structures described in Embodiments 1 to 4 as appropriate.

Example 1

《 Synthesis Example 1》

This example gives descriptions of a method of synthesizing 4,4'-(biphenyl-2,2'-diyl)-bis-dibenzothiophene (abbreviation: oDBTBP-II), which is a heterocyclic compound of one embodiment of the present invention, represented by the structural formula (100) in Embodiment 1.

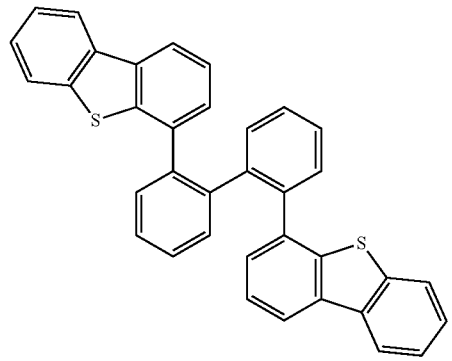

oDBTPB-II

To a 100 mL three-neck flask were added 1.6 g (5.0 mmol) of 2,2'-dibromobiphenyl, 3.2 g (11 mmol) of dibenzothiophene-4-boronic acid, 44 mg (0.2 mmol) of palladium (II)acetate, 120 mg (0.4 mmol) of tri(ortho-tolyl)phosphine, 30 mL of toluene, 3 mL of ethanol, and 20 mL of a 2 mol/L aqueous potassium carbonate solution. This mixture was degassed while being stirred under reduced pressure, and was then reacted by being heated and stirred under a nitrogen atmosphere at 90° C. for 10 hours.

After the reaction, 150 mL of toluene was added to this reaction mixture solution, and the organic layer was filtered through Florisil (produced by Wako Pure Chemical Industries, Ltd., Catalog No. 540-00135), alumina (produced by Merck & Co., Inc., neutral), and Celite (produced by Wako Pure Chemical Industries, Ltd., Catalog No. 531-16855) in this order to give a filtrate. The obtained residue was purified by silica gel column chromatography (with a developing solvent of toluene and hexane in a 1:3 ratio). The obtained fraction was concentrated, and acetone and methanol were added thereto. The mixture was irradiated with ultrasonic waves and then recrystallized to give 1.8 g of a white powder of oDBTBP-II in a yield of 69%, which was the object of the synthesis. A reaction scheme of the above synthesis method is illustrated in the following (B-1).

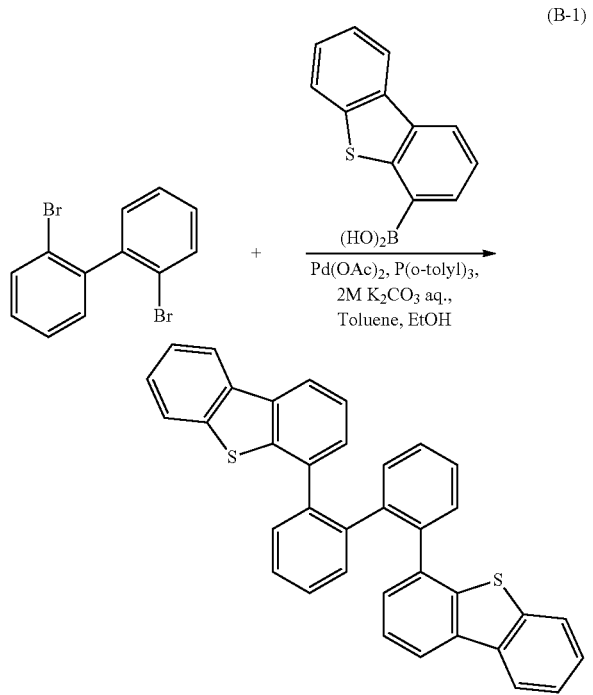

(B-1)

The Rf values of oDBTBP-II and 2,2'-dibromobiphenyl were respectively 0.56 and 0.77, which were found by silica gel thin layer chromatography (TLC) (with a developing solvent of ethyl acetate and hexane in a 1:10 ratio).

Figure 7A:
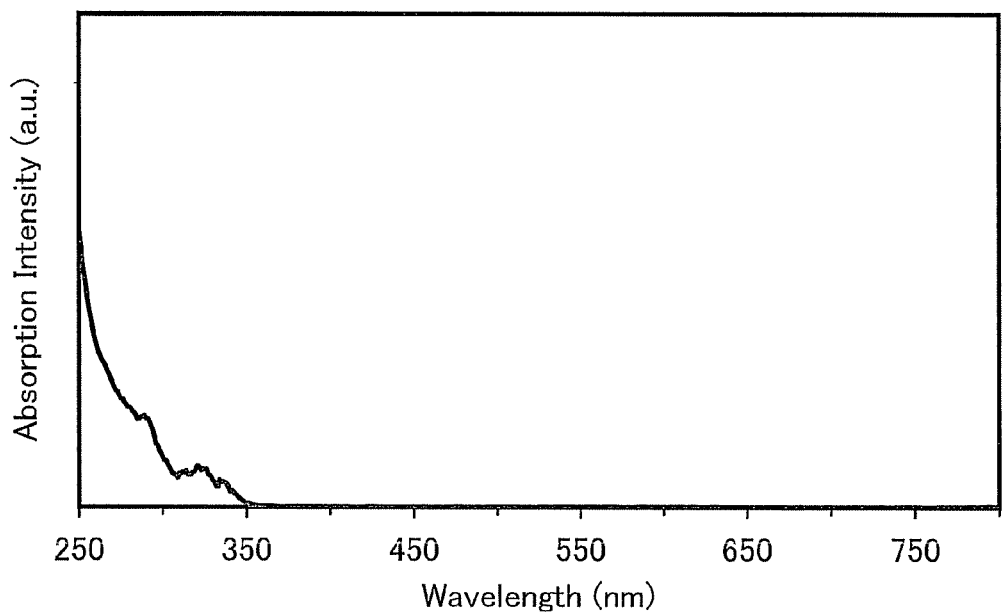
FIGS. 7A and 7B show an absorption spectrum of oDBTBP-II in a hexane solution of oDBTBP-II and an emission spectrum of oDBTBP-II in a toluene solution of oDBTBP-II.
Figure 7B:
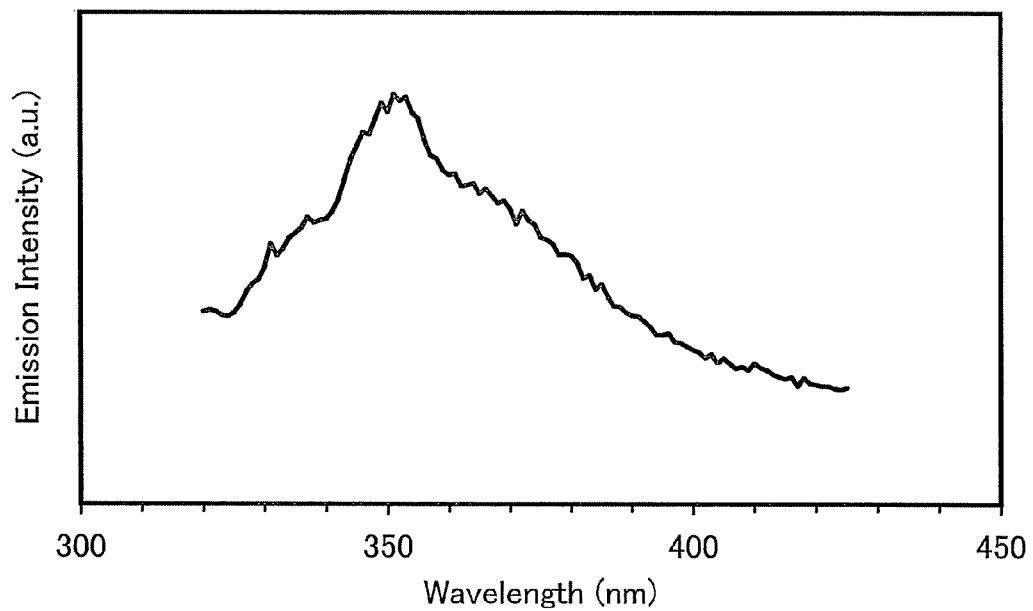
Figure 8A:
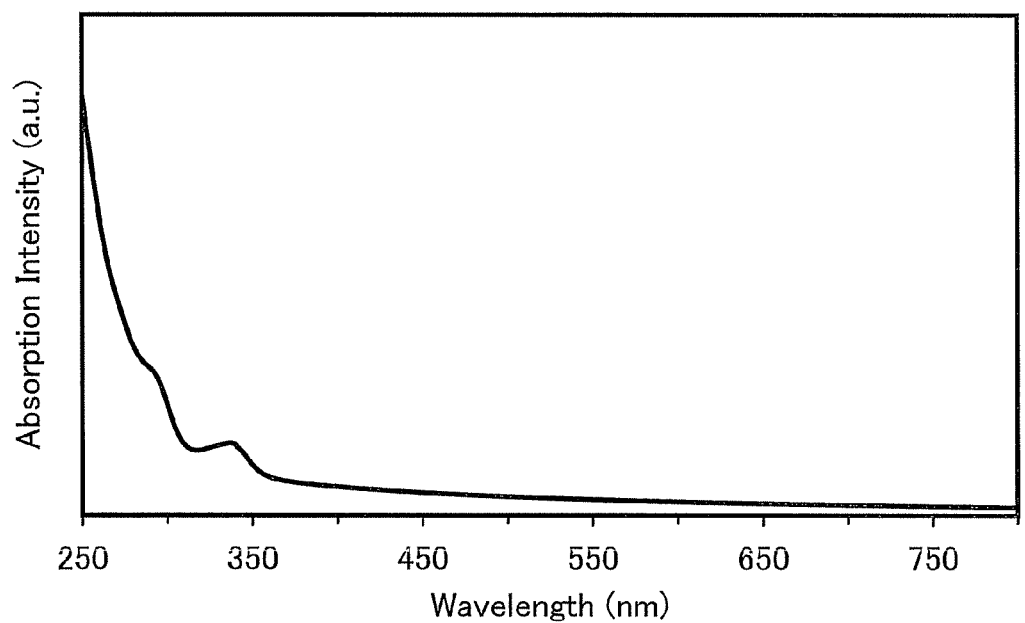
FIGS. 8A and 8B show an absorption spectrum and an emission spectrum of a thin film of oDBTBP-II.
Figure 8B:
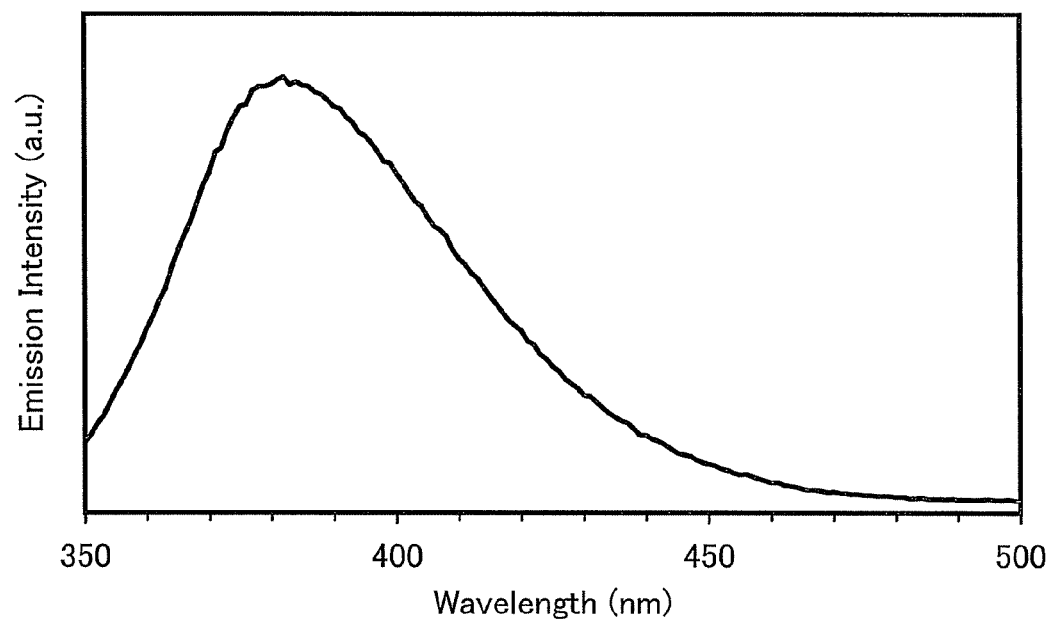

Further, FIG. 7A shows the absorption spectrum of oDBTBP-II in a hexane solution of oDBTBP-II, and FIG. 7B shows the emission spectrum of oDBTBP-II in a toluene solution of oDBTBP-II. In addition, FIG. 8A shows the absorption spectrum of a thin film of oDBTBP-II, and FIG. 8B shows the emission spectrum thereof. An ultraviolet-visible spectrophotometer (V-550, manufactured by JASCO Corporation) was used for the measurements. Samples were prepared in such a way that the solution was put in a quartz cell and the thin film was formed on a quartz substrate by evaporation. Here are shown the absorption spectrum for the solution which was obtained by subtracting the absorption spectra of quartz and hexane from those of quartz and the solution, and the absorption spectrum for the thin film which was obtained by subtracting the absorption spectrum of the quartz substrate from those of the quartz substrate and the thin film. In FIG. 7A and FIG. 8A, the horizontal axis represents wavelength (nm) and the vertical axis represents absorption intensity (arbitrary unit). In FIG. 7B and FIG. 8B, the horizontal axis represents wavelength (nm) and the vertical axis represents emission intensity (arbitrary unit). In the case of the hexane solution, absorption peaks were found at around 289 nm and 323 nm, and in the case of the toluene solution, a peak of the emission wavelength was at 352 nm (at an excitation wavelength of 270 nm). In the case of the thin film, absorption peaks were found at around 291 nm and 337 nm, and a peak of the emission wavelength was at 382 nm (at an excitation wavelength of 339 nm). FIG. 7A and FIG. 8A show that oDBTBP-II is a substance having weak absorption in the visible region. In other words, it is suggested that in the case where oDBTBP-II which is a heterocyclic compound of one embodiment of the present invention is used for a light-emitting element, visible light emitted from a light-emitting layer is unlikely to be reabsorbed by oDBTBP-II, and thus a decrease in light extraction efficiency of the element can be suppressed.

It is also found that oDBTBP-II has a peak of the emission spectrum at a very short wavelength and thus can be used for a host material of a light-emitting layer or used for a carrier-transport layer adjacent to the light-emitting layer in a fluorescent element which emits visible light.

The molecular weight of the compound obtained by the above-described synthesis method was measured with a GC/MS detector (ITQ1100 ion trap GC/MS system, manufactured by Thermo Fisher Scientific Inc.). According to the measurement, it was confirmed that a main peak with a molecular weight of 518.16 (mode was EI+) was detected and oDBTBP-II that was the object of the synthesis was obtained.

The results of the measurement of the thin film by photoelectron spectrometry (AC-2, a product of Riken Keiki Co., Ltd.) in the air indicate that the HOMO level is −5.89 eV. From the Tauc plot of the absorption spectrum of the thin film, the absorption edge was 3.45 eV. Therefore, the energy gap in the solid state is estimated to be 3.45 eV, which means that the LUMO level is −2.44 eV. This indicates that oDBTBP-II has a low HOMO level and a wide band gap.

A thin film of oDBTBP-II was formed by vacuum evaporation. This thin film was not a white and opaque film but a transparent film. This also suggests that oDBTBP-II is a substance which is unlikely to be crystallized.

Example 2

Figure 9A:
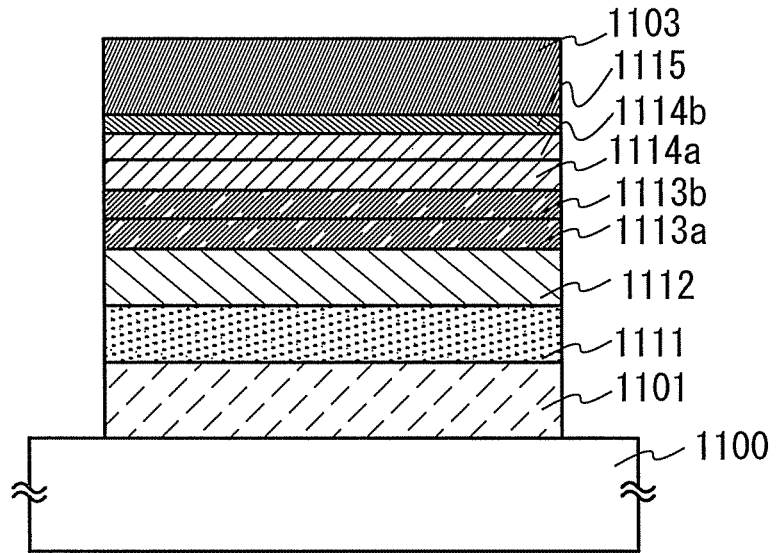
FIGS. 9A and 9B each illustrate a light-emitting, element of an example.

In this example, a light-emitting element of one embodiment of the present invention will be described with reference to FIG. 9A. The chemical formulae of materials used in this example are illustrated below.

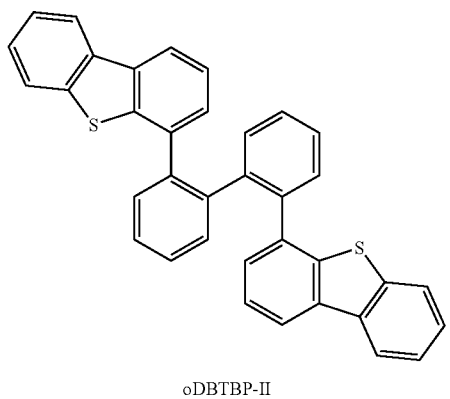 [SMILES: c1ccc(-c2cccc3c2sc2ccccc23)c(-c2ccccc2-c2cccc3c2sc2ccccc23)c1]

oDBTBP-II

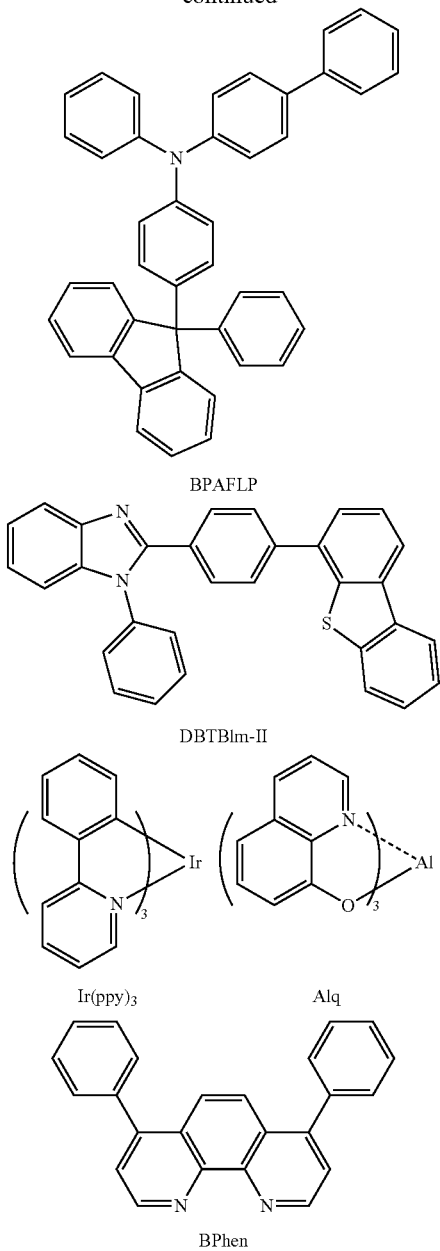

BPAFLP

DBTBIm-II

Ir(ppy)₃                Alq

BPhen

Methods for manufacturing Light-Emitting Element 1 and Light-Emitting Element 2 of this example will be described below.

(Light-Emitting Element 1)

First, a film of indium tin oxide containing silicon oxide (ITSO) was formed over a glass substrate 1100 by a sputtering method, so that a first electrode 1101 was aimed. Note that the thickness was set to 110 nm and the electrode area was set to 2 mm×2 mm.

In pretreatment for forming the light-emitting element over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about $10^{-4}$ Pa. Then, 4-phenyl-4'-(9-phenylfluoren-9-yl)triphenylamine (abbreviation: BPAFLP) and molybdenum(VI) oxide were co-evaporated to form a hole-injection layer 1111 over the first electrode 1101. The thickness of the hole-injection layer 1111 was set to 50 nm, and the weight ratio of BPAFLP to molybdenum(VI) oxide was adjusted to 4:2 (=BPAFLP:molybdenum oxide). Note that the co-evaporation method refers to an evaporation method in which evaporation is carried out from a plurality of evaporation sources at the same time in one treatment chamber.

Next, over the hole-injection layer 1111, a BPAFLP film was formed to a thickness of 10 nm to form a hole-transport layer 1112.

Further, 2-[4-(dibenzothiophen-4-yl)phenyl]-1-phenyl-1H-benzimidazole (abbreviation: DBTBIm-II), 4,4'-(biphenyl-2,2'-diyl)-bis-dibenzothiophene (abbreviation: oDBTBP-II) synthesized in Example 1, and tris(2-phenylpyridinato-N,C²')iridium(III) (abbreviation: Ir(ppy)₃) were co-evaporated to form a first light-emitting layer 1113a over the hole-transport layer 1112. Here, the weight ratio of DBTBIm-II to oDBTBP-II and Ir(ppy)₃ was adjusted to 1:0.25:0.08 (=DBTBIm-II:oDBTBP-II:Ir(ppy)₃). In addition, the thickness of the first light-emitting layer 1113a was set to 20 nm.

Next, DBTBIm-II and Ir(ppy)₃ were co-evaporated to form a second light-emitting layer 1113b over the first light-emitting layer 1113a. Here, the weight ratio of DBTBIm-II to Ir(ppy)₃ was adjusted to 1:0.08 (=DBTBIm-II:Ir(ppy)₃). In addition, the thickness of the second light-emitting layer 1113b was set to 20 nm.

Next, over the second light-emitting layer 1113b, a film of tris(8-quinolinolato)aluminum (abbreviation: Alq) was formed to a thickness of 15 nm to form a first electron-transport layer 1114a.

Then, over the first electron-transport layer 1114a, a film of bathophenanthroline (abbreviation: BPhen) was formed to a thickness of 15 nm to foam a second electron-transport layer 1114b.

Further, over the second electron-transport layer 1114b, a lithium fluoride (LiF) film was formed by evaporation to a thickness of 1 nm to form an electron-injection layer 1115.

Lastly, an aluminum film was formed by evaporation to a thickness of 200 nm as a second electrode 1103 functioning as a cathode. Thus, Light-Emitting Element 1 of this example was fabricated.

Note that, in the above evaporation steps, evaporation was all performed by a resistance heating method.

(Light-Emitting Element 2)

A hole-injection layer 1111 of Light-Emitting Element 2 was formed by co-evaporating oDBTBP-II and molybdenum(VI) oxide. The thickness of the hole-injection layer 1111 was set to 50 nm, and the weight ratio of oDBTBP-II to molybdenum(VI) oxide was adjusted to 4:2 (=oDBTBP-II:molybdenum oxide).

Further, a hole-transport layer 1112 of Light-Emitting Element 2 was formed using oDBTBP-II. The thickness of the hole-transport layer 1112 was set to 10 nm. Components other than the hole-injection layer 1111 and the hole-transport layer 1112 were manufactured in a manner similar to those of Light-Emitting Element 1.

Table 1 shows element structures of Light-Emitting Element 1 and Light-Emitting Element 2 obtained as described above.

TABLE 1

| | First electrode | Hole injection layer | Hole transport layer | First Light-emitting layer | Second Light-emitting layer | First election transport layer | Second electron transport layer | Electron injection layer | Second electrode |
|---|---|---|---|---|---|---|---|---|---|
| Light emitting element 1 | ITSO 110 nm | BPAFLP:MoOx (=4:2) 50 nm | BPAFLP 10 nm | DBTBIm-II:oDBTBP-II:Ir(ppy)$_3$ (=1:0.25:0.08) 20 nm | DBTBIm-II: Ir(ppy)$_3$ (=1:0.08) 20 nm | Alq 15 nm | BPhen 15 nm | LIF 1 nm | Al 200 nm |
| Light emitting element 2 | ITSO 110 nm | oDBTBP-II:MoOx (=4:2) 50 nm | oDBTBP-II 10 nm | DBTBIm-II:oDBTBP-II:Ir(ppy)$_3$ (=1:0.25:0.08) 20 nm | DBTBIm-II: Ir(ppy)$_3$ (=1:0.08) 20 nm | Alq 15 nm | BPhen 15 nm | LIF 1 nm | Al 200 nm |

In a glove box containing a nitrogen atmosphere, these light-emitting elements were sealed so as not to be exposed to air. Then, operation characteristics of these light-emitting elements were measured. Note that the measurements were carried out at room temperature (in the atmosphere kept at 25° C.).

Note that Light-Emitting Element 1 and Light-Emitting Element 2 were formed over the same substrate. In addition, the first electrodes and the first light-emitting layers to the second electrodes of the above-described two light-emitting elements were formed at the same respective times, and sealing was performed at the same time.

Figure 10:
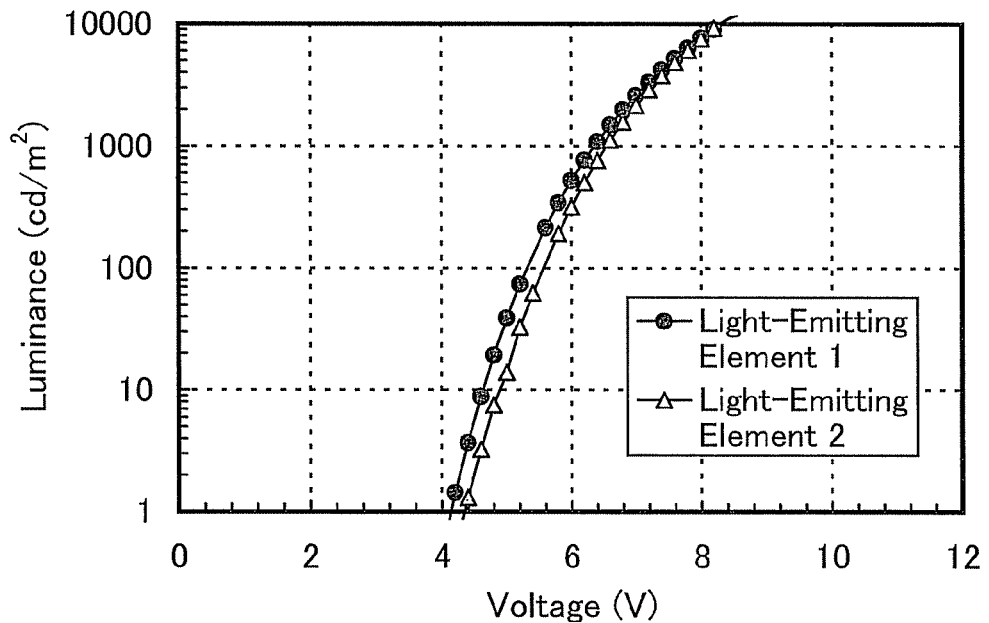
FIG. 10 shows voltage-luminance characteristics of a light-emitting element of Example 2.
Figure 11:
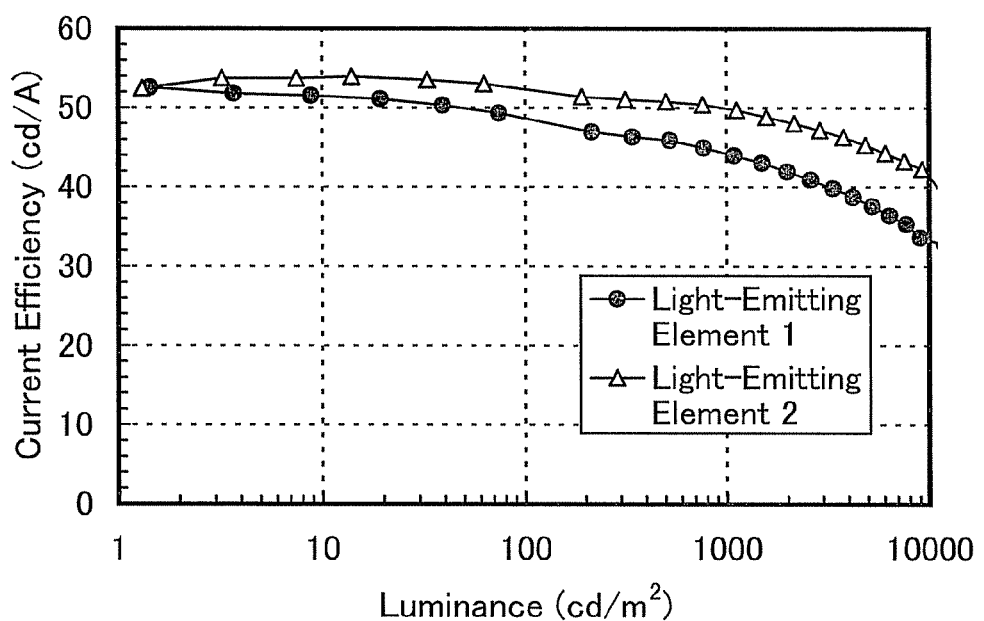
FIG. 11 shows luminance-current efficiency characteristics of a light-emitting element of Example 2.

FIG. 10 shows the voltage-luminance characteristics of Light-Emitting Element 1 and Light-Emitting Element 2. In FIG. 10, the horizontal axis represents voltage (V) and the vertical axis represents luminance (cd/m$^2$). FIG. 11 shows the luminance-current efficiency characteristics. In FIG. 11, the horizontal axis represents luminance (cd/m$^2$) and the vertical axis represents current efficiency (cd/A). Further, Table 2 shows the voltage (V), current density (mA/cm$^2$), CIE chromaticity coordinates (x, y), current efficiency (cd/A), power efficiency (lm/W), and external quantum efficiency (%) of each light-emitting element at a luminance of 1100 cd/m$^2$.

TABLE 2

| | Voltage (V) | Current density (mA/cm$^2$) | Chromaticity coordinate x | Chromaticity coordinate y | Current efficiency (cd/A) | Power efficiency (lm/W) | External quantum efficiency (%) |
|---|---|---|---|---|---|---|---|
| Light-emitting element 1 | 6.4 | 2.5 | 0.34 | 0.60 | 44 | 22 | 13 |
| Light-emitting element 2 | 6.8 | 2.3 | 0.34 | 0.61 | 50 | 24 | 15 |

Figure 12:
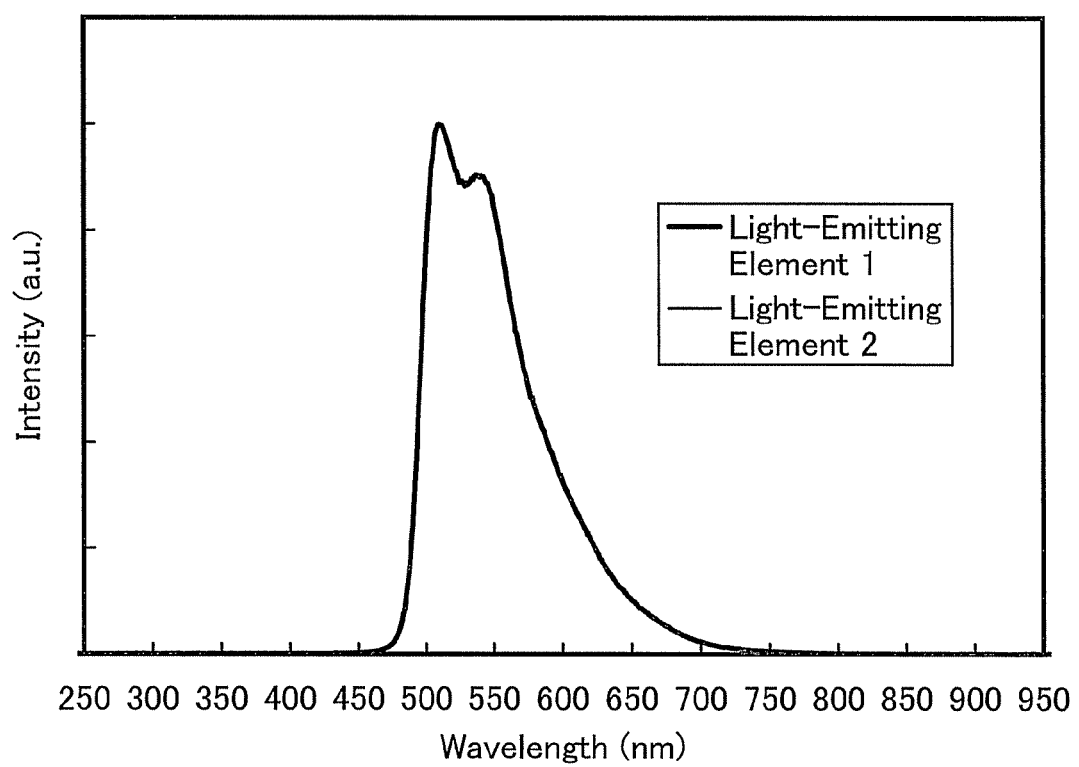
FIG. 12 shows an emission spectrum of a light-emitting element of Example 2.

FIG. 12 shows the emission spectrum of each light-emitting element which was obtained by applying a current at a current density of 0.1 mA/cm$^2$. In FIG. 12, the horizontal axis represents wavelength (nm) and the vertical axis represents intensity (arbitrary unit). As shown in FIG. 12, the emission spectra of the light-emitting elements at around 1000 cd/m$^2$ each have a peak at around 510 nm and are similar to each other. In addition, as shown in Table 2, the CIE chromaticity coordinates of Light-Emitting Element 1 were (x, y)=(0.34, 0.60) and the CIE chromaticity coordinates of Light-Emitting Element 2 were (x, y)=(0.34, 0.61), each at a luminance of 1000 cd/m$^2$. These results show that green light emission originating from Ir(ppy)$_3$ was obtained from Light-Emitting Element 1 and Light-Emitting Element 2.

As can be seen from FIG. 10 and FIG. 11, Light-Emitting Element 1 and Light-Emitting Element 2 have excellent emission efficiency. In particular, Light-Emitting Element 2 exhibits high emission efficiency.

The above results suggest that an element having high emission efficiency can be realized by use of a heterocyclic compound of one embodiment of the present invention for a host material of a light-emitting layer including a phosphorescent compound.

In order to obtain highly efficient light emission from a light-emitting element including a light-emitting layer including a phosphorescent compound, it is preferable to use a substance having a sufficiently high level of triplet excitation energy (T1 level) for a host material of a light-emitting layer. In Light-Emitting Element 1 and Light-Emitting Element 2, a light-emitting layer includes a heterocyclic compound of one embodiment of the present invention as a host material, and as shown in the aforementioned diagrams and tables, Light-Emitting Element 2 is found to have high emission efficiency. Thus, a heterocyclic compound of one embodiment of the present invention is found to have a sufficiently high T1 level. Note that the triplet excitation energy refers to an energy difference between a ground state and a triplet excited state.

The above results further suggest that an element having higher emission efficiency can be realized by use of a composite material formed by combining a heterocyclic compound of one embodiment of the present invention and an electron acceptor (an acceptor) for a hole-injection layer and by use of a heterocyclic compound of one embodiment of the present invention for a hole-transport layer.

This can be attributed to a composite material including a heterocyclic compound of one embodiment of the present invention which is a material having a high hole-injection property and a high hole-transport property. It can also be attributed to a sufficiently high LUMO level of a heterocyclic compound of one embodiment of the present invention and suppressed passage of electrons through a light-emitting layer. It can also be attributed to a sufficiently low HOMO level and an excellent property of injecting holes into a light-emitting layer.

Example 3

Figure 9B:
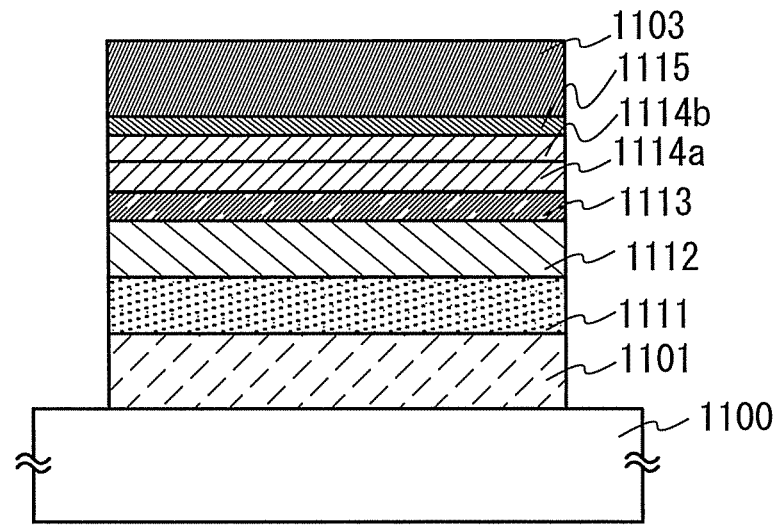

In this example, a light-emitting element of one embodiment of the present invention will be described with reference to FIG. 9B. The chemical formulae of materials used in this example are illustrated below.

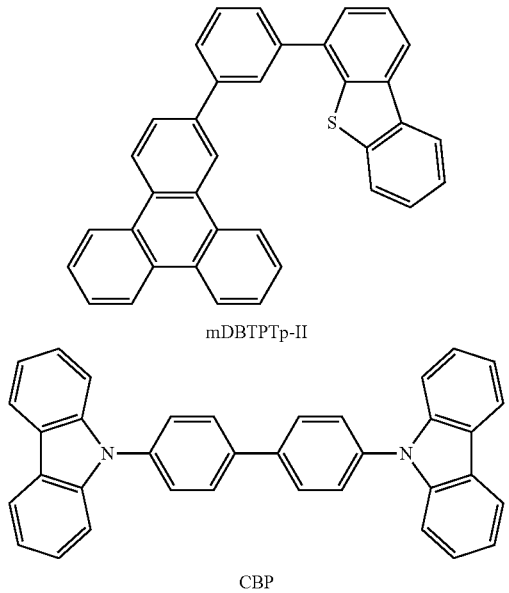

mDBTPTp-II

CBP

Methods for manufacturing Light-Emitting Element 3 and Comparative Light-Emitting Element 4 of this example will be described below.
(Light-Emitting Element 3)

First, a film of ITSO was formed over a glass substrate 1100 by a sputtering method, so that a first electrode 1101 was formed. Note that the thickness was set to 110 nm and the electrode area was set to 2 mm×2 mm.

In pretreatment for forming the light-emitting element over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about $10^{-4}$ Pa. Then, oDBTBP-II synthesized in Example 1 and molybdenum(VI) oxide were co-evaporated to form a hole-injection layer 1111 over the first electrode 1101. The thickness of the hole-injection layer 1111 was set to 50 μm, and the weight ratio of oDBTBP-II to molybdenum(VI) oxide was adjusted to 4:2 (=oDBTBP-II:molybdenum oxide).

Next, over the hole-injection layer 1111, an oDBTBP-II film was formed to a thickness of 10 nm to form a hole-transport layer 1112.

Further, 4-[3-(triphenylen-2-yl)phenyl]dibenzothiophene (abbreviation: mDBTPTp-II) and Ir(ppy)$_3$ were co-evaporated to form a light-emitting layer 1113 over the hole-transport layer 1112. Here, the weight ratio of mDBTPTp-II to Ir(ppy)$_3$ was adjusted to 1:0.08 (=mDBTPTp-II:Ir(ppy)$_3$). The thickness of the light-emitting layer 1113 was set to 40 nm.

Further, over the light-emitting layer 1113, a film of Alq was formed to a thickness of 15 nm to form a first electron-transport layer 1114a.

Then, over the first electron-transport layer 1114a, a BPhen film was formed to a thickness of 15 nm to form a second electron-transport layer 1114b.

Further, over the second electron-transport layer 1114b, a LiF film was formed by evaporation to a thickness of 1 nm to form an electron-injection layer 1115.

Lastly, an aluminum film was formed by evaporation to a thickness of 200 nm as a second electrode 1103 functioning as a cathode. Thus, Light-Emitting Element 3 of this example was fabricated.

Note that, in the above evaporation steps, evaporation was all performed by a resistance heating method.
(Comparative Light-Emitting Element 4)

A hole-injection layer 1111 of Comparative Light-Emitting Element 4 was formed by co-evaporating 4,4'-di(N-carbazolyl)biphenyl (abbreviation: CBP) and molybdenum(VI) oxide. The thickness of the hole-injection layer 1111 was set to 50 nm, and the weight ratio of CBP to molybdenum(VI) oxide was adjusted to 4:2 (=CBP:molybdenum oxide).

Further, a hole-transport layer 1112 of Comparative Light-Emitting Element 4 was formed using CBP. The thickness of the hole-transport layer 1112 was set to 10 nm. Components other than the hole-injection layer 1111 and the hole-transport layer 1112 were manufactured in a manner similar to those of Light-Emitting Element 3.

Table 3 shows element structures of Light-Emitting Element 3 and Comparative Light-Emitting Element 4 obtained as described above.

TABLE 3

| | First electrode | Hole injection layer | Hole transport layer | Light-emitting layer | First electron transport layer | Second electron transport layer | Electron injection layer | Second electrode |
|---|---|---|---|---|---|---|---|---|
| Light emitting element 3 | ITSO 110 nm | oDBTBP-II:MoOx (=4:2) 50 nm | oDBTBP-II 10 nm | mDBTPTp-II:Ir(ppy)$_3$ (=1:0.08) 40 nm | Alq 15 nm | BPhen 15 nm | LiF 1 nm | Al 200 nm |
| Comparative light emitting element 4 | ITSO 110 nm | CBP:MoOx (=4:2) 50 nm | CBP 10 nm | mDBTPTp-II:Ir(ppy)$_3$ (=1:0.08) 40 nm | Alq 15 nm | BPhen 15 nm | LiF 1 nm | Al 200 nm |

In a glove box containing a nitrogen atmosphere, these light-emitting elements were sealed so as not to be exposed to air. Then, operation characteristics of these light-emitting elements were measured. Note that the measurements were carried out at room temperature (in the atmosphere kept at 25° C.).

Note that Light-Emitting Element 3 and Comparative Light-Emitting Element 4 were formed over the same substrate. In addition, the first electrodes and the light-emitting layers to the second electrodes of the above-described two light-emitting elements were formed at the same respective times, and sealing was performed at the same time.

Figure 13:
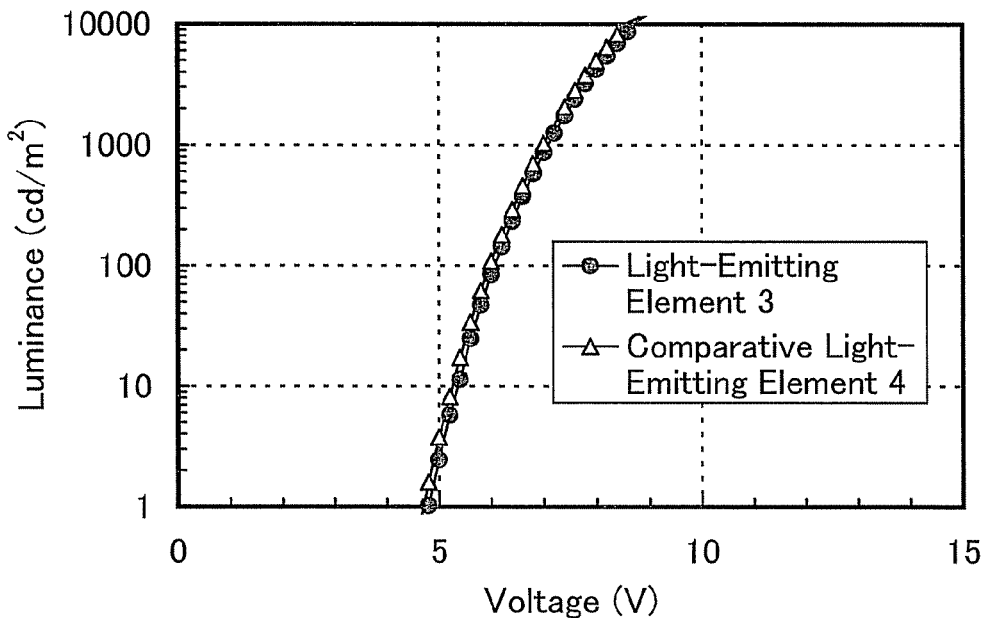
FIG. 13 shows voltage-luminance characteristics of a light-emitting element of Example 3.
Figure 14:
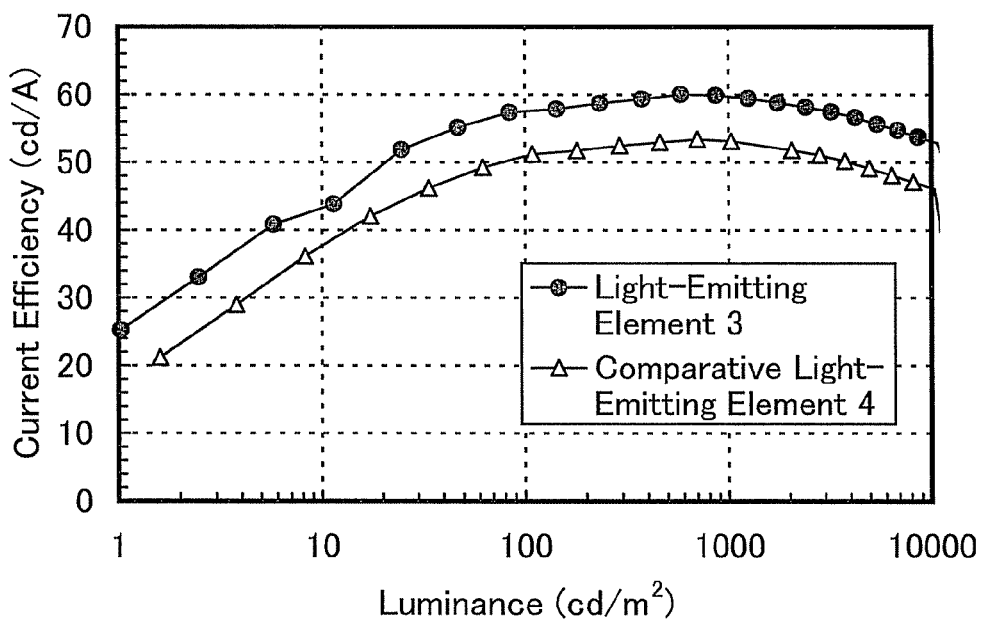
FIG. 14 shows luminance-current efficiency characteristics of a light-emitting element of Example 3.

FIG. 13 shows the voltage-luminance characteristics of Light-Emitting Element 3 and Comparative Light-Emitting Element 4. In FIG. 13, the horizontal axis represents voltage (V) and the vertical axis represents luminance ($cd/m^2$). FIG. 14 shows the luminance-current efficiency characteristics. In FIG. 14, the horizontal axis represents luminance ($cd/m^2$) and the vertical axis represents current efficiency (cd/A). Further, Table 4 shows the voltage (V), current density ($mA/cm^2$), CIE chromaticity coordinates (x, y), luminance ($cd/m^2$), current efficiency (cd/A), and external quantum efficiency (%) of each light-emitting element at a luminance of around 1000 $cd/m^2$.

This can be attributed to a composite material including a heterocyclic compound of one embodiment of the present invention which is a material having a high hole-injection property and a high hole-transport property. It can also be attributed to a sufficiently high LUMO level of a heterocyclic compound of one embodiment of the present invention and suppressed passage of electrons through a light-emitting layer. It can also be attributed to a sufficiently low HOMO level and an excellent property of injecting holes into a light-emitting layer.

Example 4

《Synthesis Example 2》

This example gives descriptions of a method of synthesizing 4,4'-(biphenyl-2,2'-diyl)-bis-(2,8-diphenyldibenzothiophene) (abbreviation: oDBTBP-III), which is a heterocyclic compound of one embodiment of the present invention, represented by the structural formula (102) in Embodiment 1.

TABLE 4

| | Voltage (V) | Current density ($mA/cm^2$) | Chrometicity coordinate x | Chrometicity coordinate y | Luminance ($cd/m^2$) | Current efficiency (cd/A) | Power efficiency (lm/W) | Energy efficiency (%) | External quantum efficiency (%) |
|---|---|---|---|---|---|---|---|---|---|
| Light emitting element 3 | 7.0 | 1.4 | 0.34 | 0.61 | 900 | 60 | 27 | 5.6 | 17 |
| Comparative light emitting element 4 | 7.0 | 1.9 | 0.35 | 0.61 | 1000 | 53 | 24 | 4.9 | 15 |

Figure 15:
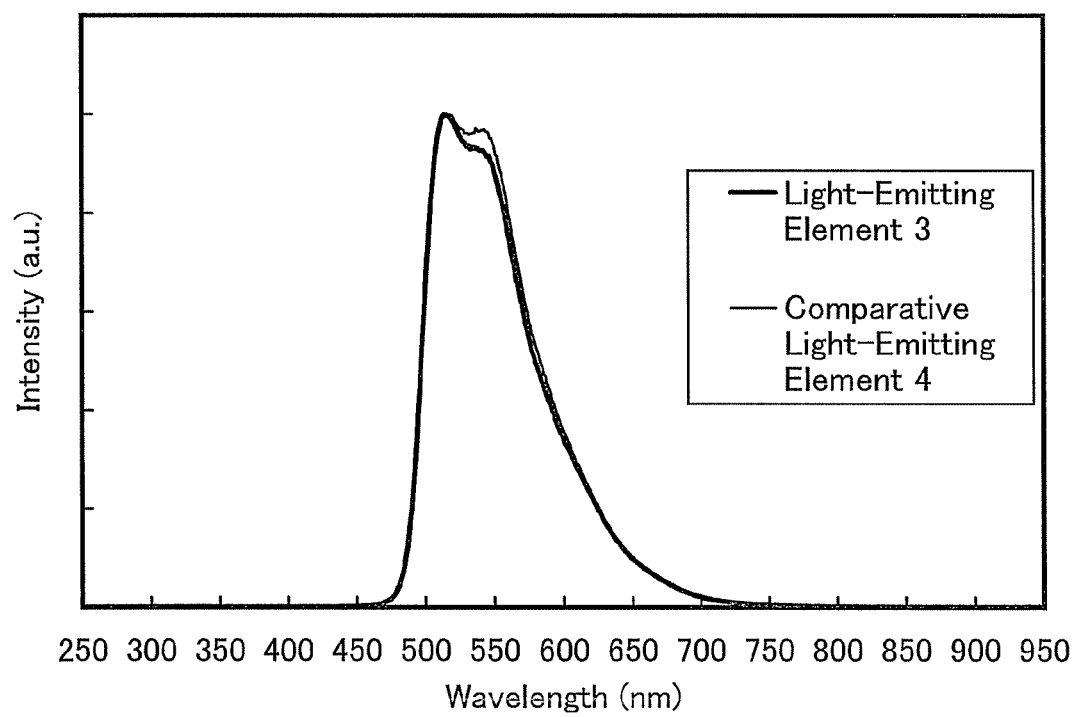
FIG. 15 shows an emission spectrum of a light-emitting element of Example 3.

FIG. 15 shows the emission spectrum of each light-emitting element which was obtained by applying a current at a current density of 0.1 $mA/cm^2$. In FIG. 15, the horizontal axis represents wavelength (nm) and the vertical axis represents intensity (arbitrary unit). As shown in FIG. 15, the emission spectrum of Light-Emitting Element 3 has a peak at 514 nm, and the emission spectrum of Comparative Light-Emitting Element 4 has a peak at 518 nm. In addition, as shown in Table 4, the CIE chromaticity coordinates of Light-Emitting Element 3 at a luminance of 900 $cd/m^2$ were (x, y)=(0.34, 0.61) and the CIE chromaticity coordinates of Comparative Light-Emitting Element 4 at a luminance of 1000 $cd/m^2$ were (x, y)=(0.35, 0.61). It is found that green light emission originating from Ir(ppy)$_3$ was obtained from Light-emitting Element 3 and Comparative Light-Emitting Element 4.

As can be seen from FIG. 14 and Table 4, Light-Emitting Element 3 exhibits higher emission efficiency than Comparative Light-Emitting Element 4.

The above results suggest that a heterocyclic compound of one embodiment of the present invention can be favorably used for a hole-transport layer of a light-emitting element which includes a green phosphorescent compound in a light-emitting layer. The results also suggest that a composite material formed by combining a heterocyclic compound of one embodiment of the present invention and an electron acceptor (an acceptor) can be favorably used for a hole-injection layer.

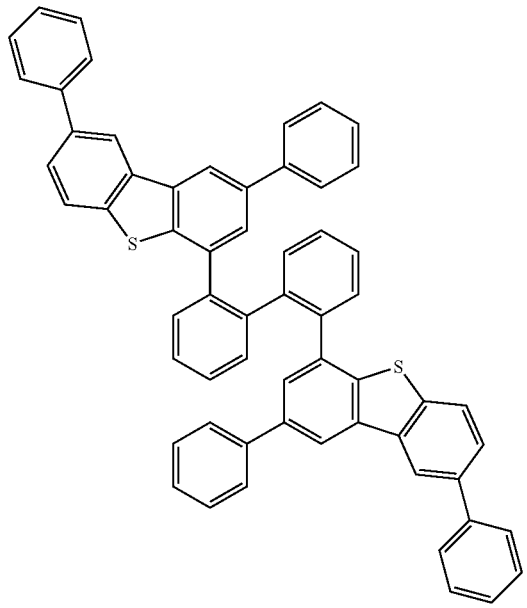

oDBTBP-III

To a 100 mL three-neck flask were added 0.3 g (1.0 mmol) of 2,2'-dibromobiphenyl, 0.8 g (2.2 mmol) of 2,8-diphenyldibenzothiophene-4-boronic acid, 22 mg (0.1 mmol) of palladium(II)acetate, 60 mg (0.2 mmol) of tri(ortho-tolyl)

phosphine, 20 mL of toluene, 2 mL of ethanol, and 2.5 mL of a 2 mol/L aqueous potassium carbonate solution. This mixture was degassed while being stirred under reduced pressure, and was then reacted by being heated and stirred under a nitrogen atmosphere at 90° C. for 5 hours.

After the reaction, toluene was added to this reaction mixture solution, and the mixture was filtered to remove the aqueous layer. Then, the obtained organic layer was purified by silica gel column chromatography (with a developing solvent of toluene and hexane in a 1:3 ratio). The obtained fraction was concentrated, and acetone and methanol were added thereto. The mixture was irradiated with ultrasonic waves and then recrystallized. Part of the obtained powder was separated by high performance liquid chromatography (abbreviation: HPLC) to give a white powder which was the object of the synthesis. A reaction scheme of the above synthesis method is illustrated in the following (C-1).

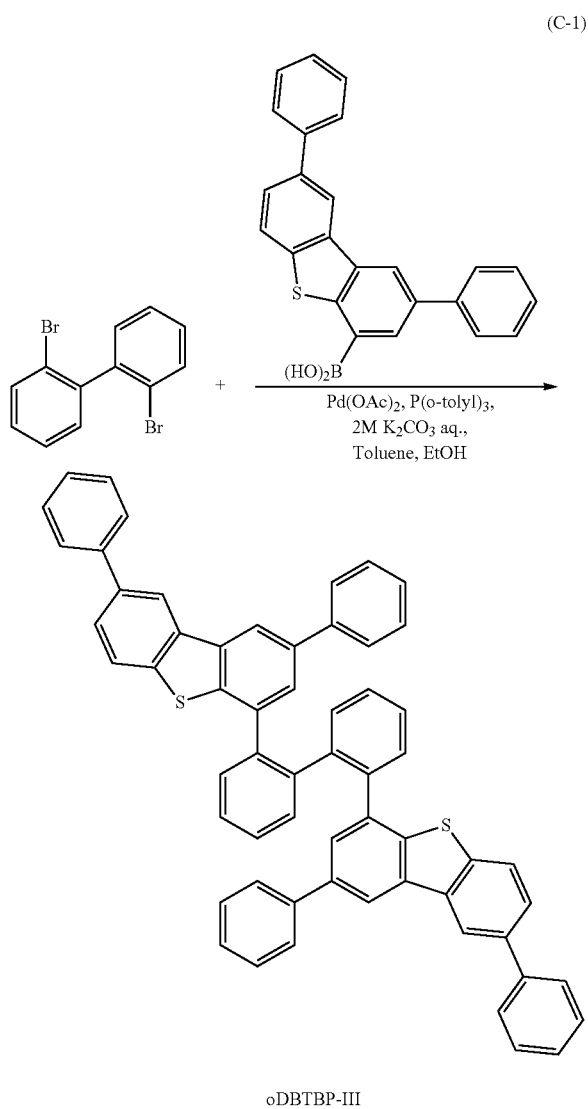

oDBTBP-III

The Rf values of the object of the synthesis and 2,2'-dibromobiphenyl were respectively 0.42 and 0.73, which were found by silica gel thin layer chromatography (TLC) (with a developing solvent of ethyl acetate and hexane in a 1:10 ratio).

Figure 16A:
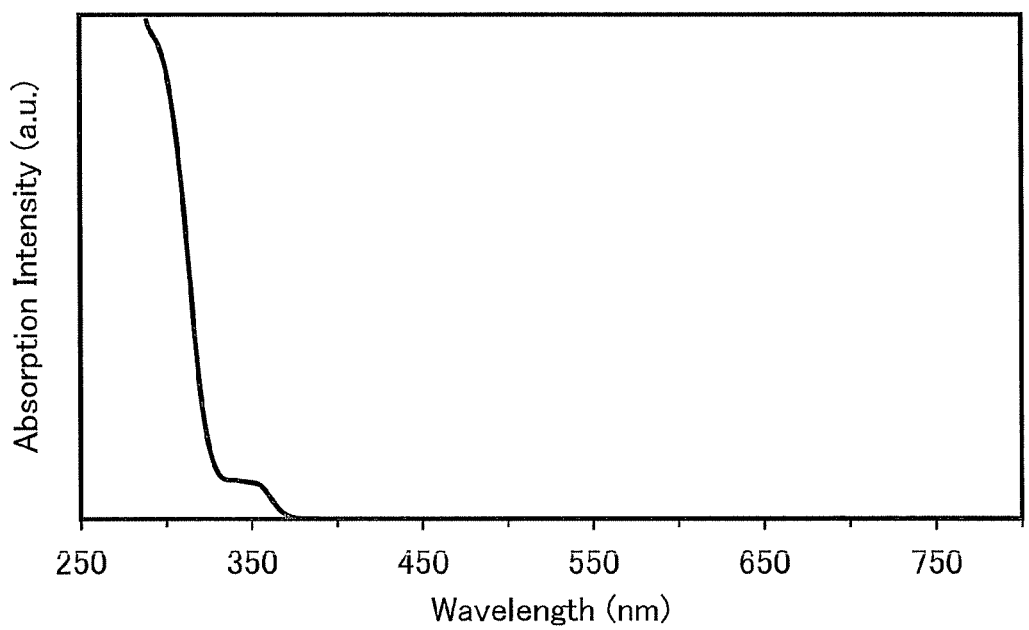
FIGS. 16A and 16B show an absorption spectrum and an emission spectrum of oDBTBP-III in a toluene solution of oDBTBP-III.
Figure 16B:
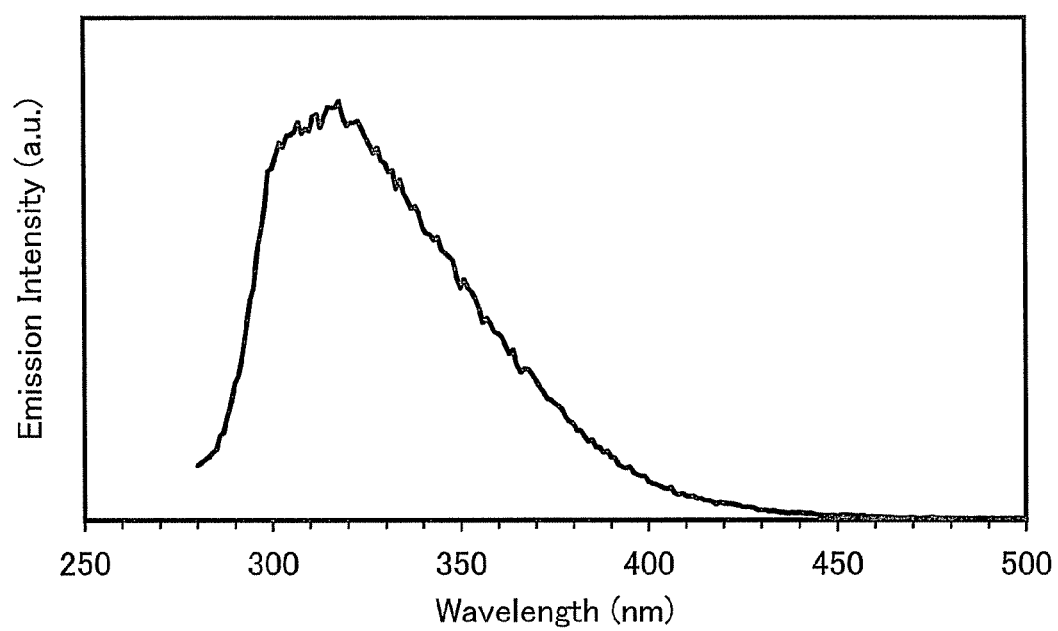

Further, FIG. 16A shows the absorption spectrum of oDBTBP-III in a toluene solution of oDBTBP-III, and FIG. 16B shows the emission spectrum thereof. An ultraviolet-visible spectrophotometer (V-550, manufactured by JASCO Corporation) was used for the measurements. A sample was prepared in such a way that the solution was put in a quartz cell. Here is shown the absorption spectrum which was obtained by subtracting the absorption spectra of quartz and toluene from those of quartz and the solution. In FIG. 16A, the horizontal axis represents wavelength (nm) and the vertical axis represents absorption intensity (arbitrary unit). In FIG. 16B, the horizontal axis represents wavelength (nm) and the vertical axis represents emission intensity (arbitrary unit). In the case of the toluene solution, an absorption peak was found at around 355 nm, and a peak of the emission wavelength was at 318 nm (at an excitation wavelength of 300 nm). FIG. 16A shows that oDBTBP-III is a substance having weak absorption in the visible region. In other words, it is suggested that in the case where oDBTBP-III which is a heterocyclic compound of one embodiment of the present invention is used for a light-emitting element, visible light emitted from a light-emitting layer is unlikely to be reabsorbed by oDBTBP-III, and thus a decrease in light extraction efficiency of the element can be suppressed.

The molecular weight of the compound obtained by the above synthesis method was measured by a TOF-MS detector (Waters Micromass LCT Premier, manufactured by Waters). A mixture solution containing acetonitrile and a 0.1% formic acid solution (mixture rate of acetonitrile and the formic acid solution, 80/20 vol/vol) was used as a solvent. According to the measurement, it was confirmed that a main peak with a molecular weight of 823 (mode was ES+) was detected and oDBTBP-III that was the object of the synthesis was obtained.

Example 5

《Synthesis Example 3》

This example gives descriptions of a method of synthesizing 4,4'-{(1,1':2',1":2",1''')-quaterphenyl-3,3'''-yl}bisdibenzothiophene (abbreviation: mZ-DBT2-II), which is a heterocyclic compound of one embodiment of the present invention, represented by the structural formula (114) in Embodiment 1.

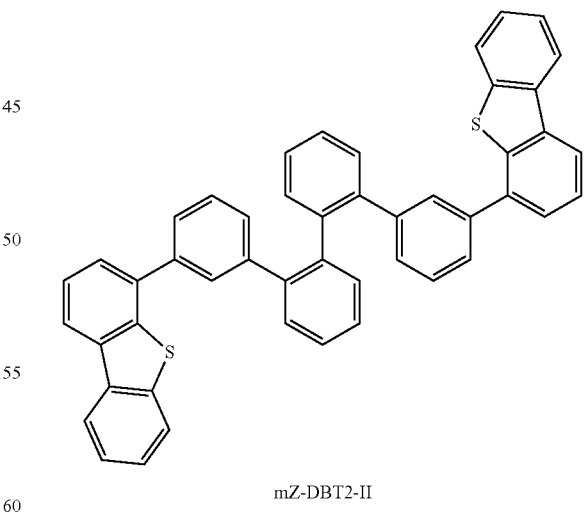

mZ-DBT2-II

In a 200 mL three-neck flask, a mixture of 1.0 g (3.2 mmol) of 2,2'-dibromobiphenyl, 2.1 g (6.7 mmol) of 3-(dibenzothiophen-4-yl)-phenylboronic acid, 47 mg (40 μmol) of tetrakis(triphenylphosphine)palladium(0), 20 mL of toluene, 2 mL of ethanol, 7 mL of a 2 mol/L aqueous potassium carbonate solution was degassed while being stirred under reduced pressure, and was then reacted by being heated and stirred under a nitrogen atmosphere at 85° C. for 6 hours and then by being heated and stirred at 100° C. for 6 hours. Further, 47 mg (40 μmol) of tetrakis(triphenylphosphine)palladium(0) was added to the mixture, and the mixture was reacted by being heated and stirred under a nitrogen atmosphere at 100° C. for 2 hours.

After the reaction, 300 mL of toluene was added to this reaction mixture solution, and the organic layer of the mixture solution was filtered through Florisil (produced by Wako Pure Chemical Industries, Ltd., Catalog No. 540-00135), alumina (produced by Merck & Co., Inc., neutral), and Celite (produced by Wako Pure Chemical Industries, Ltd., Catalog No. 531-16855). The obtained filtrate was washed with water, and magnesium sulfate was added thereto so that moisture was adsorbed. This suspension was filtered to obtain a filtrate. The obtained filtrate was concentrated and purified by silica gel column chromatography. At this time, a mixed solvent of toluene and hexane (toluene:hexane=1:5) was used as a developing solvent for the chromatography. The obtained fraction was concentrated, and hexane was added thereto. The mixture was irradiated with ultrasonic waves and then recrystallized to give 2.2 g of a white powder in a yield of 51%, which was the object of the synthesis. A reaction scheme of the above synthesis method is illustrated in the following (D-1).

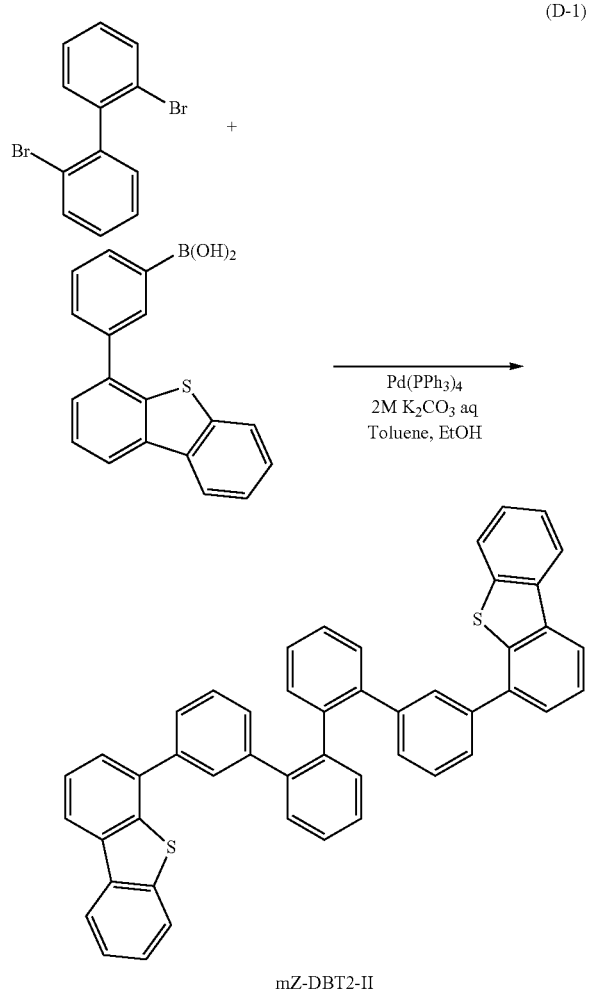

(D-1)

mZ-DBT2-II

The Rf value of the substance that was the object of the synthesis was 0.25, which was found by silica gel thin layer chromatography (TLC) (with a developing solvent of ethyl acetate and hexane in a 1:10 ratio).

This compound was identified as mZ-DBT2-II, which was the object of the synthesis, by nuclear magnetic resonance (NMR) spectroscopy.

$^1$H NMR data of the obtained compound are as follows: $^1$H NMR (CDCl$_3$, 300 MHz): δ (ppm)=6.73 (td, J=0.98 Hz, 1.95 Hz, 7.4 Hz, 2H), 7.01-7.06 (m, 4H), 7.34-7.39 (m, 4H), 7.41-7.47 (m, 11H), 7.53-7.59 (m, 3H), 7.69-7.72 (m, 2H), 7.98 (dd, J=1.5 Hz, 6.8 Hz, 2H), 8.08-8.11 (m, 2H).

Figure 17A:
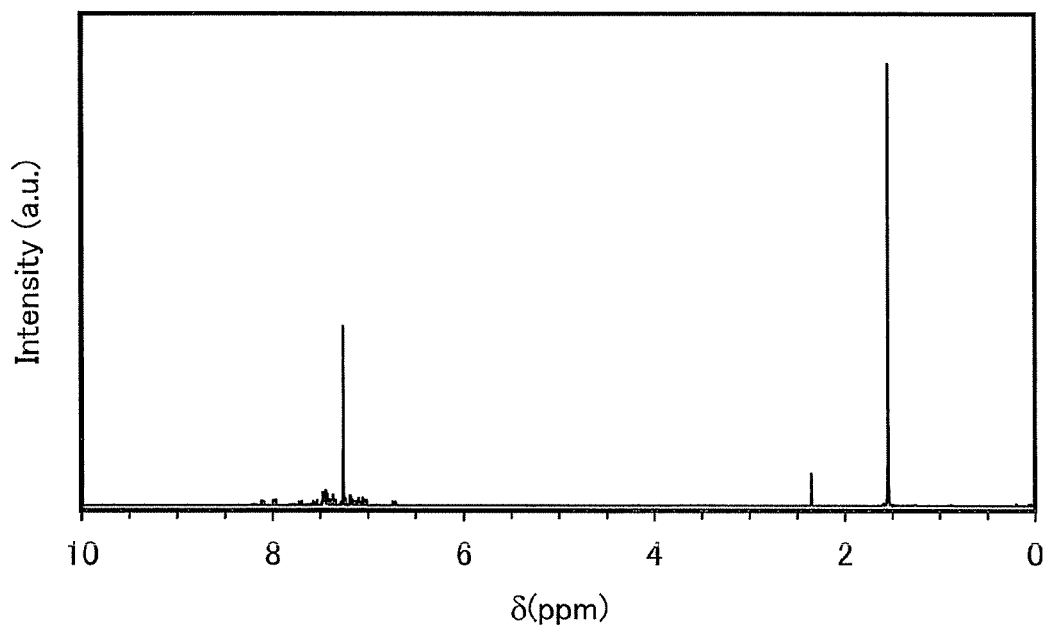
FIGS. 17A and 17B show $^1$H NMR charts of mZ-DBT2-II.
Figure 17B:
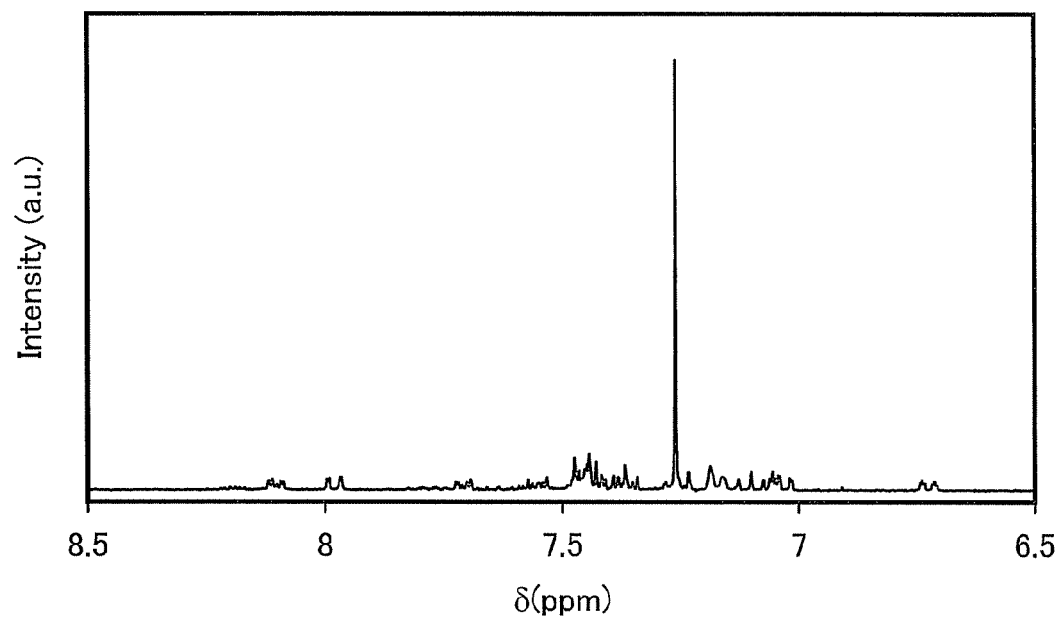

Further, the $^1$H NMR charts are shown in FIGS. 17A and 17B. Note that FIG. 17B is a chart where the range of from 6.5 ppm to 8.5 ppm in FIG. 17A is enlarged.

Figure 18A:
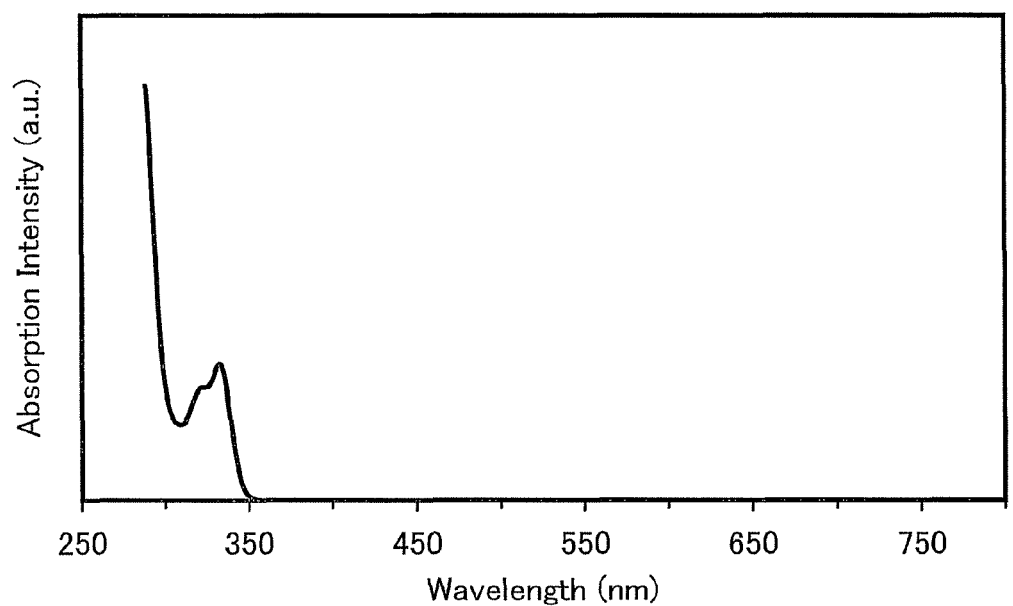
FIGS. 18A and 18B show an absorption spectrum and an emission spectrum of mZ-DBT2-II in a toluene solution of mZ-DBT2-II.
Figure 18B:
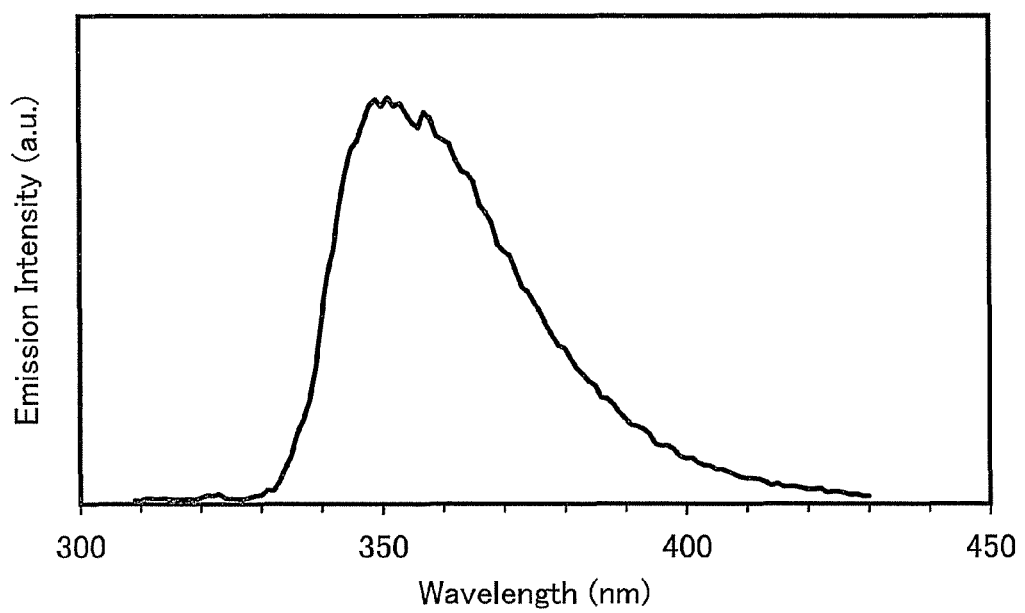

Further, FIG. 18A shows the absorption spectrum of mZ-DBT2-II in a toluene solution of mZ-DBT2-II, and FIG. 18B shows the emission spectrum thereof. An ultraviolet-visible spectrophotometer (V-550, manufactured by JASCO Corporation) was used for the measurements. A sample was prepared in such a way that the solution was put in a quartz cell. Here is shown the absorption spectrum which was obtained by subtracting the absorption spectra of quartz and toluene from those of quartz and the solution. In FIG. 18A, the horizontal axis represents wavelength (nm) and the vertical axis represents absorption intensity (arbitrary unit). In FIG. 18B, the horizontal axis represents wavelength (nm) and the vertical axis represents emission intensity (arbitrary unit). In the case of the toluene solution, an absorption peak was found at around 331 nm, and a peak of the emission wavelength was at 351 nm (at an excitation wavelength of 292 nm). FIG. 18A shows that mZ-DBT2-II is a substance having weak absorption in the visible region. In other words, it is suggested that in the case where mZ-DBT2-II which is a heterocyclic compound of one embodiment of the present invention is used for a light-emitting element, visible light emitted from a light-emitting layer is unlikely to be reabsorbed by mZ-DBT2-II, and thus a decrease in light extraction efficiency of the element can be suppressed.

Example 6

In this example, a light-emitting element of one embodiment of the present invention will be described with reference to FIG. 9B. The structural formulae of materials used in this example are illustrated below. Note that the structural formulae of materials which are already illustrated will be omitted.

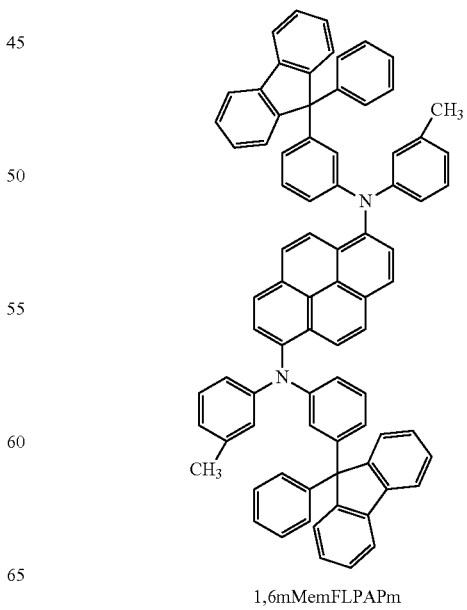

1,6mMemFLPAPm

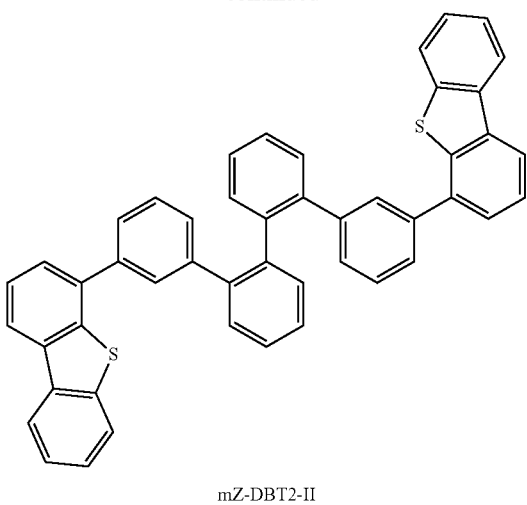 [SMILES: c1cc(-c2ccccc2-c2ccccc2-c2cccc(-c3cccc4c3sc3ccccc34)c2)cc(-c2cccc3c2sc2ccccc23)c1]

mZ-DBT2-II

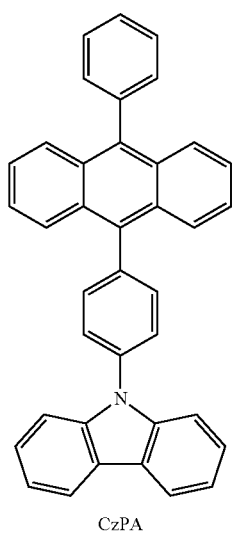

CzPA

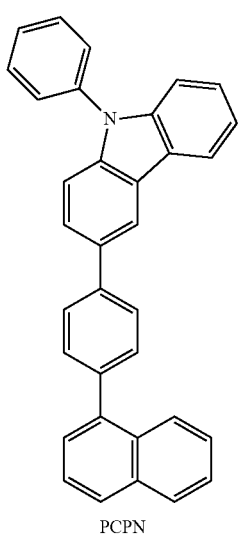

PCPN

A method for manufacturing Light-Emitting Element 5 of this example will be described below.

(Light-Emitting Element 5)

First, in a manner similar to Light-Emitting Element 3 described in Example 3, a film of ITSO was formed over a glass substrate 1100 to form a first electrode 1101.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about $10^{-4}$ Pa. Then, 4,4'-{(1,1':2',1":2",1'")-quaterphenyl-3,3'''-yl}bisdibenzothiophene (abbreviation: mZ-DBT2-II) and molybdenum(VI) oxide were co-evaporated to form a hole-injection layer 1111 over the first electrode 1101. The thickness of the hole-injection layer 1111 was set to 50 nm, and the weight ratio of mZ-DBT2-II to molybdenum(VI) oxide was adjusted to 4:2 (=mZ-DBT2-II:molybdenum oxide).

Next, over the hole-injection layer 1111, a film of 3-[4-(1-naphthyl)-phenyl]-9-phenyl-9H-carbazole (abbreviation: PCPN) was formed to a thickness of 10 nm to form a hole-transport layer 1112.

Furthermore, 9-[4-(10-phenyl-9-anthryl)phenyl]-9H-carbazole (abbreviation: CzPA) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) were co-evaporated to form a light-emitting layer 1113 over the hole-transport layer 1112. Here, the mass ratio of CzPA to 1,6mMemFLPAPrn was adjusted to 1:0.04 (=CzPA:1, 6mMemFLPAPrn). In addition, the thickness of the light-emitting layer 1113 was set to 30 nm.

Further, over the light-emitting layer 1113, a film of CzPA was formed to a thickness of 10 nm to form a first electron-transport layer 1114a.

Then, over the first electron-transport layer 1114a, a BPhen film was formed to a thickness of 15 nm to form a second electron-transport layer 1114b.

Further, over the second electron-transport layer 1114b, a LiF film was formed by evaporation to a thickness of 1 nm to form an electron-injection layer 1115.

Lastly, an aluminum film was formed by evaporation to a thickness of 200 nm as a second electrode 1103 functioning as a cathode. Thus, Light-Emitting Element 5 of this example was fabricated.

Note that, in the above evaporation steps, evaporation was all performed by a resistance heating method.

Table 5 shows an element structure of Light-Emitting Element 5 obtained as described above.

TABLE 5

| | First electrode | Hole injection layer | Hole transport layer | Light-emitting layer | First electron transport layer | Second electron transport layer | Electron injection layer | Second electrode |
|---|---|---|---|---|---|---|---|---|
| Light emitting element 5 | ITSO 110 nm | mZ-DBT2-II:MoOx (=4:2) 50 nm | PCPN 10 nm | CzPA:1,6mMemFLPAPrn (=1:0.04) 30 nm | CzPA 10 nm | BPhen 15 nm | LiF 1 nm | Al 200 nm |

In a glove box containing a nitrogen atmosphere, Light-Emitting Element 5 was sealed so as not to be exposed to air. Then, operation characteristics of Light-Emitting Element 5 were measured. Note that the measurements were carried out at room temperature (in the atmosphere kept at 25° C.).

Figure 19:
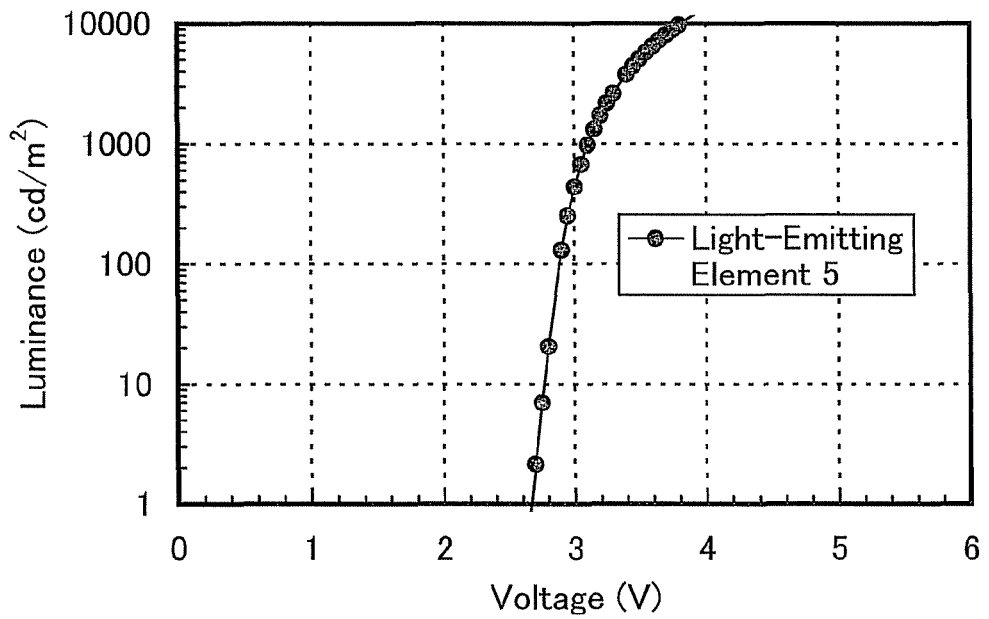
FIG. 19 shows voltage-luminance characteristics of a light-emitting element of Example 6.
Figure 20:
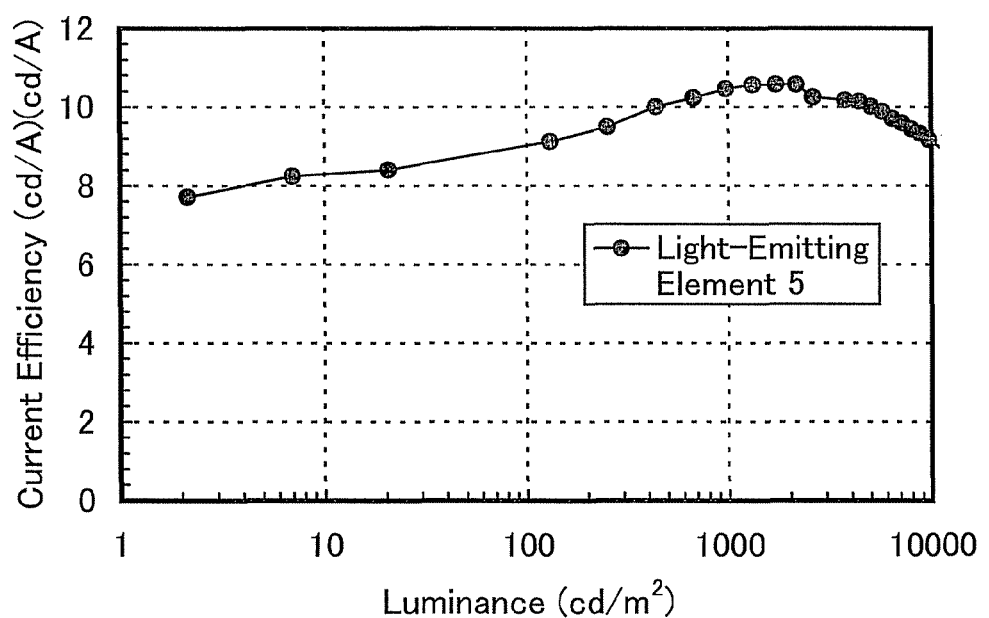
FIG. 20 shows luminance-current efficiency characteristics of a light-emitting element of Example 6.

FIG. 19 shows the voltage-luminance characteristics of Light-Emitting Element 5. In FIG. 19, the horizontal axis represents voltage (V) and the vertical axis represents luminance (cd/m$^2$). FIG. 20 shows the luminance-current efficiency characteristics. In FIG. 20, the horizontal axis represents luminance (cd/m$^2$) and the vertical axis represents current efficiency (cd/A). Further, Table 6 shows the voltage (V), CIE chromaticity coordinates (x, y), current efficiency (cd/A), and external quantum efficiency (%) of Light-Emitting Element 5 at a luminance of 1000 cd/m$^2$.

TABLE 6

| | Voltage | Current density | Chromaticity coordinate | | Current efficiency | Power efficiency | External quantum efficiency |
|---|---|---|---|---|---|---|---|
| | (V) | (mA/cm$^2$) | x | y | (cd/A) | (lm/W) | (%) |
| Light emitting element 5 | 3.1 | 9.3 | 0.14 | 0.16 | 10 | 11 | 8.8 |

As shown in Table 6, the CIE chromaticity coordinates of Light-Emitting Element 5 were (x, y)=(0.14, 0.16) at a luminance of 1000 cd/m$^2$. The results show that blue light emission originating from 1,6-mMemFLPAPrn was obtained from Light-Emitting Element 5.

As can be seen from FIG. 19, FIG. 20, and Table 6, Light-Emitting Element 5 exhibits high emission efficiency. It can also be seen that Light-Emitting Element 5 is a light-emitting element having low driving voltage.

Figure 21:
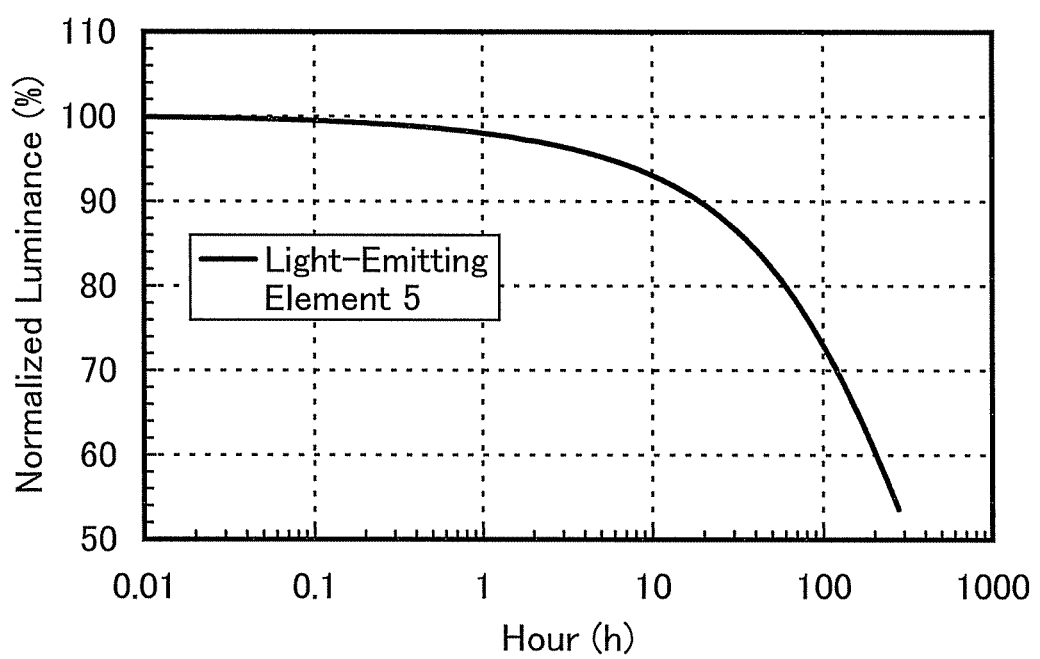
FIG. 21 shows results of reliability tests of a light-emitting element of Example 6.

Next, Light-Emitting Element 5 was subjected to reliability tests. Results of the reliability tests are shown in FIG. 21. In FIG. 21, the vertical axis represents normalized luminance (%) with an initial luminance of 100%, and the horizontal axis represents driving time (h) of the element.

In the reliability tests, Light-Emitting Element 5 was driven under the conditions where the initial luminance was set to 5000 cd/m$^2$ and the current density was constant.

FIG. 21 shows that Light-Emitting Element 5 kept 54% of the initial luminance after the driving for 280 hours.

The above results suggest that an element having high emission efficiency can be realized by use of a composite material formed by combining a heterocyclic compound of one embodiment of the present invention and an electron acceptor (an acceptor) for a hole-injection layer of the light-emitting element. The results also suggest that a light-emitting element having low driving voltage can be provided by use of the composite material for a hole-injection layer of the light-emitting element. The results also suggest that a light-emitting element having a long lifetime can be manufactured by use of the composite material for a hole-injection layer.

Reference Example 1

A method of synthesizing 2-[4-(dibenzothiophen-4-yl)phenyl]-1-phenyl-1H-benzimidazole (abbreviation: DBT-BIm-II) used in the above example will be described.

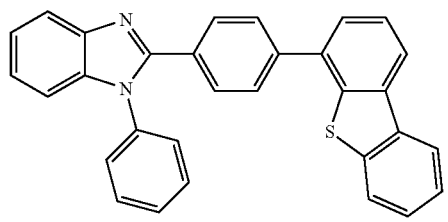

DBTBIm-II

《Synthesis of 2-[4-(dibenzothiophen-4-yl)phenyl]-1-phenyl-1H-benzimidazole (abbreviation: DBT-BIm-II)》

A synthesis scheme of 2-[4-(dibenzothiophen-4-yl)phenyl]-1-phenyl-1H-benzimidazole (abbreviation: DBTBIm-II) is illustrated in (x-1).

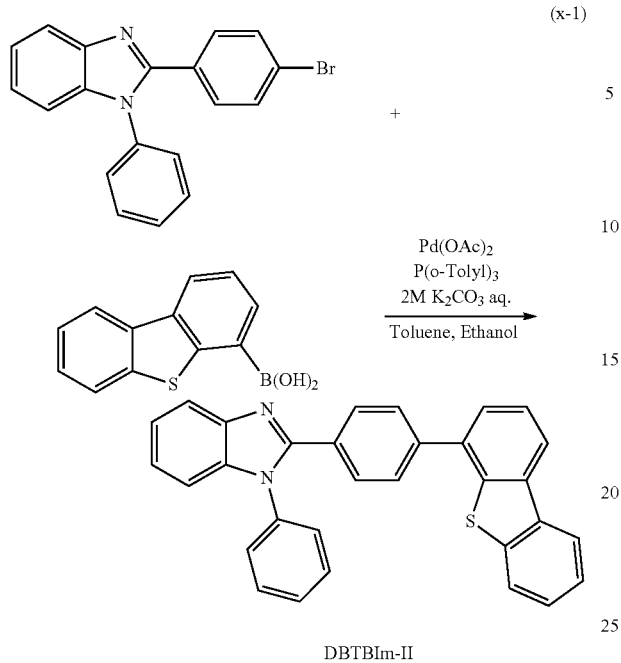

DBTBIm-II

In a 500 mL three-neck flask were put 5.1 g (15 mmol) of 2-(4-bromophenyl)-1-phenyl-1H-benzimidazole, 3.7 g (16 mmol) of dibenzothiophene-4-boronic acid, and 0.2 g (0.7 mmol) of tri(ortho-tolyl)phosphine. The air in the flask was replaced with nitrogen. To this mixture were added 16 mL of a 2.0 mmol/L aqueous potassium carbonate solution, 55 mL of toluene, and 18 mL of ethanol. Then, 33 mg (0.2 mmol) of palladium(II)acetate was added to this mixture, and the mixture was stirred under a nitrogen stream at 80° C. for 6 hours.

After a predetermined time elapsed, water was added to the obtained mixture, and an organic substance was extracted from the aqueous layer with chloroform. The solution of the extract and the organic layer were combined and washed with a saturated aqueous sodium chloride solution, and dried with magnesium sulfate. This mixture was gravity filtered. The obtained filtrate was concentrated to give an oily substance. This oily substance was purified by silica gel column chromatography. The silica gel column chromatography was carried out using toluene as a developing solvent. The obtained fraction was concentrated to give a solid. Hexane was added to this solid, followed by irradiation with ultrasonic waves. The solid was suction filtered to give 5.8 g of a white powder in a yield of 88%, which was the object of the synthesis.

2.8 g of the obtained white powder was sublimated and purified by a train sublimation method. In the sublimation purification, the white powder was heated at 235° C. under a pressure of 2.4 Pa with a flow rate of argon gas of 5 mL/min. After the sublimation purification, 2.2 g of a light-yellow glassy solid was obtained in a yield of 79%.

This compound was identified as 2-[4-(dibenzothiophen-4-yl)phenyl]-1-phenyl-1H-benzimidazole (abbreviation: DBTBIm-II), which was the object of the synthesis, by nuclear magnetic resonance (NMR) spectroscopy.

$^1$H NMR data of the obtained substance are as follows: $^1$H NMR (CDCl$_3$, 300 MHz): δ (ppm)=7.27-7.30 (m, 2H), 7.32-7.60 (m, 10H), 7.67-7.75 (m, 4H), 7.82-7.85 (m, 1H), 7.83 (dd, J=8.4 Hz, 1.5 Hz, 1H), 8.13-8.19 (m, 2H).

Reference Example 2

A method of synthesizing 4-phenyl-4'-(9-phenylfluoren-9-yl)triphenylamine (abbreviation: BPAFLP) used in the above example will be specifically described. A structure of BPAFLP is shown below.

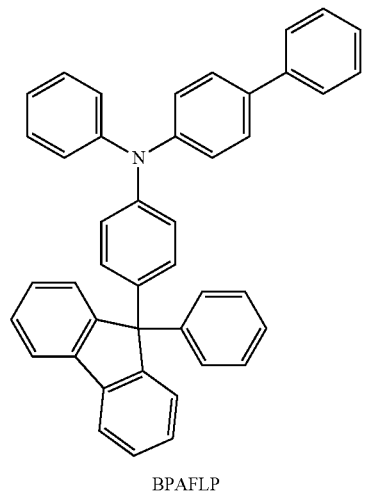 [SMILES: c1ccc(-c2ccc(N(c3ccccc3)c3ccc(C4(c5ccccc5)c5ccccc5-c5ccccc54)cc3)cc2)cc1]

BPAFLP

《Step 1: Method of Synthesizing 9-(4-bromophenyl)-9-phenylfluorene》

In a 100 mL three-neck flask, 1.2 g (50 mmol) of magnesium was activated by being heated and stirred for 30 minutes under reduced pressure. The activated magnesium was cooled to room temperature, and the flask was made to contain a nitrogen atmosphere. Then, several drops of dibromoethane were added, so that foam formation and heat generation were confirmed. After 12 g (50 mmol) of 2-bromobiphenyl dissolved in 10 mL of diethyl ether was slowly added dropwise to this mixture, the mixture was heated and stirred under reflux for 2.5 hours, so that a Grignard reagent was prepared.

In a 500 mL three-neck flask were placed 10 g (40 mmol) of 4-bromobenzophenone and 100 mL of diethyl ether. After the Grignard reagent which was synthesized in advance was slowly added dropwise to this mixture, the mixture was heated and stirred under reflux for 9 hours.

After reaction, this mixture solution was filtered to give a residue. The obtained residue was dissolved in 150 mL of ethyl acetate, and 1N-hydrochloric acid was added to the mixture until it was made acid, which was then stirred for 2 hours. The organic layer of this liquid was washed with water, and magnesium sulfate was added thereto to remove moisture. This suspension was filtered, and the obtained filtrate was concentrated to give a highly viscous substance.

In a 500 mL recovery flask were placed this highly viscous substance, 50 mL of glacial acetic acid, and 1.0 mL of hydrochloric acid. The mixture was reacted by being stirred and heated at 130° C. for 1.5 hours under a nitrogen atmosphere.

After the reaction, this reaction mixture solution was filtered to give a residue. The obtained residue was washed with water, an aqueous sodium hydroxide solution, water, and methanol in this order. Then, the mixture was dried, so that the substance which was the object of the synthesis was obtained as 11 g of a white powder in a 69% yield. A reaction scheme of the above synthesis method is illustrated in the following (y-1).

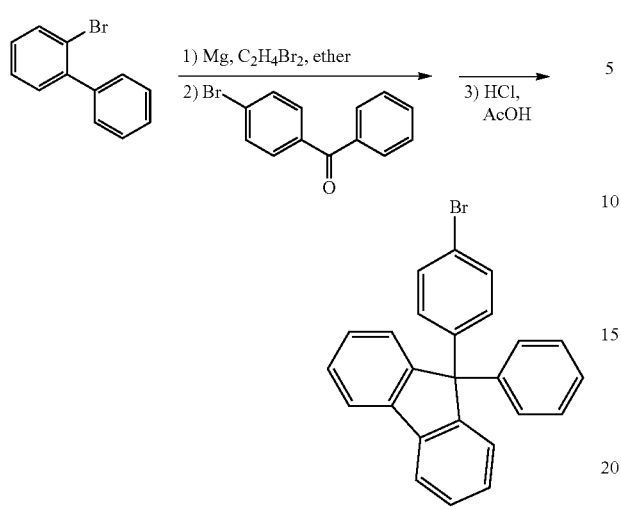

(y-1)

«Step 2: Method of Synthesizing 4-Phenyl-4'-(9-phenylfluoren-9-yl)triphenylamine (abbreviation: BPAFLP)»

In a 100 mL three-neck flask were placed 3.2 g (8.0 mmol) of 9-(4-bromophenyl)-9-phenylfluorene, 2.0 g (8.0 mmol) of 4-phenyl-diphenylamine, 1.0 g (10 mmol) of sodium tert-butoxide, and 23 mg (0.04 mmol) of bis(dibenzylideneacetone)palladium(0), and the air in the flask was replaced with nitrogen. Then, 20 mL of dehydrated xylene was added to this mixture. After the mixture was degassed while being stirred under reduced pressure, 0.2 mL (0.1 mmol) of tri(tert-butyl) phosphine (a 10 wt % hexane solution) was added to the mixture. This mixture was reacted by being stirred and heated at 110° C. for 2 hours under a nitrogen atmosphere.

After the reaction, 200 mL of toluene was added to this reaction mixture solution, and this suspension was filtered through Florisil (produced by Wako Pure Chemical Industries, Ltd., Catalog. No. 540-00135) and Celite (produced by Wako Pure Chemical Industries, Ltd., Catalog No. 531-16855). The obtained filtrate was concentrated, and the resulting substance was purified by silica gel column chromatography (with a developing solvent of toluene and hexane in a 1:4 ratio). The obtained fraction was concentrated, and acetone and methanol were added thereto. The mixture was irradiated with ultrasonic waves and then recrystallized, so that the substance which was the object of the synthesis was obtained as 4.1 g of a white powder in a 92% yield. A reaction scheme of the above synthesis method is illustrated in the following (y-2).

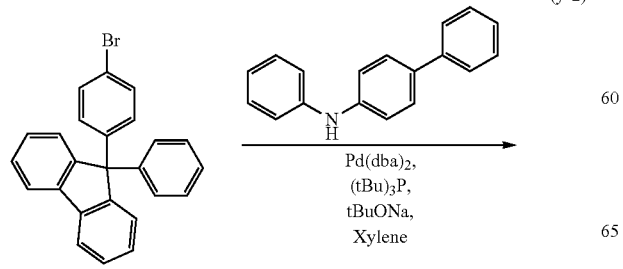

(y-2)

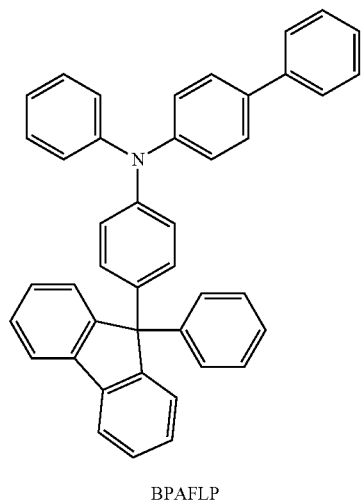

BPAFLP

The Rf values of the substance that was the object of the synthesis, 9-(4-bromophenyl)-9-phenylfluorene, and 4-phenyl-diphenylamine were respectively 0.41, 0.51, and 0.27, which were found by silica gel thin layer chromatography (TLC) (with a developing solvent of ethyl acetate and hexane in a 1:10 ratio).

The compound obtained in Step 2 as described above was subjected to nuclear magnetic resonance (NMR) spectroscopy. The measurement data are shown below. The measurement results indicate that the obtained compound was BPAFLP (abbreviation), which is a fluorene derivative.

$^1$H NMR (CDCl$_3$, 300 MHz): δ (ppm)=6.63-7.02 (m, 3H), 7.06-7.11 (m, 6H), 7.19-7.45 (m, 18H), 7.53-7.55 (m, 2H), 7.75 (d, 3=6.9, 2H).

Reference Example 3

A synthesis example of manufacturing 3-[4-(1-naphthyl)-phenyl]-9-phenyl-9H-carbazole (abbreviation: PCPN) used in the above example will be described.

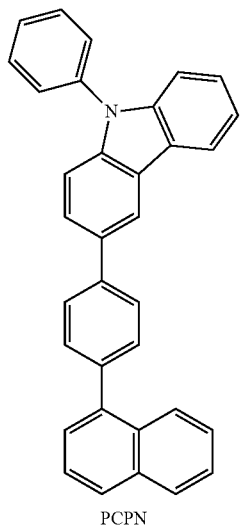

PCPN

A synthesis scheme of PCPN is illustrated in (z-1).

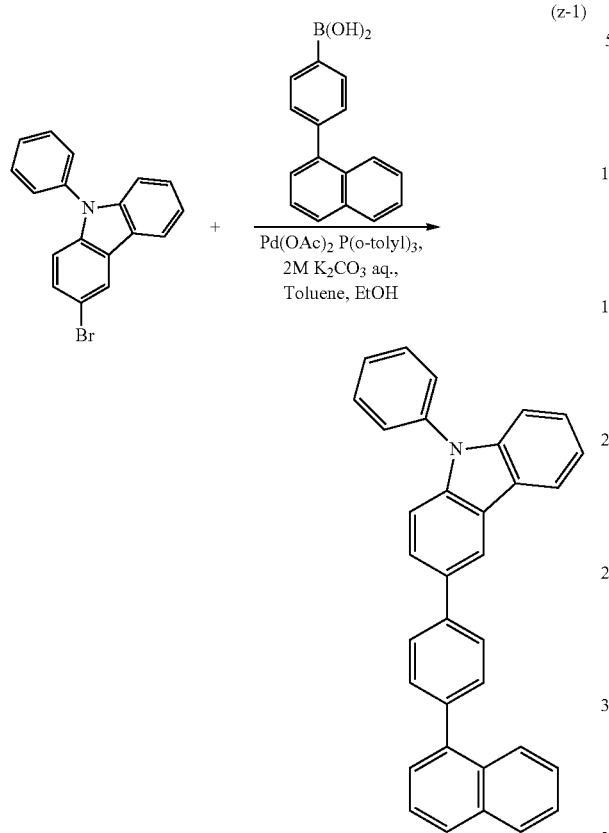

In a 200 mL three-neck flask, a mixture of 5.0 g (15.5 mmol) of 3-bromo-9-phenyl-9H-carbazole, 4.2 g (17.1 mmol) of 4-(1-naphthyl)-phenylboronic acid, 38.4 mg (0.2 mmol) of palladium(II)acetate, 104 mg (0.3 mmol) of tri(ortho-tolyl)phosphine, 50 mL of toluene, 5 mL of ethanol, and 30 mL of a 2 mol/L aqueous potassium carbonate solution was degassed while being stirred under reduced pressure, and reacted by being heated and stirred under a nitrogen atmosphere at 85° C. for 9 hours.

After the reaction, 500 mL of toluene was added to this reaction mixture solution, and the organic layer of this mixture solution was filtered through Florisil (produced by Wako Pure Chemical Industries, Ltd., Catalog No. 540-00135), alumina, and Celite (produced by Wako Pure Chemical Industries, Ltd., Catalog No. 531-16855). The obtained filtrate was washed with water, and magnesium sulfate was added thereto so that moisture was adsorbed. This suspension was filtered to obtain a filtrate. The obtained filtrate was concentrated and purified by silica gel column chromatography. At this time, a mixed solvent of toluene and hexane (toluene:hexane=1:4) was used as a developing solvent for the chromatography. The obtained fraction was concentrated, and methanol was added thereto. The mixture was irradiated with ultrasonic waves and then recrystallized to give 6.24 g of a white powder in a yield of 90%, which was the object of the synthesis.

This compound was identified as 3-[4-(1-naphthyl)-phenyl]-9-phenyl-9H-carbazole (abbreviation: PCPN), which was the object of the synthesis, by nuclear magnetic resonance ($^1$H-NMR) spectroscopy.

$^1$H NMR data of the obtained substance are as follows: $^1$H NMR (CDCl$_3$, 300 MHz): δ (ppm)=7.30-7.35 (m, 1H), 7.44-7.67 (m, 14H), 7.76 (dd, J=8.7 Hz, 1.8 Hz, 1H), 7.84-7.95 (m, 4H), 8.04 (d, J=7.8, 1H), 8.23 (d, J=7.8, 1H), 8.46 (d, J=1.5, 1H).

This application is based on Japanese Patent Application serial no. 2010-201672 filed with Japan Patent Office on Sep. 9, 2010 and Japanese Patent Application serial no. 2011-122799 filed with Japan Patent Office on May 31, 2011, the entire contents of which are hereby incorporated by reference.

The invention claimed is:

1. A heterocyclic compound represented by the following general formula (G1),

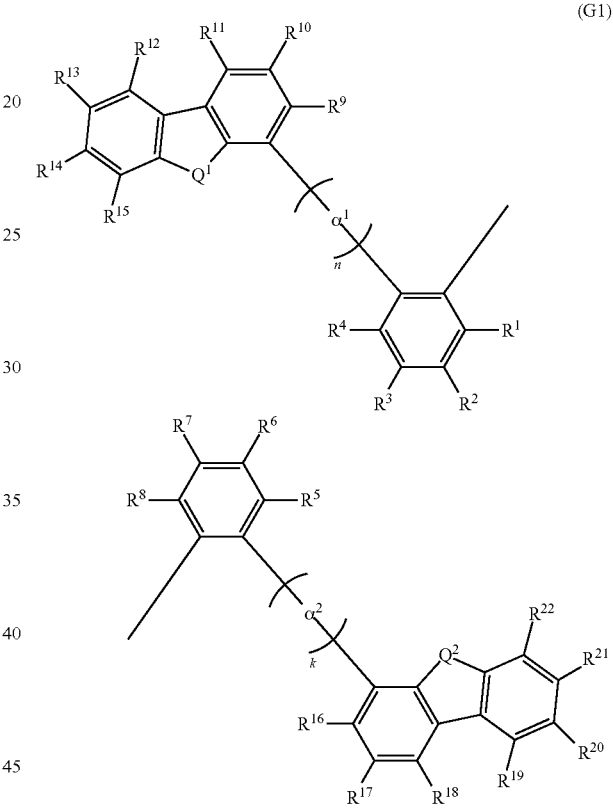

wherein α$^1$ and α$^2$ separately represent a substituted or unsubstituted arylene group having 6 to 13 carbon atoms, wherein n and k separately represent 0 or 1, wherein Q$^1$ and Q$^2$ separately represent sulfur or oxygen, and wherein R$^1$ to R$^{22}$ separately represent hydrogen, an alkyl group having 1 to 12 carbon atoms, or a substituted or unsubstituted aryl group having 6 to 14 carbon atoms.

2. The heterocyclic compound according to claim 1, wherein the R$^1$ to R$^{22}$ are separately represented by any one of the following structural formulae (R-1) to (R-14),

(R-3) 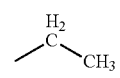

(R-4) 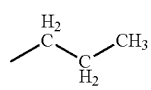

(R-5) 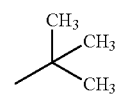

(R-6) 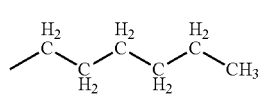

(R-7) 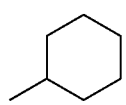

(R-8) 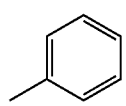

(R-9) 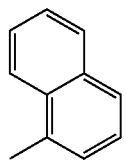

(R-10) 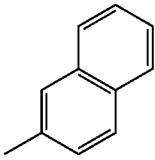

(R-11) 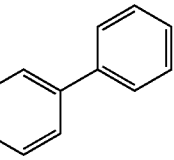

(R-12) 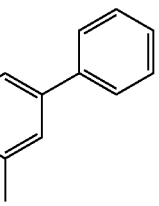

(R-13) 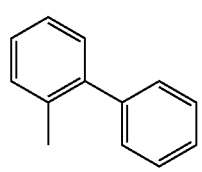

(R-14) 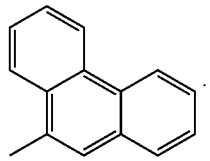

3. The heterocyclic compound according to claim 1, wherein the $\alpha^1$ or the $\alpha^2$ represents an arylene group having 6 to 13 carbon atoms and having one or more substituents, and wherein the one or more substituents are separately an alkyl group having 1 to 12 carbon atoms or an aryl group having 6 to 14 carbon atoms.

4. The heterocyclic compound according to claim 3, wherein the one or more substituents are separately represented by any one of the following structural formulae (R-2) to (R-14), (R-2) 

(R-3) 

(R-4) 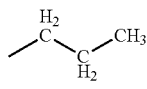

(R-5) 

(R-6) 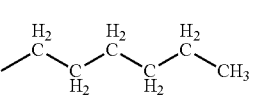

(R-7) 

(R-8) 

(R-9) 

(R-10) 

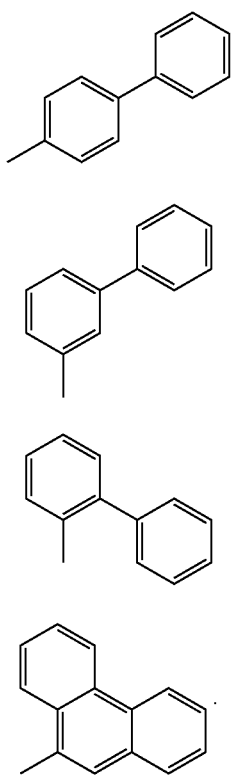
5. The heterocyclic compound according to claim 1, wherein the $\alpha^1$ and the $\alpha^2$ are separately represented by any one of the following structural formulae ($\alpha$-1) to ($\alpha$-11),
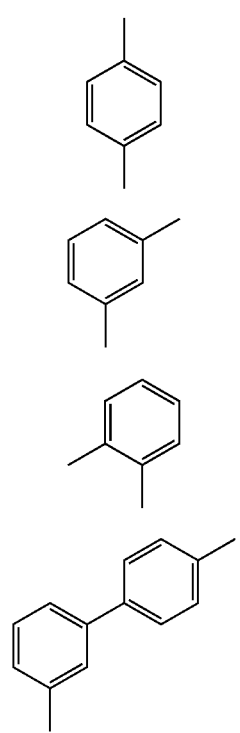
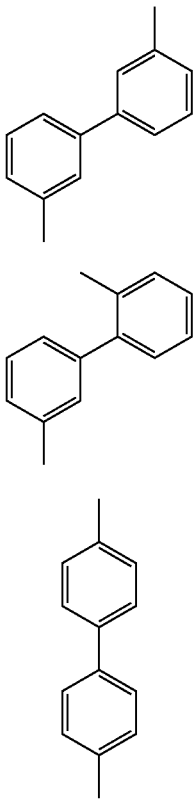
6. A light-emitting element comprising the heterocyclic compound according to claim 1.
7. A light-emitting device comprising the light-emitting element according to claim 6.

8. An electronic device comprising the light-emitting device according to claim 7.

9. A lighting device comprising the light-emitting device according to claim 7.

10. A light-emitting element comprising:
    an anode;
    a cathode;
    a light-emitting layer between the anode and the cathode; and
    a layer comprising a heterocyclic compound represented by the following general formula (G1), the layer comprising the heterocyclic compound between the anode and the light-emitting layer,

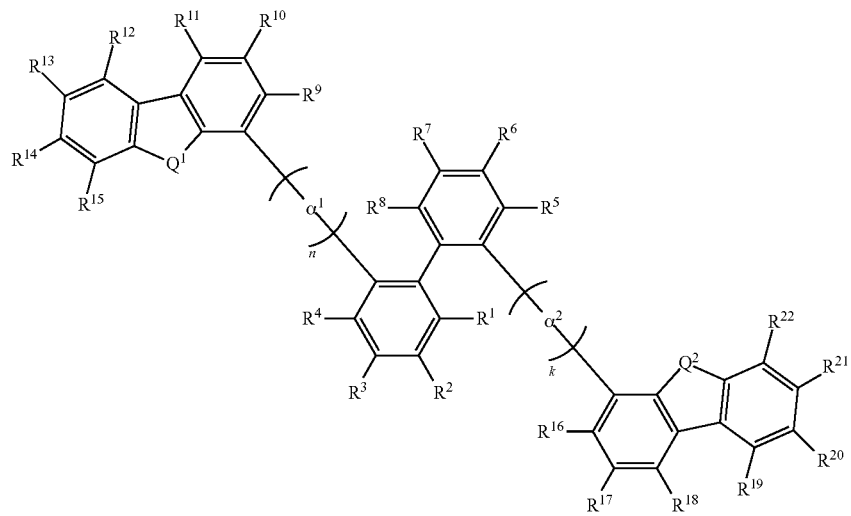

(G1)

wherein α¹ and α² separately represent a substituted or unsubstituted arylene group having 6 to 13 carbon atoms, wherein n and k separately represent 0 or 1, wherein Q¹ and Q² separately represent sulfur or oxygen, and wherein R¹ to R²² separately represent hydrogen, an alkyl group having 1 to 12 carbon atoms, or a substituted or unsubstituted aryl group having 6 to 14 carbon atoms.

11. The light-emitting element according to claim 10, wherein the layer comprising the heterocyclic compound is in contact with the anode.

12. The light-emitting element according to claim 10, wherein the layer comprising the heterocyclic compound comprises a metal oxide.

13. The light-emitting element according to claim 12, wherein the metal oxide is molybdenum oxide.

14. The light-emitting element according to claim 10, wherein the R¹ to R²² are separately represented by any one of the following structural formulae (R-1) to (R-14),

(R-1)

(R-2)

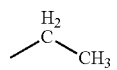
(R-3)

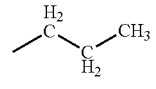
(R-4)

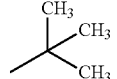
(R-5)

-continued

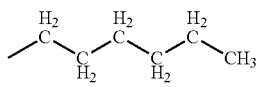
(R-6)

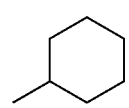
(R-7)

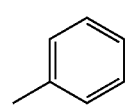
(R-8)

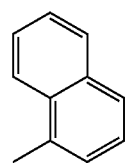
(R-9)

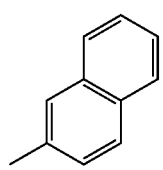
(R-10)

-continued

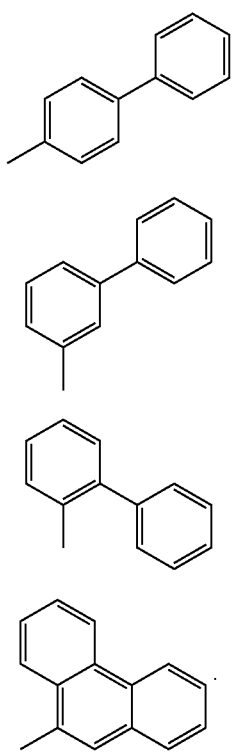

(R-11)

(R-12)

(R-13)

(R-14)

15. The light-emitting element according to claim 10, wherein the $\alpha^1$ or the $\alpha^2$ represents an arylene group having 6 to 13 carbon atoms and having one or more substituents, and
wherein the one or more substituents are separately an alkyl group having 1 to 12 carbon atoms or an aryl group having 6 to 14 carbon atoms.

16. The light-emitting element according to claim 15, wherein the one or more substituents are separately represented by any one of the following structural formulae (R-2) to (R-14),

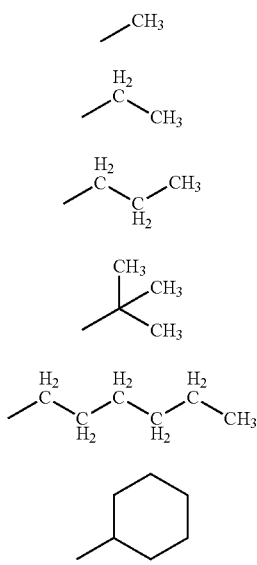

(R-2)
(R-3)
(R-4)
(R-5)
(R-6)
(R-7)

-continued

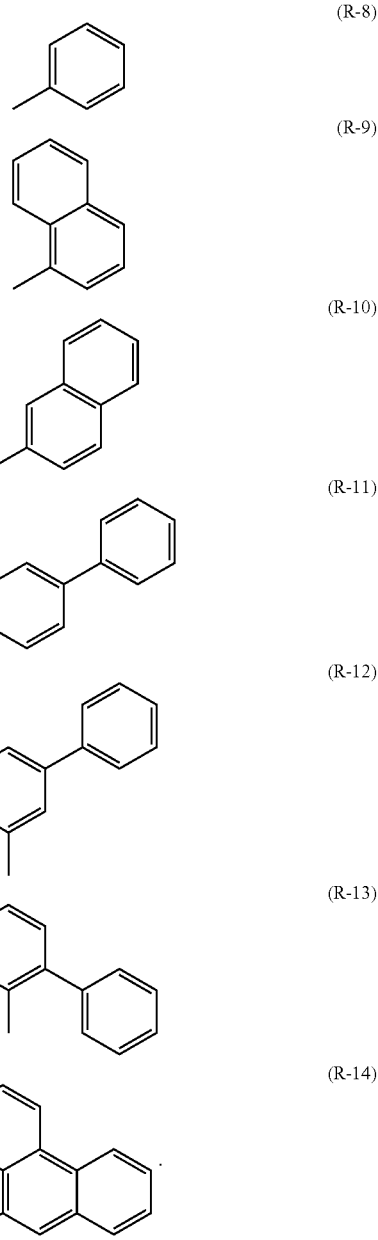

(R-8)
(R-9)
(R-10)
(R-11)
(R-12)
(R-13)
(R-14)

17. The light-emitting element according to claim 10, wherein the $\alpha^1$ and the $\alpha^2$ are separately represented by any one of the following structural formulae ($\alpha$-1) to ($\alpha$-11),

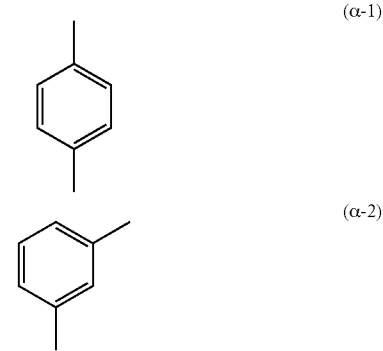

($\alpha$-1)

($\alpha$-2)

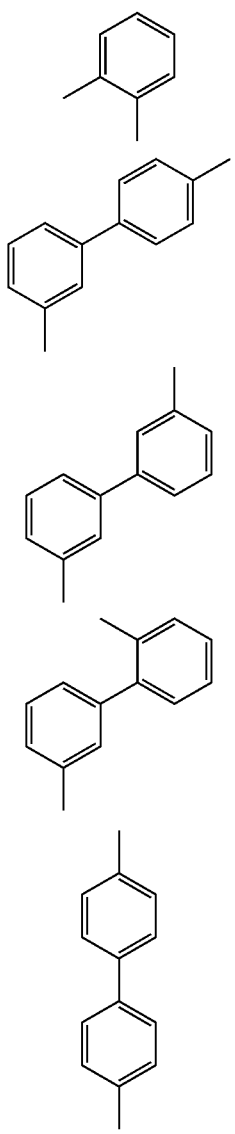

(α-3)
(α-4)
(α-5)
(α-6)
(α-7)

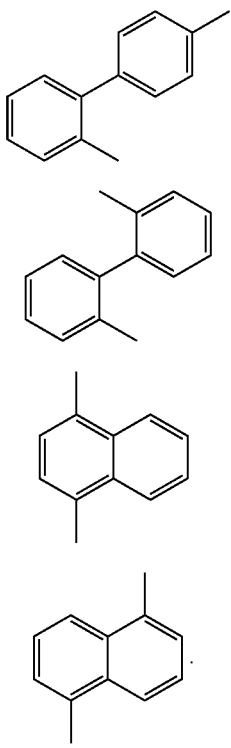

(α-8)
(α-9)
(α-10)
(α-11)

18. A light-emitting device comprising the light-emitting element according to claim 10.

19. An electronic device comprising the light-emitting device according to claim 18.

20. A lighting device comprising the light-emitting device according to claim 18.

21. A light-emitting element comprising:
an anode;
a cathode; and
a light-emitting layer between the anode and the cathode,
wherein the light-emitting layer comprises a light-emitting substance and a heterocyclic compound represented by the following general formula (G1),

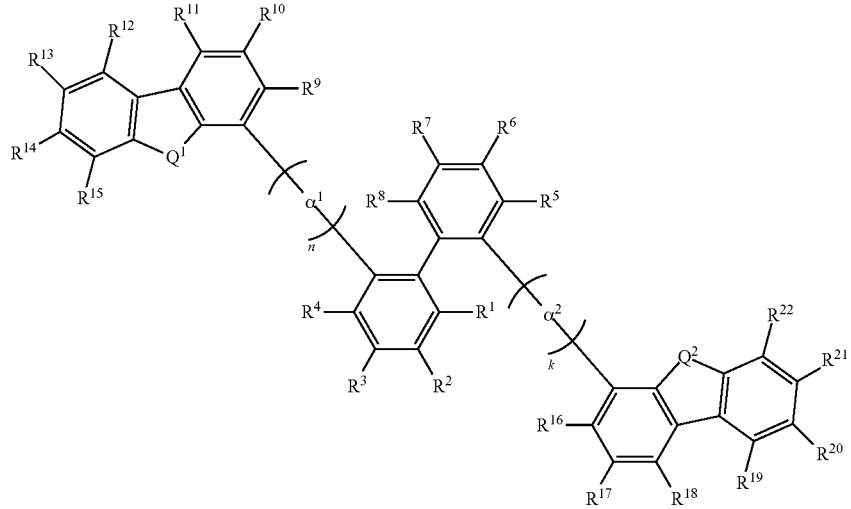

(G1)

wherein $\alpha^1$ and $\alpha^2$ separately represent a substituted or unsubstituted arylene group having 6 to 13 carbon atoms, wherein n and k separately represent 0 or 1, wherein $Q^1$ and $Q^2$ separately represent sulfur or oxygen, and wherein $R^1$ to $R^{22}$ separately represent hydrogen, an alkyl group having 1 to 12 carbon atoms, or a substituted or unsubstituted aryl group having 6 to 14 carbon atoms.

22. The light-emitting element according to claim 21, wherein the $R^1$ to $R^{22}$ are separately represented by any one of the following structural formulae (R-1) to (R-14),

 (R-1)

 (R-2)

 (R-3)

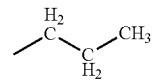 (R-4)

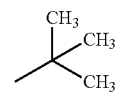 (R-5)

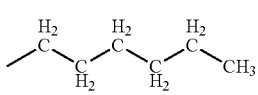 (R-6)

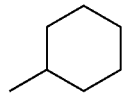 (R-7)

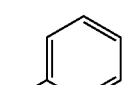 (R-8)

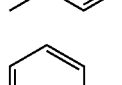 (R-9)

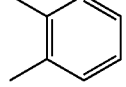 (R-10)

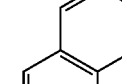 (R-11)

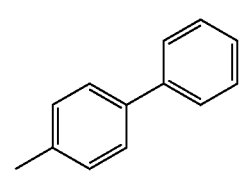 (R-12)

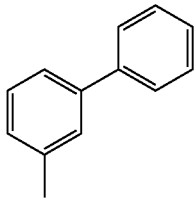 (R-12)

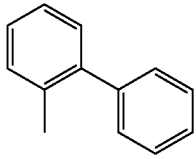 (R-13)

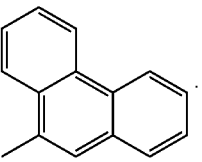 (R-14)

23. The light-emitting element according to claim 21, wherein the $\alpha^1$ or the $\alpha^2$ represents an arylene group having 6 to 13 carbon atoms and having one or more substituents, and wherein the one or more substituents are separately an alkyl group having 1 to 12 carbon atoms or an aryl group having 6 to 14 carbon atoms.

24. The light-emitting element according to claim 23, wherein the one or more substituents are separately represented by any one of the following structural formulae (R-2) to (R-14),

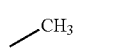 (R-2)

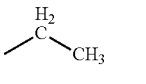 (R-3)

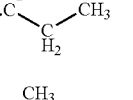 (R-4)

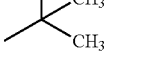 (R-5)

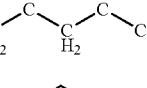 (R-6)

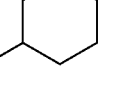 (R-7)

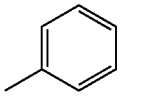 (R-8)

-continued
(R-9) 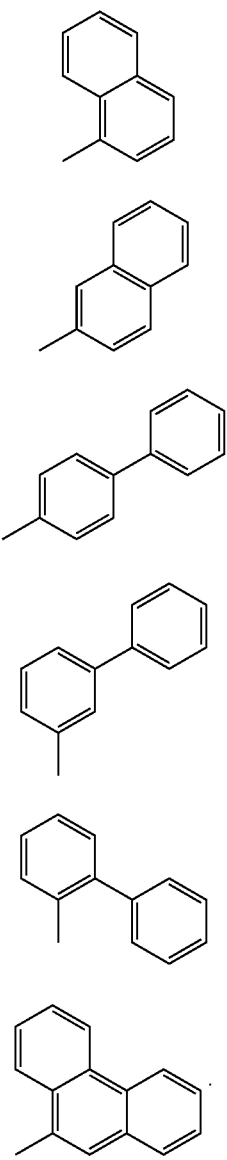
(R-10)
(R-11)
(R-12)
(R-13)
(R-14)
25. The light-emitting element according to claim 21, wherein the $\alpha^1$ and the $\alpha^2$ are separately represented by any one of the following structural formulae ($\alpha$-1) to ($\alpha$-11),
($\alpha$-1) 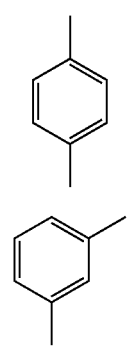
($\alpha$-2)
-continued
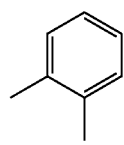 ($\alpha$-3)
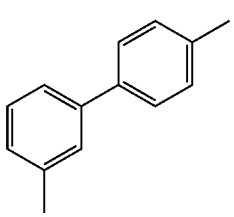 ($\alpha$-4)
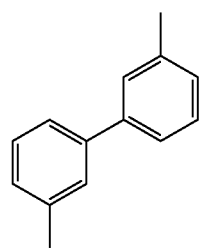 ($\alpha$-5)
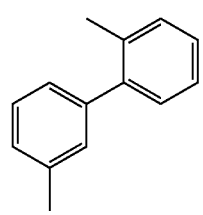 ($\alpha$-6)
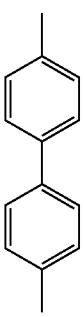 ($\alpha$-7)
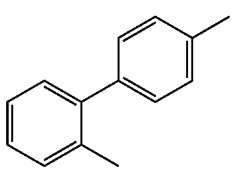 ($\alpha$-8)
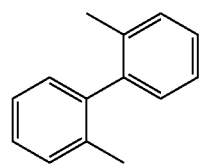 ($\alpha$-9)

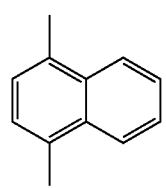
(α-10)
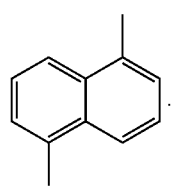
(α-11)
26. A light-emitting device comprising the light-emitting element according to claim 21.
27. An electronic device comprising the light-emitting device according to claim 26.
28. A lighting device comprising the light-emitting device according to claim 26.
* * * * *